US009554977B2

(12) United States Patent
Sabelle et al.

(10) Patent No.: US 9,554,977 B2
(45) Date of Patent: *Jan. 31, 2017

(54) TRIAROMATIC AZOMETHINE DIRECT DYES, DYE COMPOSITION COMPRISING AT LEAST ONE SUCH DYE, METHOD OF IMPLEMENTATION AND USE

(71) Applicant: L'OREAL, Paris (FR)

(72) Inventors: Stephane Sabelle, Paris (FR); Madeleine Leduc, Paris (FR); Olivier Guerard, Villemonble (FR)

(73) Assignee: L'OREAL, Paris (FR)

( * ) Notice: Subject to any disclaimer, the term of this patent is extended or adjusted under 35 U.S.C. 154(b) by 202 days.

This patent is subject to a terminal disclaimer.

(21) Appl. No.: 14/365,217

(22) PCT Filed: Dec. 13, 2012

(86) PCT No.: PCT/EP2012/075383
§ 371 (c)(1),
(2) Date: Jun. 13, 2014

(87) PCT Pub. No.: WO2013/087768
PCT Pub. Date: Jun. 20, 2013

(65) Prior Publication Data
US 2015/0320660 A1    Nov. 12, 2015

Related U.S. Application Data

(60) Provisional application No. 61/584,999, filed on Jan. 10, 2012.

(30) Foreign Application Priority Data

Dec. 13, 2011 (FR) ..................... 11 61576

(51) Int. Cl.
A61Q 5/10 (2006.01)
A61K 8/41 (2006.01)
C09B 55/00 (2006.01)
A61Q 5/06 (2006.01)
A61K 8/34 (2006.01)
A61K 8/35 (2006.01)
A61K 8/42 (2006.01)

(52) U.S. Cl.
CPC .............. A61K 8/411 (2013.01); A61K 8/34 (2013.01); A61K 8/35 (2013.01); A61K 8/41 (2013.01); A61K 8/42 (2013.01); A61Q 5/06 (2013.01); A61Q 5/065 (2013.01); A61Q 5/10 (2013.01); C09B 55/009 (2013.01); A61K 2800/4324 (2013.01); A61K 2800/88 (2013.01)

(58) Field of Classification Search
CPC .......... A61Q 5/10; A61Q 5/065; A61K 8/411; A61K 8/34; A61K 8/41; A61K 8/42; A61K 2800/88; C09B 55/009
USPC .............................. 8/405; 564/271
See application file for complete search history.

(56) References Cited

U.S. PATENT DOCUMENTS

| 3,787,174 | A | 1/1974 | Kalopissis et al. |
| 3,792,090 | A | 2/1974 | Kalopissis et al. |
| 3,817,699 | A | 6/1974 | Kalopissis et al. |
| 3,853,464 | A | 12/1974 | Kalopissis et al. |
| 3,867,094 | A | 2/1975 | Kalopissis et al. |
| 3,884,625 | A | 5/1975 | Kalopissis et al. |
| 3,894,837 | A | 7/1975 | Kalopissis et al. |
| 3,905,761 | A | 9/1975 | Kalopissis et al. |
| 3,929,404 | A | 12/1975 | Kalopissis et al. |
| 3,953,508 | A | 4/1976 | Kalopissis et al. |
| 3,963,764 | A | 6/1976 | Kalopissis et al. |
| 3,972,937 | A | 8/1976 | Kalopissis et al. |
| 3,984,402 | A | 10/1976 | Kalopissis et al. |
| 4,003,699 | A | 1/1977 | Rose et al. |
| 4,042,627 | A | 8/1977 | Kalopissis et al. |
| 4,045,170 | A | 8/1977 | Kalopissis et al. |
| 4,046,786 | A | 9/1977 | Kalopissis et al. |
| 4,054,147 | A | 10/1977 | Kalopissis et al. |
| 4,093,806 | A | 6/1978 | Kalopissis et al. |
| 4,112,229 | A | 9/1978 | Kalopissis et al. |
| RE30,199 | E | 1/1980 | Rose et al. |

(Continued)

FOREIGN PATENT DOCUMENTS

DE    2359399 A1    6/1975
DE    3843892 A1    6/1990

(Continued)

OTHER PUBLICATIONS

STIC Search Report dated Feb. 23, 2016.*

(Continued)

Primary Examiner — Eisa Elhilo
(74) Attorney, Agent, or Firm — The Marbury Law Group, PLLC

(57) ABSTRACT

The present invention relates to azomethine-type direct dyes having a triaromatic unit of formula (I) below: and also the use thereof for dyeing keratin fibers, in particular human keratin fibers such as the hair. The invention also relates to a composition for dyeing keratin fibers, comprising, in a medium suitable for dyeing, such direct dyes. Another subject of the present invention is a method for dyeing keratin fibers using said dye composition. Finally, the present invention also relates to precursors of these direct dyes.

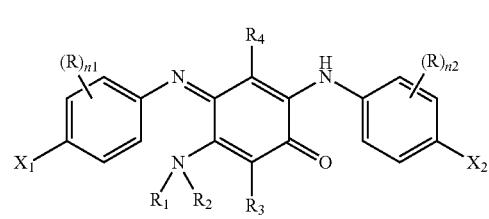

15 Claims, No Drawings

(56) References Cited

U.S. PATENT DOCUMENTS

| | | |
|---|---|---|
| 4,222,958 A | 9/1980 | Kalopissis et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 8,801,808 B2 * | 8/2014 | Lalleman .................. A61K 8/34 552/247 |
| 2002/0050013 A1 | 5/2002 | Vidal et al. |
| 2003/0019051 A9 | 1/2003 | Vidal et al. |
| 2011/0041263 A1 | 2/2011 | Leduc et al. |

FOREIGN PATENT DOCUMENTS

| | | |
|---|---|---|
| DE | 4133957 A1 | 4/1993 |
| DE | 19543988 A1 | 5/1997 |
| EP | 0714954 A2 | 6/1996 |
| EP | 0770375 A1 | 5/1997 |
| FR | 2047932 A1 | 3/1971 |
| FR | 2056799 A5 | 5/1971 |
| FR | 2106661 A5 | 5/1972 |
| FR | 2121101 A5 | 8/1972 |
| FR | 2165965 A1 | 8/1973 |
| FR | 2234277 A1 | 1/1975 |
| FR | 2262023 A1 | 9/1975 |
| FR | 2733749 A1 | 11/1996 |
| FR | 2886136 A1 | 12/2006 |
| FR | 2946647 A1 | 12/2010 |
| FR | 2801308 A1 | 5/2011 |
| GB | 1026978 A | 4/1966 |
| GB | 1153196 A | 5/1969 |
| JP | 02019576 A | 1/1990 |
| JP | 02265790 A | 10/1990 |
| JP | 5163124 A | 6/1993 |
| JP | 8259509 | * 10/1996 .......... C07C 251/22 |
| JP | 08259509 A | 10/1996 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 2010142777 A1 | 12/2010 |

OTHER PUBLICATIONS

International Search Report for PCT/EP2012/075383, (2012).
English language abstract for EP 0770375A1, (1997).
English language abstract for FR 2886136A1, (2006).
English language abstract for JP 02-265790A, (1990).
English language abstract for JP 08-259509A, (1996)
English language abstract for JP 02019576A, (1990)
English language abstract for JP 05163124A, (1990).

* cited by examiner

TRIAROMATIC AZOMETHINE DIRECT DYES, DYE COMPOSITION COMPRISING AT LEAST ONE SUCH DYE, METHOD OF IMPLEMENTATION AND USE

CROSS REFERENCE TO RELATED APPLICATIONS

This is a national stage application of PCT/EP2012/075383, filed internationally on Dec. 13, 2012, which claims priority to U.S. Provisional Application No. 61/584,999, filed on Jan. 10, 2012, as well as French Application FR 1161576, filed Dec. 13, 2011, all of which are incorporated herein by their entireties.

The present invention relates to particular triaromatic direct dyes of azomethine type and also to the use thereof for dyeing keratin fibres, in particular human keratin fibres such as the hair.

The invention also relates to a composition for dyeing keratin fibres comprising, in a medium suitable for dyeing, such direct dyes and also to a method for dyeing using said composition.

A final subject of the invention is the precursors of these direct dyes, the use thereof for dyeing fibres and a multi-compartment device containing them.

The present invention relates to the field of dyeing keratin fibres and more particularly to the field of hair dyeing.

It is known practice to dye keratin fibres, and in particular the hair, with dye compositions containing one or more direct dyes, according to a "direct dyeing" method.

The method conventionally used in direct dyeing consists in applying to the keratin fibres one or more direct dyes, or colouring molecules, which have an affinity for said fibres, leaving them on for a time, and then rinsing the fibres. The direct dyes used hitherto are generally nitrobenzene dyes, anthraquinone dyes, nitropyridine dyes, dyes of azo, xanthene, acridine or azine type or triarylmethane-type dyes.

These direct dyes may also be applied to the keratin fibres in the presence of an oxidizing agent if it is desired to obtain a simultaneous fibre-lightening effect.

However, the colours that result therefrom are temporary or semi-permanent colours since the nature of the interactions that bind the direct dyes to the keratin fibre and their desorption from the surface and/or the core of the fibre are responsible for their weak dyeing power and their poor fastness with respect to washing, inclement weather or perspiration.

Furthermore, such direct dyes are generally sensitive to the action of oxidizing agents, which makes them difficult to use in particular in lightening direct dye compositions that are formulated from aqueous hydrogen peroxide solution and an alkalinizing agent, which are similar to compositions used for oxidation dyeing. In other words, direct dyes are generally not very compatible with dye compositions intended to lighten the fibres and, consequently, using them in a lightening dyeing method, as an alternative to oxidation dyeing, is not yet entirely satisfactory.

These dyes also have the drawback of lacking light stability, due to the low resistance of the chromophore to photochemical attacks, which tends to lead to the colour of the keratin fibres fading over time.

Therefore there is a real need to have direct dyes that not only enable the keratin fibres to be dyed satisfactorily but that are also light-stable, capable of resulting in colours that resist the various attacks that the fibres may be subjected to, such as inclement weather, washing and perspiration, and further, that are sufficiently stable in the presence of oxidizing agents such as aqueous hydrogen peroxide solution to be able to deliver simultaneous lightening of the fibre with the advantages set out hereinabove.

These objectives are achieved with the present invention, which relates in particular to azomethine-type direct dyes having a triaromatic unit of formula (I) below, the organic or inorganic acid or base salts thereof, the tautomeric, optical isomer or geometric isomer forms thereof and/or the solvates thereof:

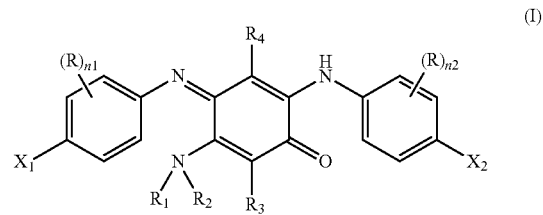

in which formula (I):
$n_1$ and $n_2$ represent, independently of one another, an integer equal to 0, 1, 2, 3 or 4;
R represents:
   a linear or branched $C_1$-$C_4$ alkyl radical, optionally substituted with one or more identical or different radicals selected from hydroxyl or imidazolium, An$^-$ radicals; An$^-$ denoting a cosmetically acceptable anion or mixture of anions;
   a $C_1$-$C_4$ alkoxy radical;
   a halogen atom;
$R_1$ represents:
   a hydrogen atom;
   a linear or branched $C_1$-$C_8$ alkyl radical, optionally substituted with one or more hydroxyl radicals;
   an aminocarbonyl radical;
   a radical of formula (II):

in which formula (II):
   m represents an integer equal to 0, 1, 2, 3 or 4;
   R' represents:
      a linear or branched $C_1$-$C_4$ alkyl radical, optionally substituted with one or more identical or different radicals selected from hydroxyl or imidazolium, An$^-$ radicals; An$^-$ denoting a cosmetically acceptable anion or mixture of anions;
      a $C_1$-$C_4$ alkoxy radical;
      a halogen atom;
      a hydroxyl radical;
      an —$NR'_3R'_4$ radical in which $R'_3$ and $R'_4$ represent, independently of one another:
         a hydrogen atom;
         a linear or branched $C_1$-$C_5$ alkyl radical, optionally substituted with one or more hydroxyl or $C_1$-$C_4$ alkoxy radicals;
      it being understood that, in formula (II), when m is greater than or equal to 2, the R' radicals may be identical or different;

$R_2$ represents:
- a hydrogen atom;
- a $C_1$-$C_8$ alkyl radical, optionally substituted with one or more hydroxyl radicals;

$R_1$ and $R_2$ may form, together with the nitrogen atom to which they are attached, a pyrrolidino, piperidino or morpholino ring;

$R_3$ and $R_4$ represent, independently of one another:
- a hydrogen atom;
- a linear or branched $C_1$-$C_8$ alkyl radical, optionally substituted with one or more hydroxyl radicals;
- a $C_1$-$C_4$ alkoxy radical;

$X_1$ and $X_2$ represent, independently of one another:
- a hydroxyl radical;
- an —$NR''_3R''_4$ radical in which:
  - $R''_3$ represents:
    - a hydrogen atom;
    - a linear $C_1$-$C_6$ alkyl radical;
  - $R''_4$ represents:
    - a hydrogen atom;
    - a linear or branched $C_3$-$C_6$ alkyl radical;
    - a linear or branched $C_2$-$C_6$ alkyl radical substituted with one or more hydroxyl radicals;

$R''_3$ and $R''_4$ may form, together with the nitrogen atom to which they are attached, a piperidino or morpholino ring;

it being understood that the compounds of formula (I) may not represent the compounds A to F below:

Compound A
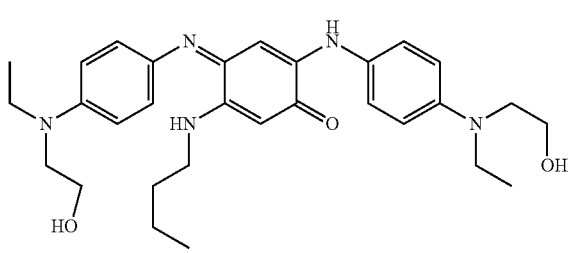

Compound B
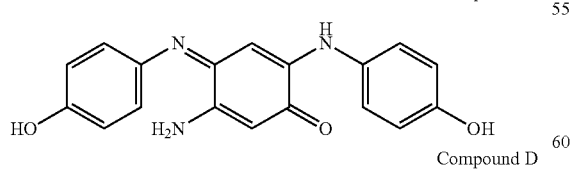

Compound C
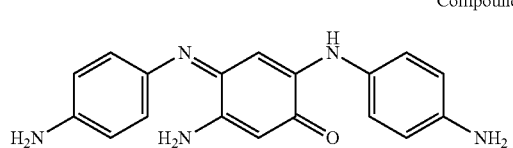

Compound D
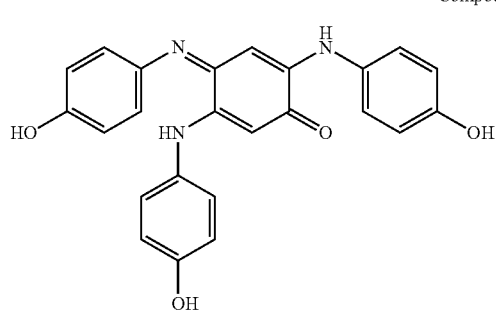

Compound E
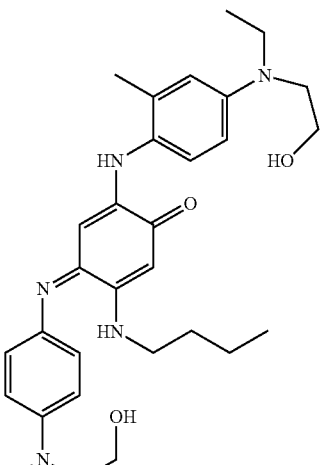

Compound F
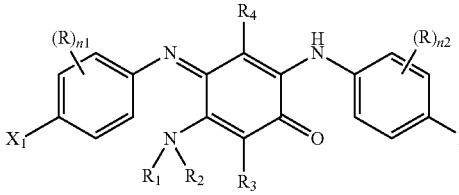

Another subject of the present invention relates to a composition for dyeing keratin fibres, in particular human keratin fibres such as the hair, comprising, in a medium suitable for dyeing, one or more azomethine-type dyes having a triaromatic unit of formula (I) below:

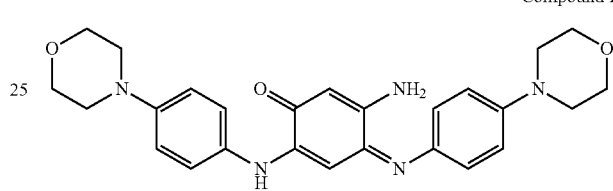

(I)

in which formula (I):

$n_1$ and $n_2$ represent, independently of one another, an integer equal to 0, 1, 2, 3 or 4;

R represents:
- a linear or branched $C_1$-$C_4$ alkyl radical, optionally substituted with one or more identical or different radicals selected from hydroxyl or imidazolium, $An^-$ radicals; $An^-$ denoting a cosmetically acceptable anion or mixture of anions;
- a $C_1$-$C_4$ alkoxy radical;
- a halogen atom;

$R_1$ represents:
- a hydrogen atom;
- a linear or branched $C_1$-$C_8$ alkyl radical, optionally substituted with one or more hydroxyl radicals;
- an aminocarbonyl radical;

a radical of formula (II):

$$\text{—}\underset{\underset{\text{(R')}_m}{\big|}}{\text{C}_6\text{H}_{4-m}}\quad (III)$$

in which formula (II):
- m represents an integer equal to 0, 1, 2, 3 or 4;
- R' represents:
  - a linear or branched $C_1$-$C_4$ alkyl radical, optionally substituted with one or more identical or different radicals selected from hydroxyl or imidazolium, $An^-$ radicals; $An^-$ denoting a cosmetically acceptable anion or mixture of anions;
  - a $C_1$-$C_4$ alkoxy radical;
  - a halogen atom;
  - a hydroxyl radical;
  - an —$NR'_3R'_4$ radical in which $R'_3$ and $R'_4$ represent, independently of one another:
    - a hydrogen atom;
    - a linear or branched $C_1$-$C_5$ alkyl radical, optionally substituted with one or more hydroxyl or $C_1$-$C_4$ alkoxy radicals;
  - it being understood that, in formula (II), when m is greater than or equal to 2, the R' radicals may be identical or different;
- $R_2$ represents:
  - a hydrogen atom;
  - a $C_1$-$C_8$ alkyl radical, optionally substituted with one or more hydroxyl radicals;
- $R_1$ and $R_2$ may form, together with the nitrogen atom to which they are attached, a pyrrolidino, piperidino or morpholino ring;
- $R_3$ and $R_4$ represent, independently of one another:
  - a hydrogen atom;
  - a linear or branched $C_1$-$C_8$ alkyl radical, optionally substituted with one or more hydroxyl radicals;
  - a $C_1$-$C_4$ alkoxy radical;
- $X_1$ and $X_2$ represent, independently of one another:
  - a hydroxyl radical;
  - an —$NR''_3R''_4$ radical in which:
    - $R''_3$ represents:
      - a hydrogen atom;
      - a linear $C_1$-$C_6$ alkyl radical;
    - $R''_4$ represents:
      - a hydrogen atom;
      - a linear or branched $C_3$-$C_6$ alkyl radical;
      - a linear or branched $C_2$-$C_6$ alkyl radical substituted with one or more hydroxyl radicals;
- $R''_3$ and $R''_4$ may form, together with the nitrogen atom to which they are attached, a piperidino or morpholino ring;
- it being understood that the compounds of formula (I) may not represent the compounds A to D below:

Compound A

Compound B

Compound C

Compound D

In particular, the invention also relates to the use of said dye composition for colouring keratin fibres, especially human keratin fibres such as the hair.

The present invention also relates to the use, for dyeing keratin fibres, in particular human keratin fibres such as the hair, of one or more azomethine-type dyes having a triaromatic unit of formula (I) below, the organic or inorganic acid or base salts thereof, the tautomeric, optical isomer or geometric isomer forms thereof and/or the solvates thereof:

(I)

in which formula (I) $n_1$, $n_2$, R, $R_1$, $R_2$, $R_3$, $R_4$, $X_1$ and $X_2$ have the same meanings as those indicated previously.

The invention additionally relates to a method for dyeing keratin fibres, in particular human keratin fibres such as the hair, in which applied to said fibres is a dye composition comprising, in a medium suitable for dyeing, one or more azomethine-type dyes having a triaromatic unit of formula (I) below, the organic or inorganic acid or base salts thereof, the tautomeric, optical isomer or geometric isomer forms thereof and/or the solvates thereof:

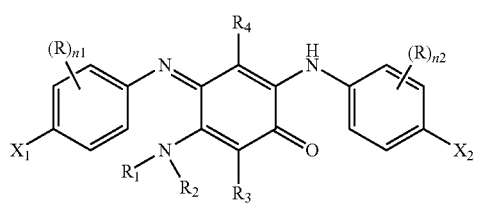

in which formula (I) $n_1$, $n_2$, R, $R_1$, $R_2$, $R_3$, $R_4$, $X_1$ and $X_2$ have the same meanings as those indicated previously; for a time sufficient to obtain the desired coloration, after which the fibres are rinsed, optionally washed with shampoo, rinsed again and the resulting fibres are dried or left to dry.

Similarly, the invention relates more particularly to a method for lightening keratin fibres, especially human keratin fibres such as the hair, in which applied to said fibres are (i) a dye composition free of oxidizing agent and comprising, in a medium suitable for dyeing, one or more azomethine-type dyes having a triaromatic unit of formula (I) below, the organic or inorganic acid or base salts thereof, the tautomeric, optical isomer or geometric isomer forms thereof and/or the solvates thereof:

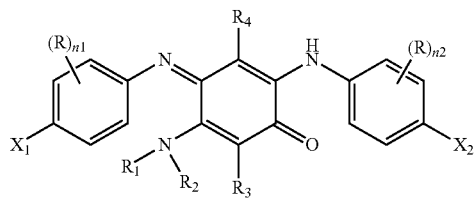

in which formula (I) $n_1$, $n_2$, R, $R_1$, $R_2$, $R_3$, $R_4$, $X_1$ and $X_2$ have the same meanings as those indicated previously; and (ii) a cosmetic composition comprising one or more oxidizing agents; compositions (i) and (ii) being applied to said keratin fibres sequentially or simultaneously for a time sufficient to obtain the desired lightening, after which the fibres are rinsed, optionally washed with shampoo, rinsed again and the resulting fibres are dried or left to dry.

The azomethine-type direct dyes having a triaromatic unit of formula (I) according to the invention thus make it possible to result in colours that resist the various attacks that the keratin fibres may be subject to, such as inclement weather, light, washing and perspiration.

Furthermore, the direct dyes according to the invention enable the keratin fibres to be dyed satisfactorily, especially by resulting in powerful, chromatic and sparingly selective colours and lead to an improved uptake of the colouration.

The direct dyes according to the invention are light-stable and can be used in the presence of an oxidizing agent, which facilitates their use in lightening direct dye compositions based on oxidizing agents.

In other words, the direct dyes according to the present invention lead to long-lasting colours and are compatible with dye compositions that are intended to lighten keratin fibres.

Furthermore, one subject of the invention is colourless or weakly coloured leuco-type compounds, which correspond to the reduced form of the azomethine-type direct dyes having a triaromatic unit according to the invention, of formula (III) below:

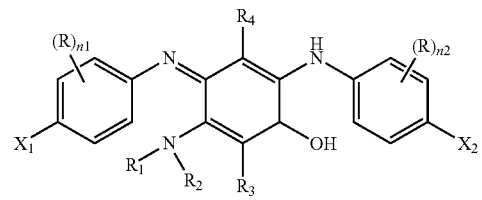

and the organic or inorganic acid or base salts thereof, the tautomeric, optical isomer or geometric isomer forms thereof and/or the solvates thereof;
in which formula (III) $n_1$, $n_2$, R, $R_1$, $R_2$, $R_3$, $R_4$, $X_1$ and $X_2$ have the same meanings as those indicated previously in formula (I).

The leuco-type compounds according to the invention may therefore lead, in the presence of one or more oxidizing agents, to azomethine-type direct dyes of formula (I).

Thus, the invention also relates to the use of one or more leuco-type compounds of formula (III) as precursors of the direct dyes of formula (I).

In particular, the invention relates to the use of one or more leuco-type compounds of formula (III) in the presence of one or more oxidizing agents for dyeing keratin fibres, especially human keratin fibres such as the hair.

The invention also relates to a multicompartment device or kit containing a first compartment comprising one or more leuco-type compounds of formula (III) as defined previously and a second compartment comprising one or more oxidizing agents.

The leuco-type compounds of formula (III) used under oxidizing conditions thus have the advantage of resulting in colours that resist the various attacks that the keratin fibres may be subjected to, such as inclement weather, washing, light or perspiration.

Other features, aspects, subjects and advantages of the present invention will become even more clearly apparent on reading the following description and examples.

I. Azomethine-Type Compound Having a Triaromatic Unit

The direct dyes of formula (I) according to the present invention comprise in their structure at least three aromatic rings and one azomethine bond.

$An^-$ denotes a cosmetically acceptable anion or mixture of anions, for instance halides, such as chloride; methosulfates; nitrates; alkylsulfonates: $Alk-S(O)_2O^-$ such as methylsulfonate or mesylate and ethylsulfonate; arylsulfonates: $Ar-S(O)_2O^-$ such as benzenesulfonate and toluenesulfonate or tosylate; citrate; succinate; tartrate; lactate; alkylsulfates: $Alk-O-S(O)O^-$ such as methylsulfate; arylsulfates such as benzenesulfate and toluenesulfate; phosphate; acetate; triflate; and borates such as tetrafluoroborate.

Preferably, $An^-$ is an anionic counterion selected from bromide, chloride, methylsulfate and toluenesulfonate ions or a mixture of these ions.

According to one embodiment, in formula (I), azomethine-type direct dyes according to the invention are such that, taken together or separately:
$n_1$ and $n_2$ represent, independently of one another, an integer equal to 0, 1 or 2;

R represents:
  a linear or branched $C_1$-$C_4$ alkyl radical, preferably a methyl radical;
  a $C_1$-$C_4$ alkoxy radical, preferably a methoxy radical;
  a halogen atom, preferably chlorine;
$R_1$ represents:
  a hydrogen atom;
  a linear or branched $C_1$-$C_8$ alkyl radical, optionally substituted with one or more hydroxyl radicals;
  an aminocarbonyl radical;
  a radical of formula (II):

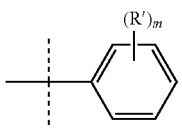

(II)

in which formula (II):
  m represents an integer equal to 0, 1, 2 or 3;
  R' represents:
    a linear or branched $C_1$-$C_4$ alkyl radical, preferably a methyl radical;
    a $C_1$-$C_4$ alkoxy radical, preferably a methoxy radical;
    a halogen atom, preferably chlorine;
    a hydroxyl radical;
    an —$NR'_3R'_4$ radical in which $R'_3$ and $R'_4$ represent, independently of one another:
      a hydrogen atom;
      a linear or branched $C_1$-$C_5$ alkyl radical, optionally substituted with one or more hydroxyl radicals;
    it being understood that, in formula (II), when m is greater than or equal to 2, the R' radicals may be identical or different;
$R_2$ represents:
  a hydrogen atom;
  a linear or branched $C_1$-$C_6$ alkyl radical, a butyl, methyl or ethyl radical;
$R_1$ and $R_2$ may form, together with the nitrogen atom to which they are attached, a pyrrolidino, piperidino or morpholino ring;
$R_3$ and $R_4$ represent, independently of one another:
  a hydrogen atom;
  a linear or branched $C_1$-$C_8$ alkyl radical, preferably a methyl or propyl radical;
  a $C_1$-$C_4$ alkoxy radical, preferably a methoxy radical;
it being understood that when $R_1$ and $R_2$ represent a hydrogen atom then $R_3$ and $R_4$ cannot simultaneously denote a hydrogen atom; and/or
$X_1$ and $X_2$ represent, independently of one another:
  a hydroxyl radical;
  an —$NR''_3R''_4$ radical in which:
    $R''_3$ represents:
      a hydrogen atom;
      a linear $C_1$-$C_6$ alkyl radical;
    $R''_4$ represents:
      a hydrogen atom;
      a linear or branched $C_3$-$C_6$ alkyl radical;
      a linear or branched $C_2$-$C_6$ alkyl radical substituted with one or more hydroxyl radicals;
    $R''_3$ and $R''_4$ may form, together with the nitrogen atom to which they are attached, a piperidino or morpholino ring.

Preferably, $n_1$ and $n_2$ represent an integer equal to 0, 1 or 2, and more preferably $n_1$ and $n_2$ are equal to 0 or 1.

Preferably, R represents a halogen atom, in particular chlorine, or a linear $C_1$-$C_4$ alkyl radical, in particular a methyl radical.

Preferably, $R_1$ represents a linear or branched $C_1$-$C_4$ alkyl radical, in particular a methyl, ethyl or butyl radical; a linear $C_1$-$C_4$ alkyl radical substituted with a hydroxyl radical, in particular a 2-hydroxyethyl radical; an aminocarbonyl radical; a radical of formula (II) in which m represents 0 or 1 and R' represents an —$NR'_3R'_4$ radical in which $R'_3$ and $R'_4$ represent a linear or branched $C_1$-$C_4$ alkyl radical.

More preferably, $R_1$ is selected from a methyl radical; a 2-hydroxyethyl radical; an aminocarbonyl radical; a radical of formula (II) in which m represents 0 or 1 with R' representing an —$NR'_3R'_4$ radical in which $R'_3$ and $R'_4$ represent a linear or branched $C_1$-$C_4$ alkyl radical.

In other words, $R_1$ is preferably other than a hydrogen atom.

Preferably, $R_2$ represents a hydrogen atom or a linear $C_1$-$C_4$ alkyl radical, preferably a butyl, methyl or ethyl radical.

More preferably, $R_2$ represents a hydrogen atom or a methyl radical.

More preferably still, $R_2$ represents a hydrogen atom.

Preferably, $R_3$ represents a hydrogen atom or a $C_1$-$C_4$ alkoxy radical, preferably a methoxy radical. In particular, $R_3$ represents a hydrogen atom.

Preferably, $R_4$ represents a hydrogen atom or a linear or branched $C_1$-$C_4$ alkyl radical, preferably a methyl radical. More preferably still, $R_4$ represents a hydrogen atom.

According to one embodiment, $R_3$ and $R_4$ represent a hydrogen atom.

According to one embodiment, $R_1$, $R_2$, $R_3$ and $R_4$ represent a hydrogen atom.

Preferably, $X_1$ and $X_2$ represent a hydroxyl radical or an —$NR''_3R''_4$ radical in which $R''_3$ represents a hydrogen atom or a linear $C_1$-$C_6$ alkyl radical and $R''_4$ represents a hydrogen atom or a linear or branched $C_3$-$C_6$ alkyl radical or a $C_2$-$C_6$ alkyl radical substituted with one or more hydroxyl radicals.

Preferentially, $X_1$ and $X_2$ represent a hydroxyl radical or an —$N'R''_3R''_4$ radical in which $R''_3$ represents a hydrogen atom or a linear $C_1$-$C_3$ alkyl radical and $R''_4$ represents a hydrogen atom or a linear or branched $C_3$-$C_4$ alkyl radical or a $C_2$-$C_4$ alkyl radical substituted with one or more hydroxyl radicals. Preferably, $R''_3$ represents a hydrogen atom or a methyl or ethyl radical and $R''_4$ represents a hydrogen atom or an isopropyl or 2-hydroxyethyl radical.

In other words, $X_1$ and $X_2$ preferably represent a hydroxyl radical.

Alternatively, $X_1$ and $X_2$ represent an —$N'R''_3R''_4$ radical in which $R''_3$ represents a hydrogen atom or a linear $C_1$-$C_3$ alkyl radical and $R''_4$ represents a hydrogen atom or a linear or branched $C_3$-$C_4$ alkyl radical, or a $C_2$-$C_4$ alkyl radical substituted with one or more hydroxyl radicals.

According to one embodiment, $n_1$ and $n_2$ represent an integer equal to 0 or 1, $R_1$ is other than a hydrogen atom, $R_2$ represents a hydrogen atom and $R_4$ represents a hydrogen atom.

According to one particular embodiment, $n_1$ and $n_2$ represent an integer equal to 0 or 1, $R_1$ is other than a hydrogen atom, $R_2$ represents a hydrogen atom, $R_4$ represents a hydrogen atom and $X_1$ and $X_2$ represent an —$N'R''_3R''_4$ radical in which $R''_3$ represents a hydrogen atom or a linear $C_1$-$C_3$ alkyl radical and $R''_4$ represents a hydrogen atom or a linear or branched $C_3$-$C_4$ alkyl radical or a $C_2$-$C_4$ alkyl radical substituted with one or more hydroxyl radicals.

According to another particular embodiment, $n_1$ and $n_2$ represent an integer equal to 0 or 1, $R_1$ is other than a hydrogen atom, $R_2$ represents a hydrogen atom, $R_4$ represents a hydrogen atom and $X_1$ and $X_2$ represent a hydroxyl radical.

In accordance with these two particular embodiments, $R_1$ may preferably represent a linear or branched $C_1$-$C_4$ alkyl radical; a linear $C_1$-$C_4$ alkyl radical substituted with a hydroxyl radical; an aminocarbonyl radical; a radical of formula (II) in which m represents 0 or 1 and R' represents an —$NR'_3R'_4$ radical in which $R'_3$ and $R'_4$ represent a linear or branched $C_1$-$C_4$ alkyl radical.

According to a preferred embodiment, $X_1$ and $X_2$ represent a —$NR''_3R''_4$ radical in which $R''_3$ and $R''_4$ represent a hydrogen atom.

According to another preferred embodiment, $X_1$ and $X_2$ represent a —$NR''_3R''_4$ radical in which $R''_3$ and $R''_4$ are different from a hydrogen atom.

According to a further embodiment, the direct dyes are chosen among the compounds of formula (I) wherein when $X_1$ or $X_2$ represent a —$NR''_3R''_4$ radical, $R''_4$ preferably represents a hydrogen atom or a branched or linear $C_3$-$C_6$ alkyl radical and $R''_3$ and $R''_4$ may form, together with the nitrogen atom to which they are attached, a piperidino ring.

According to this embodiment, $R''_4$ does not represent a linear of branched $C_2$-$C_6$ alkyl radical substituted with one or more hydroxyl radicals and $R''_3$ and $R''_4$ do not form, together with the nitrogen atom to which they are attached, a morpholino ring.

Preferably, the azomethine-type direct dyes having a triaromatic unit of formula (I) according to the invention are selected from the following compound, and also the geometric or optical isomer forms thereof, the organic or inorganic acid or base salts thereof, or the solvates thereof, such as the hydrates:

Compound 1

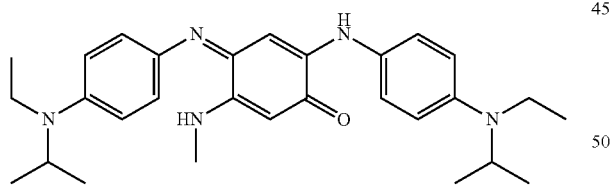

2-[4-(Ethylisopropyl-amino)phenyl-amino]-4-[4-(ethyl-isopropylamino)-phenylimino]-5-methylamicocyclohexa-2,5-dienone Compound 2

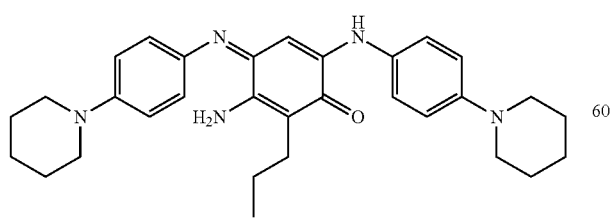

3-Amino-6-(4-piperidin-1-ylphenylamino)-4[4-piperidin-1-yl-phenylimino]-2-propyl-cyclohexa-2,5-dienone Compound 3

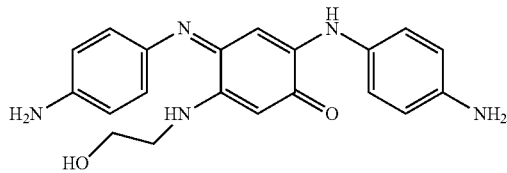

2-(4-Aminophenylamino)-4-(4-amino-phenylimino)-5-(2-hydroxyethylamino)-cyclohexa-2,5-dienone Compound 4

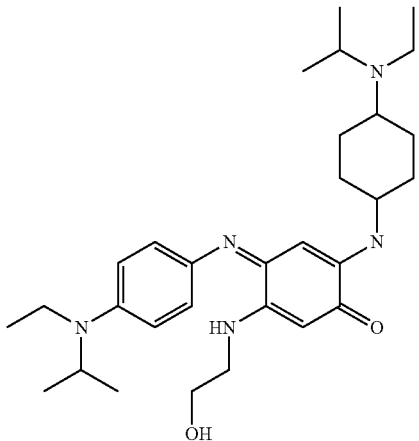

2-[4-(Ethylisopropyl-amino)phenyl-amino]-4-[4-(ethyl-isopropylamino)-phenylimino]-5-(2-hydroxyethylamino)-cyclohexa-2,5-dienone Compound 5

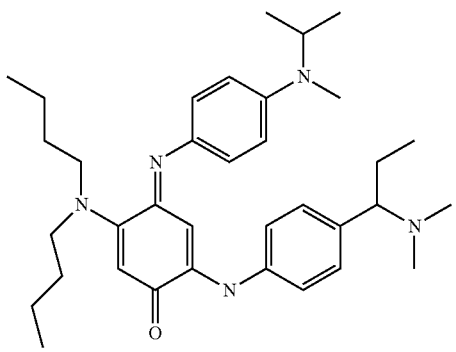

5-Dibutylamino-2-[4-ethyl-isopropylamino)-phenylamino]-4-[4-(ethyl-isopropylamino)phenylimino]-cyclohexa-2,5-dienone Compound 6

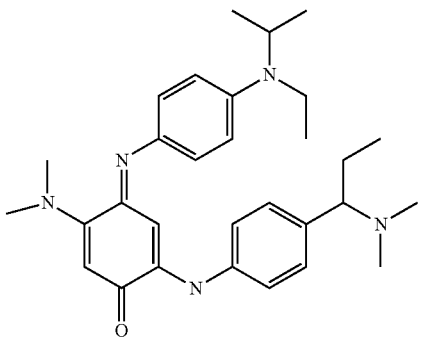

5-Dimethylamino-2-[4-(ethyl-isopropylamino)phenylamino]-4-[4-(ethyl-isopropylamino)-phenylamino]cyclohexa-2,5-dienone -continued Compound 7

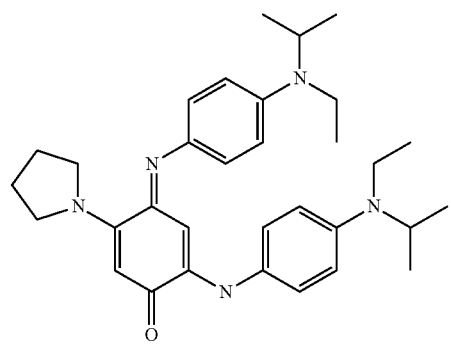

2-[4-(Ethylisopropylamino)-phenyl-amino]-4-[4-(ethylisopropyl-amino]phenylimino-5-pyrrolidin-1-ylcyclohexa-2,5-dienone Compound 8

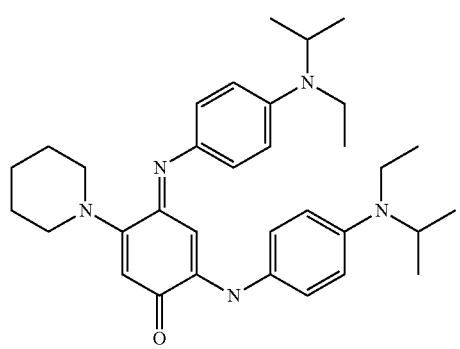

2-[4-(Ethylisopropylamino)-phenyl-amino]-4-[4-(ethylisopropylamino)-phenylimino]-5-piperidin-1-ylcyclohexa-2,5-dienone Compound 9

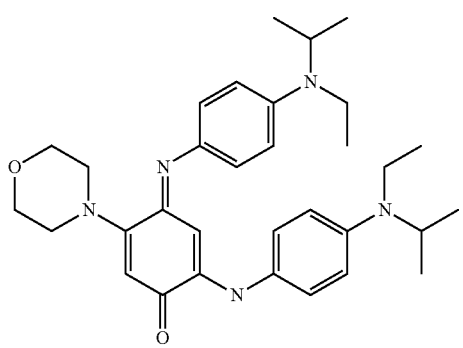

2-[4-(Ethylisopropylamino)phenyl-amino]-4-[4-(ethylisopropyl-amino)-phenylimino]-5-morpholin-4-ylcyclohexa-2,5-dienone Compound 10

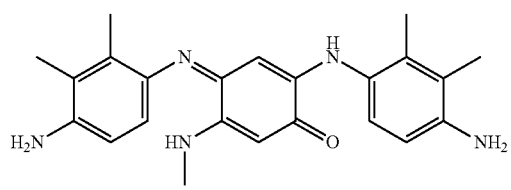

2-(4-Amino-2,3-dimethyl-phenylamino)-4-(4-amino-2,3-dimethylphenylimino)-5-methylaminocyclohexa-2,5-dienone Compound 11

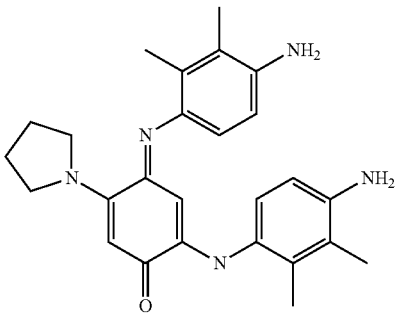

2-(4-Amino-2,3-dimethyl-phenylamino)-4-(4-amino-2,3-diethylphenylimino)-5-pyrrodlidin-1-ylcyclohexa-2,5-dienone Compound 12

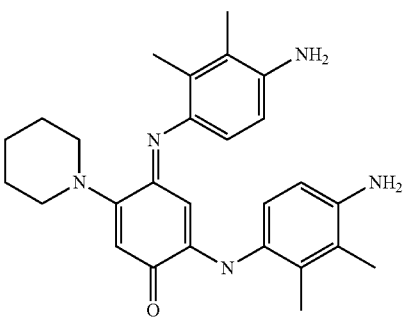

2-(4-Amino-2,3-dimethyl-phenylamino)-4-(4-amino-2,3-dimethylphenylimino)-5-piperidin-1-ylcyclohexa-2,5-dienone Compound 13

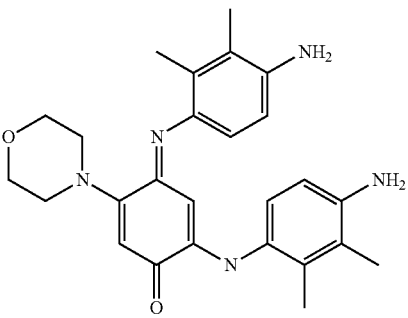

2-(4-Amino-2,3-dimethyl-phenylamino)-4-(4-amino-2,3-dimethylphenylimino)-5-morpholin-4-ylcyclohexa-2,5-dienone Compound 14

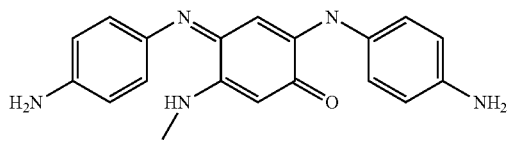

2-(4-Aminophenylamino)-4-(4-amino-phenylimino)-5-methylaminocyclohexa-2,5-dienone Compound 15

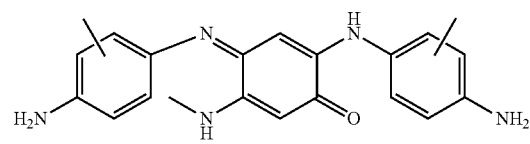

2-(4-Amino-3(or 2)-methyl-phenylamino)-4-(4-amino-3(or 2)-methyl-phenylimino)-5-methylaminocyclohexa-2,5-dienone -continued Compound 16

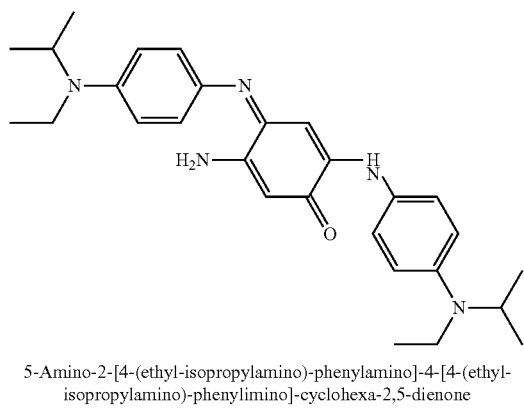

5-Amino-2-[4-(ethyl-isopropylamino)-phenylamino]-4-[4-(ethyl-isopropylamino)-phenylimino]-cyclohexa-2,5-dienone Compound 17

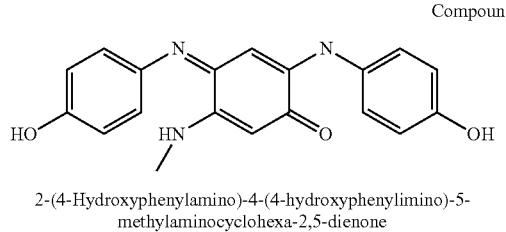

2-(4-Hydroxyphenylamino)-4-(4-hydroxyphenylimino)-5-methylaminocyclohexa-2,5-dienone Compound 18

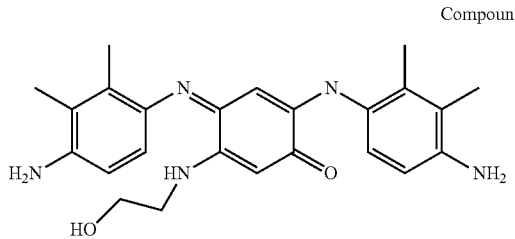

2-(4-Amino-2,3-dimethyl-phenylamino)-4-(4-amino-2,3-dimethylphenylimino)-5-(2-hydroxyethylamino)-cyclohexa-2,5-dienone Compound 19

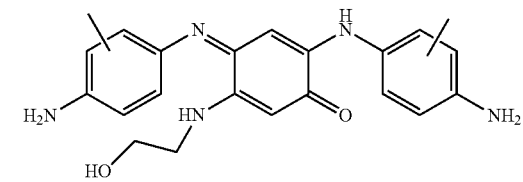

2-(4-Amino-3(or 2)-methyl-phenylamino)-4-(4-amino-3(or 2)-methyl-phenylimino)-5-(2-hydroxyethylamino)-cyclohexa-2,5-dienone Compound 20

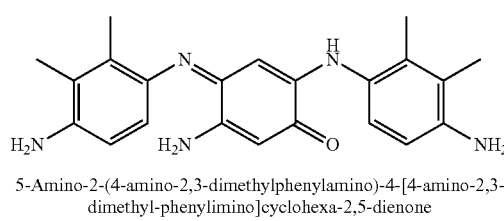

5-Amino-2-(4-amino-2,3-dimethylphenylamino)-4-[4-amino-2,3-dimethyl-phenylimino]cyclohexa-2,5-dienone Compound 21

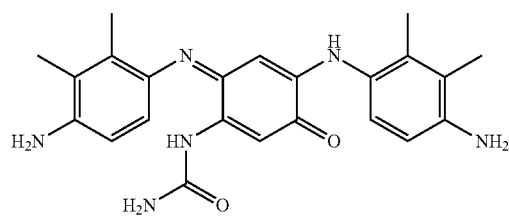

[4-(4-Amino-2,3-dimethyl-phenylamino)-6-(4-amino-2,3-dimethylphenylimino)-3-oxocyclohexa-1,4-dienyl]-urea Compound 22

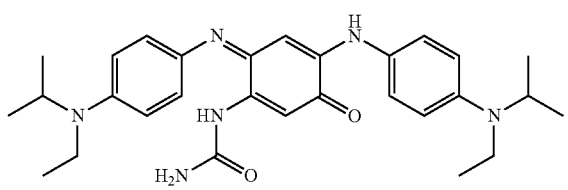

{4-[4-(Ethylisopropylamino)phenylamino]-6-[4-(ethyl-isopropylamino)-phenylimino]-3-oxocyclohexa-1,4-dienyl}urea Compound 23

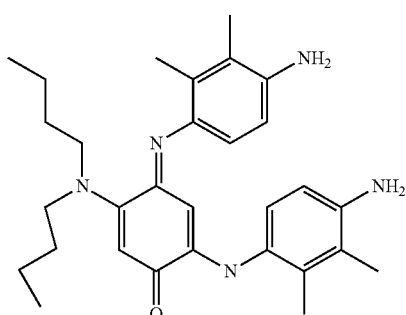

2-(4-Amino-2,3-dimethyl-phenylamino)-4-(4-amino-2,3-dimethylphenylimino)-5-dibutylaminocyclohexa-2,5-dienone Compound 24

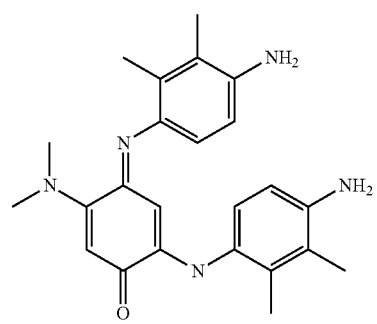

2-(4-Amino-2,3-dimethyl-phenylamino)-4-(4-amino-2,3-dimethylphenylimino)-5-dimethylaminocyclohexa-2,5-dienone Compound 25

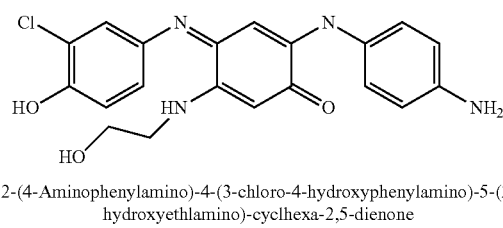

2-(4-Aminophenylamino)-4-(3-chloro-4-hydroxyphenylamino)-5-(2-hydroxyethlamino)-cyclhexa-2,5-dienone Compound 26

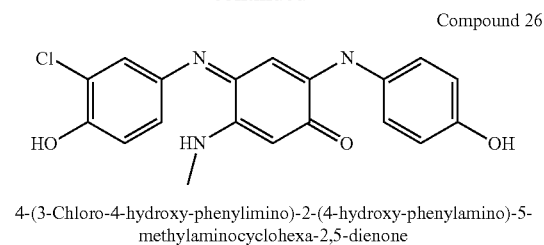

4-(3-Chloro-4-hydroxy-phenylimino)-2-(4-hydroxy-phenylamino)-5-methylaminocyclohexa-2,5-dienone Compound 27

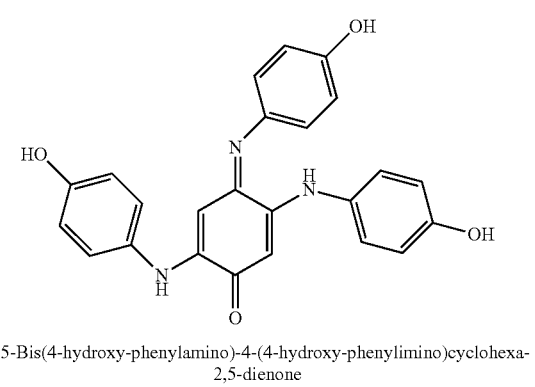

2,5-Bis(4-hydroxy-phenylamino)-4-(4-hydroxy-phenylimino)cyclohexa-2,5-dienone

Compound 28

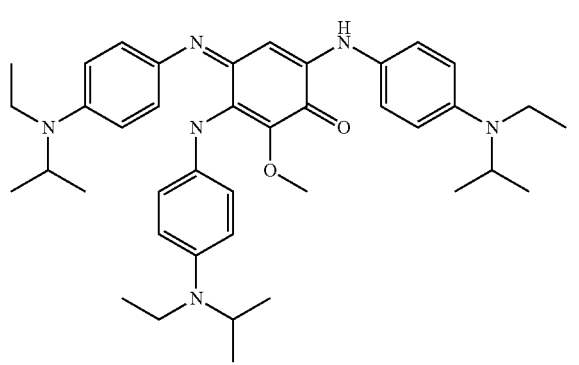

3,6-Bis[4-(ethylisopropyl-amino)-phenylamino]-4-[4-(ethyl-isopropyl-amino)phenylimino]-2-methoxycyclohexa-2,5-dienone Compound 29

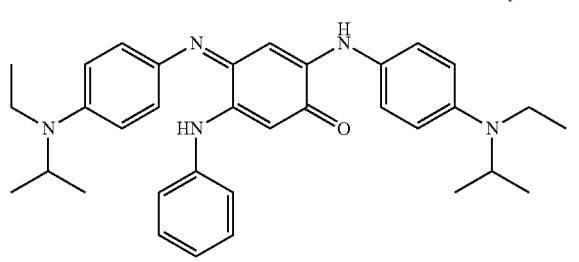

2-[4-Ethylsopropylamino)-phenyl-amino]-4-[4-(ethylisopropyl-amino)-phenylimino]-5-phenylaminocyclohexa-2,5-dienone Compound 30

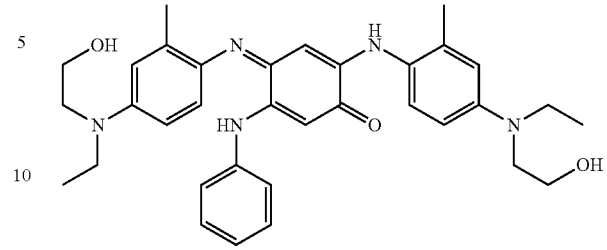

2-{4-[ethyl-(2-hydroxy-ethyl)amino]-2-methyl-phenylamino}-4-{4-[ethyl-(2-hydroxyethyl)amino]-2-methyl-phenylimino}-5-phenylaminocyclohexa-2,5-dienone Compound 31

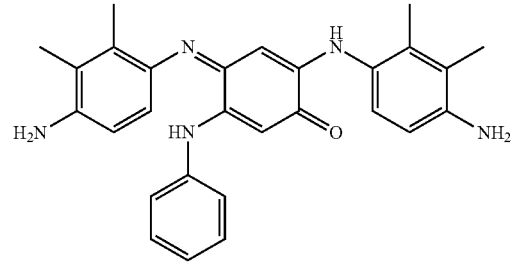

2-(4-Amino-2,3-dimethyl-phenylamino)-4-(4-amino-2,3-dimethylphenylimino)-5-phenylaminocyclohexa-2,5-dienone Compound 32

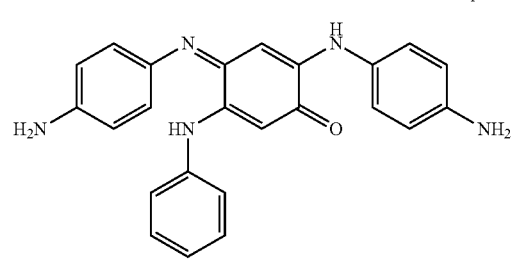

(4-Aminophenylamino)-4-(4-amino-phenylimino)-5-phenylaminocyclohexa-2,5-dienone

Compound 33

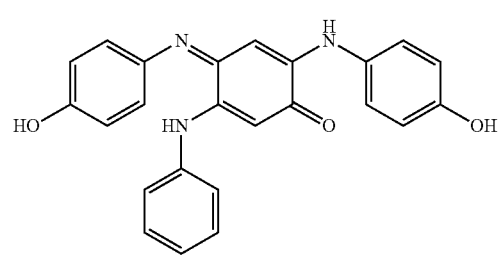

2-(4-Hydroxy-phenylamino)-4-(4-hydroxyphenylimino)-5-phenylaminocyclohexa-2,5-dienone -continued Compound 34

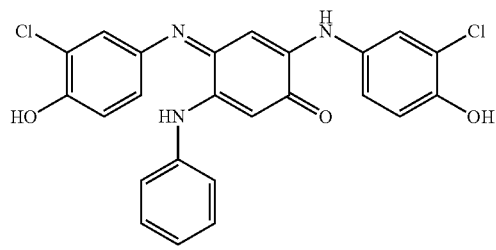

2-(3-Chloro-4-hydroxy-phenylamino)-4-(3-chloro-4-hydroxy-phenylimino)-5-phenylaminocyclohexa-2,5-dienone Compound 35

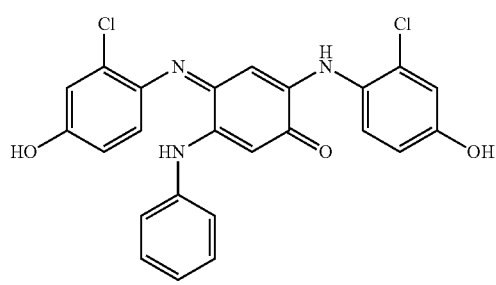

2-(2-Chloro-4-hydroxy-phenylamino)-4-(2-chloro-4-hydroxy-phenylimino)-5-phenylaminocyclohexa-2,5-dienone Compound 36

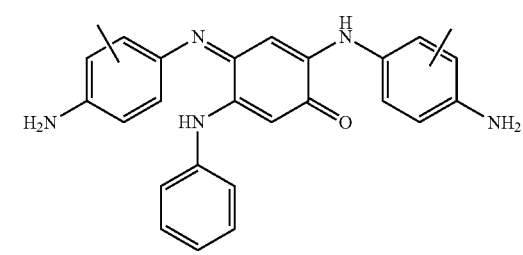

2-(4-Amino-3(or 2)-methyl-phenylamino)-4-(4-amino-3(or 2)-methyl-phenylimino)-5-phenylaminocyclohexa-2,5-dienone Compound 37

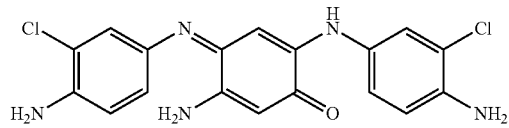

5-Amino-2-(4-amino-3-chlorophenylamino)-4-[4-amino-3-chlorophenylimino]cyclohexa-2,5-dienone Compound 38

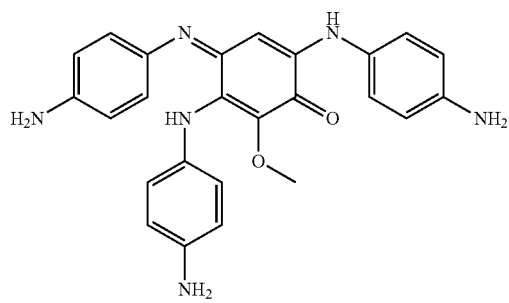

3,6-Bis(4-aminophenylamino)-4-(4-aminophenylimino)-2-methoxycyclohexa-2,5-dienone Compound 39

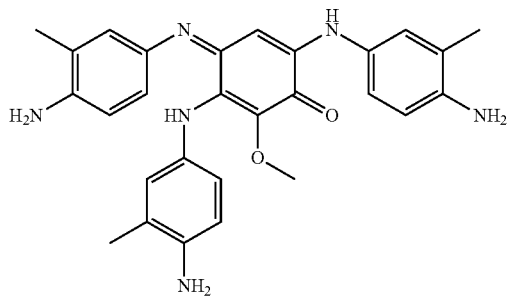

3,6-Bis(4-amino-3-methyl-phenylamino)-4-(4-amino-3-methylphenylimino)-2-methoxycyclohexa-2,5-dienone Compound 40

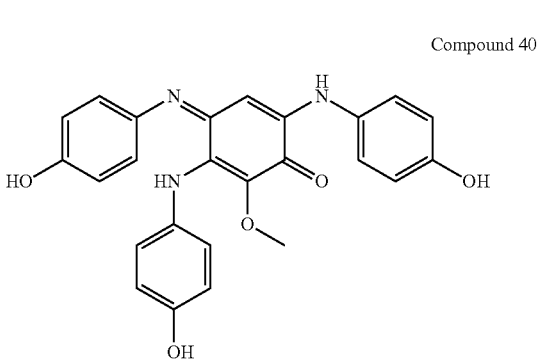

3,6-Bis(4-hydroxy-phenylamino)-4-(4-hydroxy-phenylimino)-2-methoxy-cyclohexa-2,5-dienone Compound 41

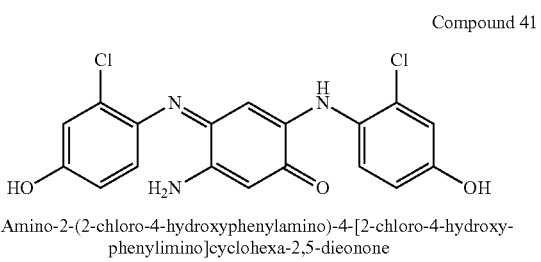

5-Amino-2-(2-chloro-4-hydroxyphenylamino)-4-[2-chloro-4-hydroxy-phenylimino]cyclohexa-2,5-dieonone Compound 42

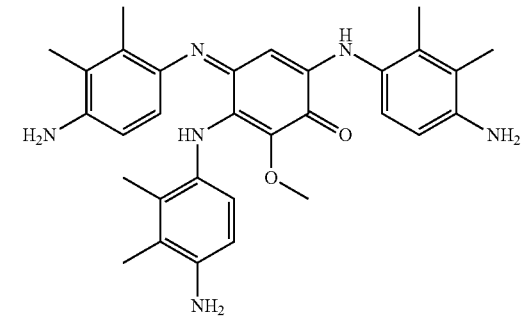

3,6-Bis(4-amino-2,3-dimethylphenylamino)-4-(4-amino-2,3-dimethyl-phenylimino)-2-methoxy-cyclohexa-2,5-dienone -continued Compound 43

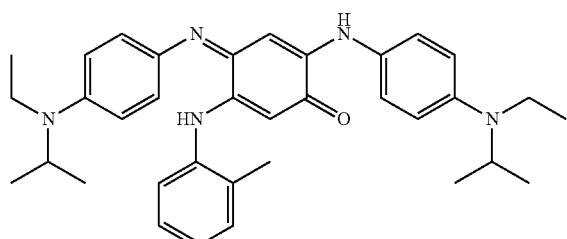

2-[4-(Ethylisopropylamino)-phenyl-amino]-4-[4-ethylisopropyl-amino)-phenylimino]-5-o-tolyaminocyclohexa-2,5-dienone Compound 44

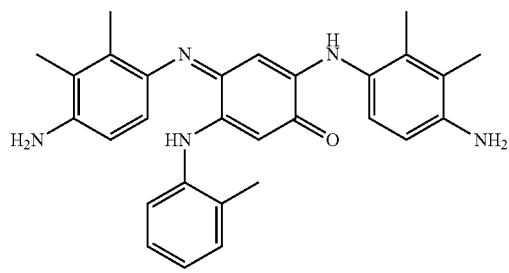

2-(4-Amino-2,3-dimethyl-phenylamino)-4-(4-amino-2,3-dimethylphenylimino)-5-o-tolylaminocyclohexa-2,5-dienone Compound 45

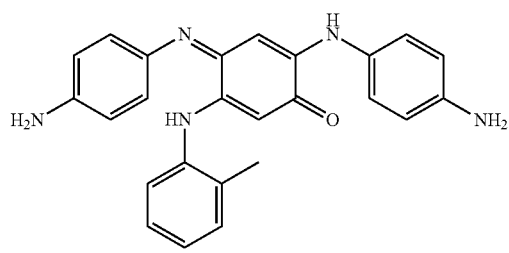

2-(4-Aminophenyl-amino)-4-(4-amino-phenylimino)-5-o-tolylaminocyclohexa-2,5-dienone Compound 46

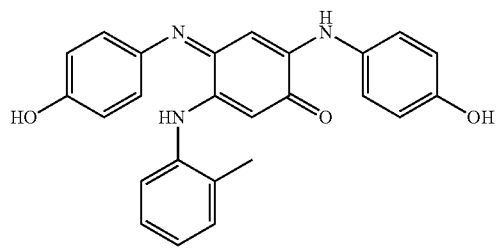

2-(4-Hydroxyphenylamino)-4-(4-hydroxyphenylimino)-5-o-tolylaminocyclohexa-2,5-dienone -continued Compound 47

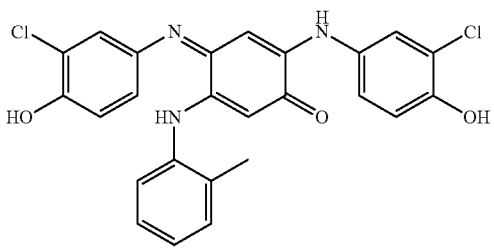

2-(3-Chloro-4-hydroxy-phenylamino)-4-(3-chloro-4-hydroxy-phenylimino)-5-o-tolylaminocyclohexa-2,5-dienone Compound 48

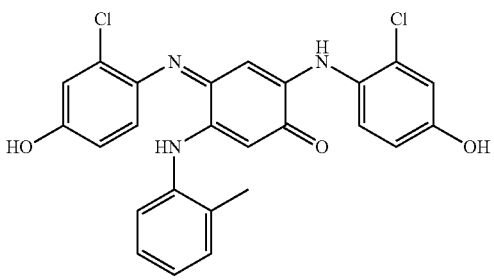

2-(2-Chloro-4-hydroxy-phenylamino)-4-(2-chloro-4-hydroxy-phenylimino)-5-o-tolylaminocyclohexa-2,5-dienone Compound 49

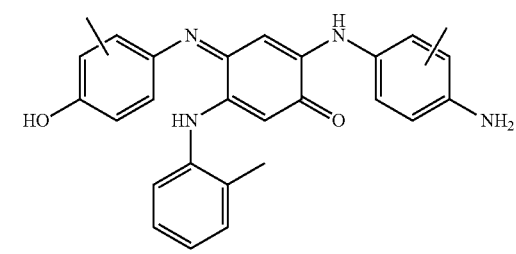

2-(4-Amino-3(or 2)-methyl-phenylamino)-4-(4-amino-3(or 2)-methyl-phenylimino)-5-o-tolylaminocyclohexa-2,5-dienone Compound 50

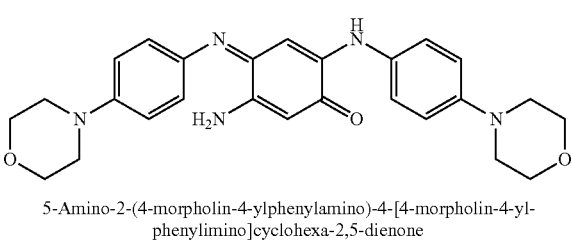

5-Amino-2-(4-morpholin-4-ylphenylamino)-4-[4-morpholin-4-yl-phenylimino]cyclohexa-2,5-dienone Compound 51

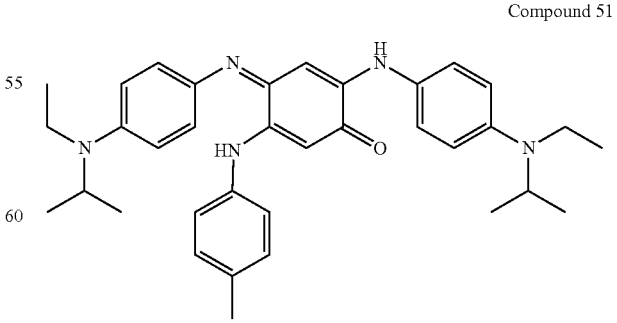

2-[4-(Ethylisopropylamino)phenyl-amino]-4-[4-(ethylisopropyl-amino)-phenylimino]-5-p-tolyaminocyclohexa-2,5-dienone -continued Compound 52

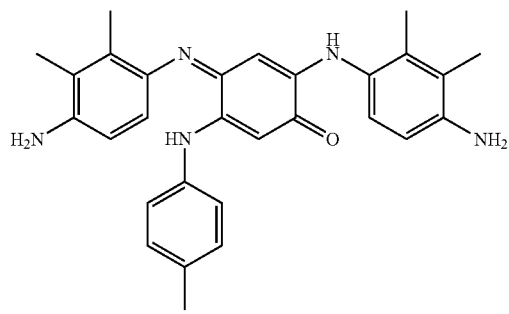

2-(4-Amino-2,3-dimethyl-phenylamino)-4-(4-amino-2,3-dimethylphenylimino)-5-p-tolylaminocyclohexa-2,5-dienone Compound 53

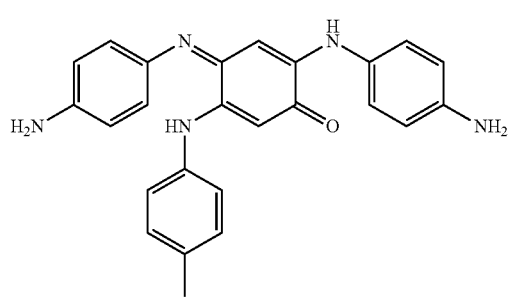

2-(4-Aminophenylamino)-4-(4-amino-phenylimino)-5-p-tolylaminocyclohexa-2,5-dienone Compound 54

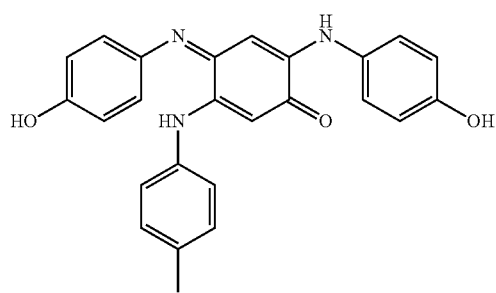

2-(4-Hydroxy-phenylamino)-4-(4-hydroxyphenylimino)-5-p-tolylaminocyclohexa-2,5-dienone Compound 55

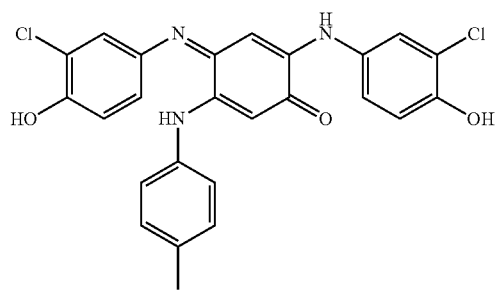

2-(3-Chloro-4-hydroxy-phenylamino)-4-(3-chloro-4-hydroxy-phenylimino)-5-p-tolylaminocyclohexa-2,5-dienone Compound 56

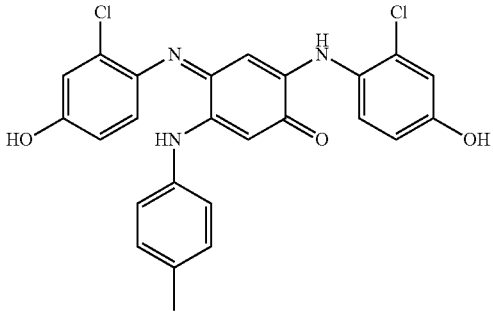

2-(2-Chloro-4-hydroxy-phenylamino)-4-(2-chloro-4-hydroxy-phenylimino)-5-p-tolylaminocyclohexa-2,5-dienone Compound 57

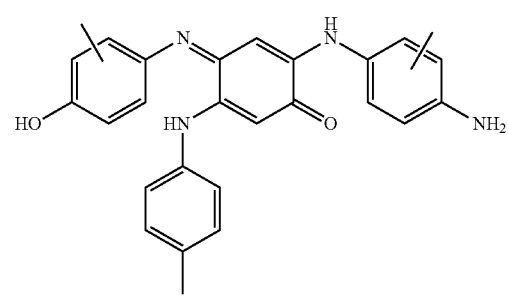

2-(4-Amino-3(or 2)-methyl-phenylamino)-4-(4-amino-3(or 2)-methyl-phenylimino)-5-p-tolylaminocyclohexa-2,5-dienone Compound 58

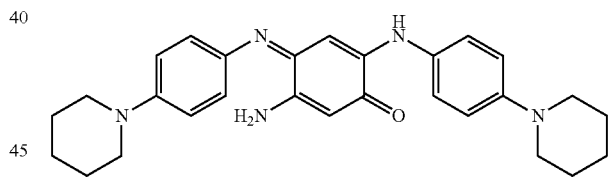

5-Amino-2-(4-piperidin-1-ylphenylamino)-4-[4-piperidin-1-ylphenylimino]cyclohexa-2,5-dienone Compound 59

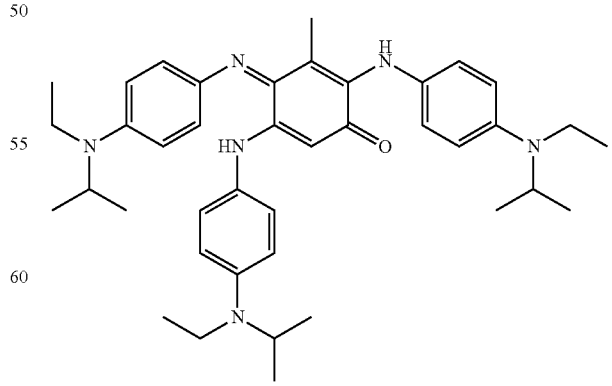

2,5-Bis[4-(ethylisopropyl-amino)-phenylamino]-4-[4-(ethyl-isopropyl-amino)phenylimino]-3-methylcyclohexa-2,5-dienone -continued Compound 60

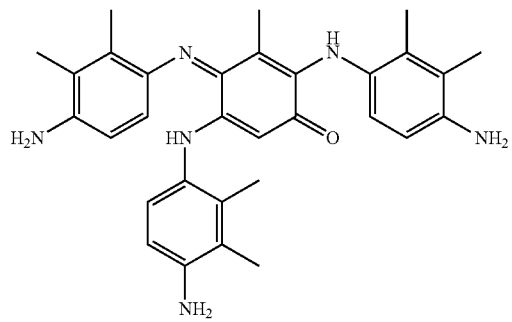

2,5-Bis(4-amino-2,3-dimethyl-phenylamino)-4-(4-amino-2,3-dimethyl-phenylimino)-3-methyl-cyclohexa-2,5-dienone Compound 61

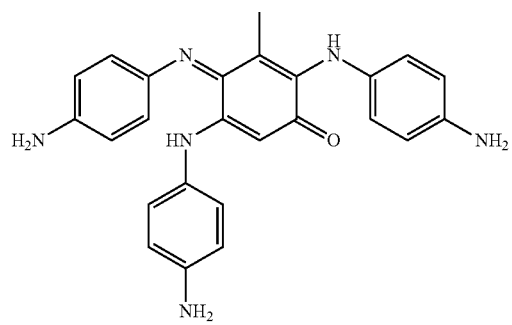

2,5-Bis(4-aminophenylamino)-4-(4-aminophenylimino)-3-methyl-cyclohexa-2,5-dienone Compound 62

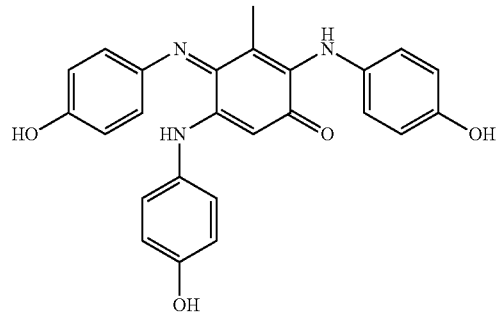

2,5-Bis(4-hydroxy-phenylamino)-4-(4-hydroxy-phenylimino)-3-methyl-cyclohexa-2,5-dienone Compound 63

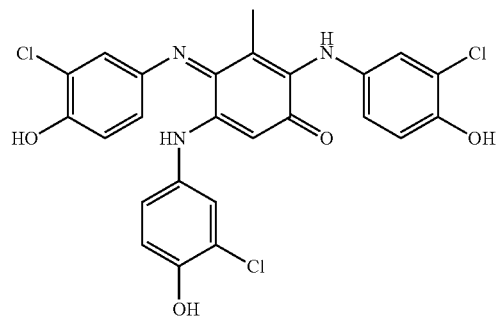

2,5-Bis(3-chloro-4-hydroxy-phenylamino)-4-(3-chloro-4-hydroxyphenylimino)-3-methylcyclohexa-2,5-dienone -continued Compound 64

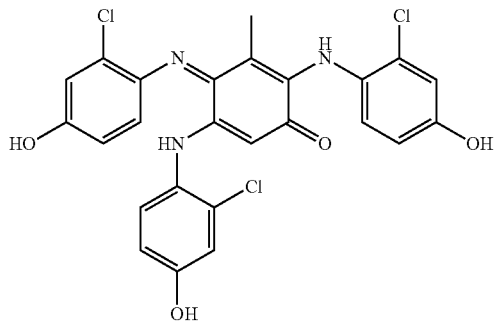

2,5-Bis(2-chloro-4-hydroxy-phenylamino)-4-(2-chloro-4-hydroxyphenylimino)-3-methylcyclohexa-2,5-dienone Compound 65

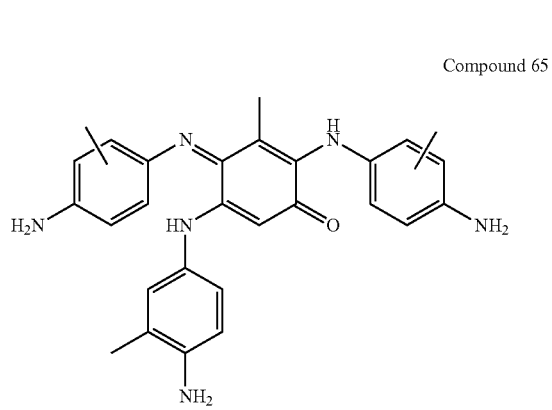

2,5-Bis(4-amino-3(or 2)-methylphenylamino)-4-(4-amino-3(or 2)-methyl-phenylimino)-3-methyl-cyclohexa-2,5-dienone Compound 66

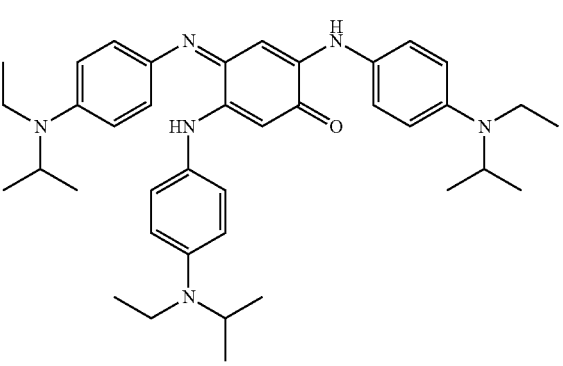

5-Amino-3-methyl-2-(4-morpholin-4-ylphenylamino)-4-[4-morpholin-4-ylphenylimino]cyclohexa-2,4-dienone Compound 67

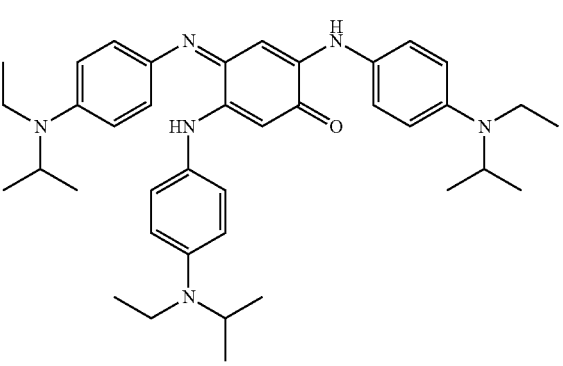

2,5-Bis[4-(ethylisopropyl-amino)-phenylamino]-4-[4-(ethylisopropyl-amino)-phenylimino]cyclohexa-2,5-dienone -continued Compound 68

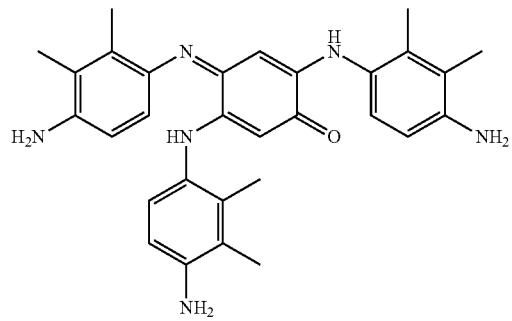

2,5-Bis(4-amino-2,3-dimethylphenylamino)-4-(4-amino-2,3-dimethyl-phenylimino)cyclohexa-2,5-dienone Compound 69

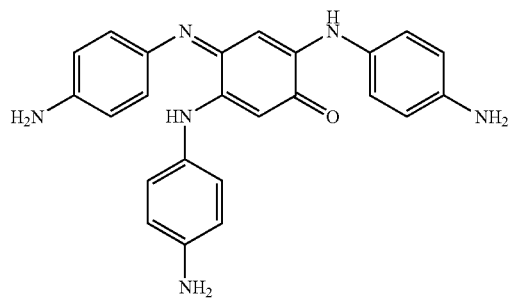

2,5-Bis(4-amino-phenylamino)-4-(4-aminophenylimino)-cyclohexa-2,5-dienone

Compound 70

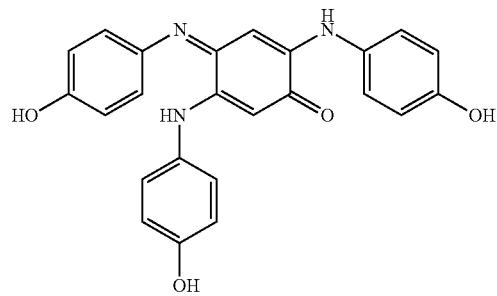

2,5-Bis(4-hydroxy-phenylamino)-4-(4-hydroxyphenylimino)-cyclohexa-2,5-dienone

Compound 71

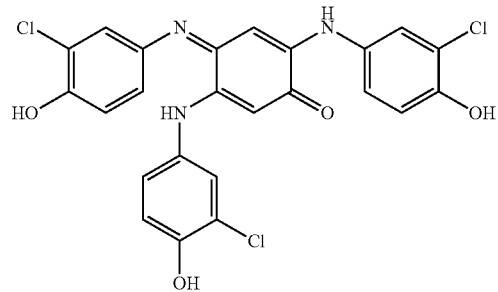

2,5-Bis(3-chloro-4-hydroxyphenylamino)-4-(3-chloro-4-hydroxy-phenylimino)cyclohexa-2,5-dienone -continued Compound 72

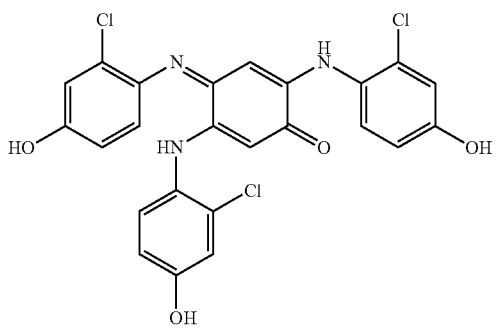

2,5-Bis(2-chloro-4-hydroxy-phenylamino)-4-(2-chloro-4-hydroxyphenylimino)cyclohexa-2,5-dienone Compound 73

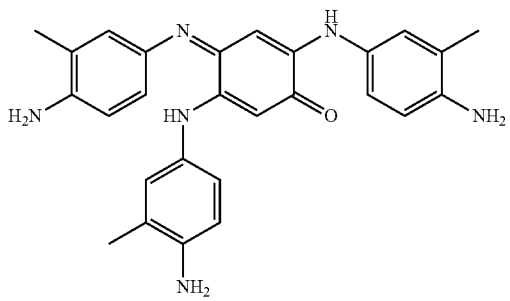

2,5-Bis(4-amino-3-methyl-phenylamino)-4-(4-amino-3-methylphenylimino)cyclohexa-2,5-dienone Compound 74

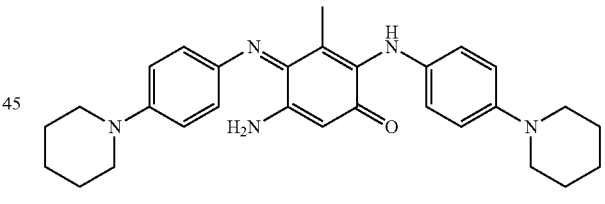

5-Amino-3-methyl-2-(4-piperidin-1-yl-phenylamino)-4-[4-piperidin-1-ylphenylimino]cyclohexa-2,5-dienone Compound 75

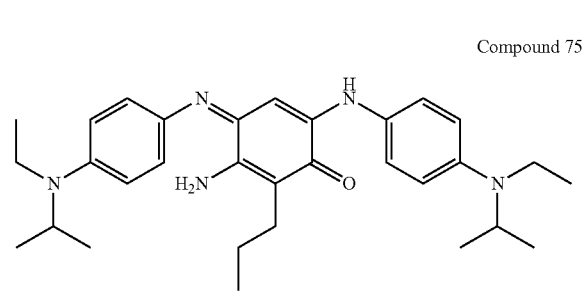

3-Amino-6-[4-(ethyl-isopropylamino)-phenylamino]-4-[4-ethyl-isopropylamino)-phenylimino]-2-propyl-cyclohexa-2,5-dienone Compound 76

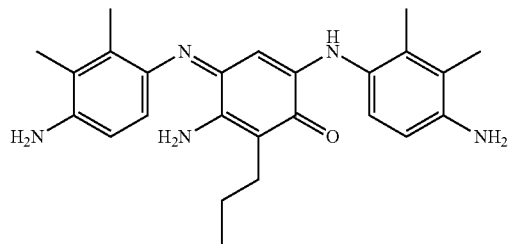

3-Amino-6-(4-amino-2,3-dimethylphenylamino)-4-(4-amino-2,3-
dimethyl-phenylimino)-2-propyl-cyclohexa-2,5-dienone Compound 77

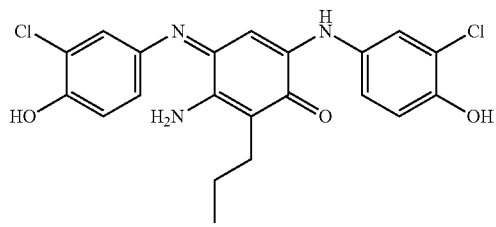

3-Amino-6-(3-chloro-4-hydroxyphenylamino)-4-(3-chloro-4-hydroxy-
phenylimino)-2-propyl-cyclohexa-2,5-dienone Compound 78

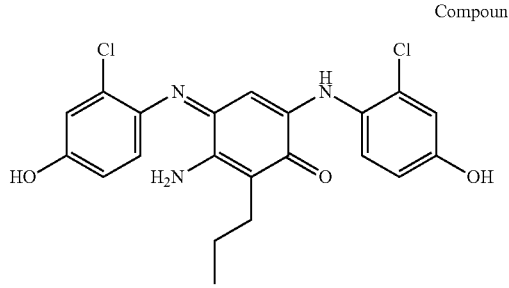

3-Amino-6-(2-chloro-4-hydroxyphenylamino)-4-(2-chloro-4-hydroxy-
phenylimino)-2-propyl-cyclohexa-2,5-dienone Compound 79

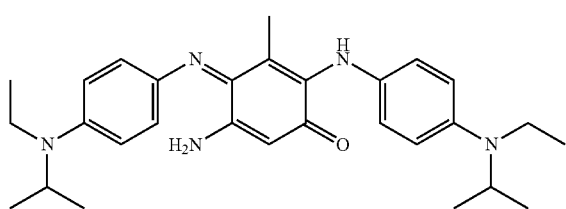

5-Amino-2-[4-(ethyl-isopropylamino)-phenylamino]-4-[4-(ethyl-
isopropylamino)phenylimino]3-methyl-cyclohexa-2,5-dienone Compound 80

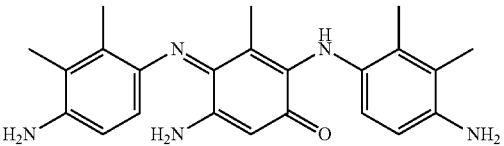

5-Amino-2-(4-amino-2,3-dimethylphenylamino)-4-(4-amino-2,3-dimethyl-
phenylimino)-3-methyl-cyclohexa-2,5-dienone Compound 81

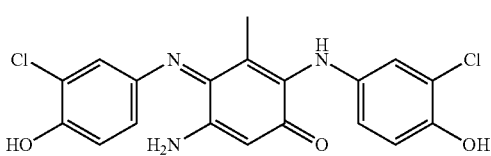

5-Amino-2-(3-chloro-4-hydroxyphenylamino)-4-(3-chloro-4-hydroxy-
phenylimino)-3-methyl-cyclohexa-2,5-dienone Compound 82

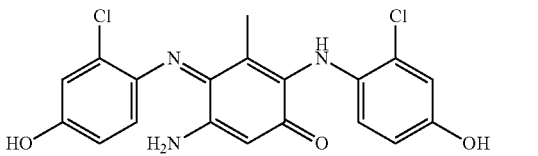

5-Amino-2-(2-chloro-4-hydroxyphenylamino)-4-(2-chloro-4-hydroxy-
phenylimino)-3-methyl-cyclohexa-2,5-dienone Preferably, the direct dyes of formula (I) according to the present invention are selected from azomethine-type compounds 1, 4, 6, 16, 20, 28, 29 and 30.

The direct dyes of formula (I) may be obtained according to the procedure described below:

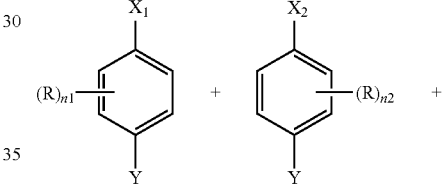

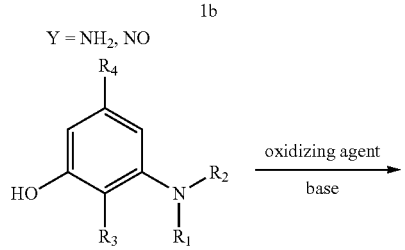

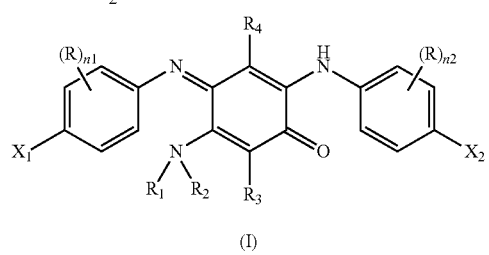

The azomethine-type direct dyes corresponding to formula (I) are generally obtained by reacting derivatives 1a and 1b with meta-aminophenol compounds 2 in a basic medium in the presence of an oxidizing agent. The base used is preferably an aqueous solution of ammonia or of sodium hydroxide and the oxidizing agent is preferably selected from aqueous hydrogen peroxide solution, potassium ferricyanide, air, ammonium persulfate and manganese oxide.

Methods similar to this reaction scheme are described in patent applications FR 2234277, FR 2047932, FR 2106661 and FR 2121101.

In particular, the azomethine-type direct dyes corresponding to formula (I) in which $R_1$ corresponds to a radical of formula (II) may be obtained according to the procedure below:

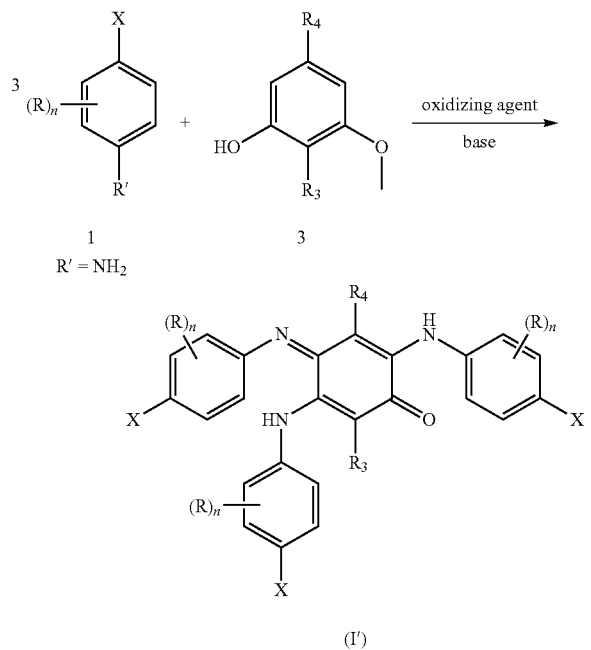

The compounds corresponding to formula (I') are generally obtained by reacting derivatives 1 with meta-methoxyphenols 3 in a basic medium in the presence of an oxidizing agent. The base used is preferably an aqueous solution of ammonia or of sodium hydroxide and the oxidizing agent is preferably selected from aqueous hydrogen peroxide solution, potassium ferricyanide, air, ammonium persulfate and manganese oxide.

II. Dye Composition

As indicated previously, the present invention also relates to a dye composition for keratin fibres, in particular human keratin fibres such as the hair, comprising, in a medium suitable for dyeing, one or more direct dyes of formula (I) as defined previously.

The azomethine-type dyes having a triaromatic unit of formula (I) in the above composition dyeing composition preferably may not also represent the compounds E and F previously mentioned.

Preferably, the dye composition comprises one or more direct dyes of formula (I) selected from azomethine-type compounds 1, 4, 6, 16, 20, 28, 29 and 30 and also mixtures thereof.

The direct dye(s) as defined previously may be present in the dye composition according to the invention in a content ranging from 0.001% to 10% by weight, preferably in a content ranging from 0.005% to 6% by weight, relative to the total weight of the dye composition.

The dye composition according to the invention may also comprise one or more oxidation dyes.

The oxidation dyes are generally selected from oxidation bases optionally combined with one or more couplers.

By way of example, the oxidation bases are selected from para-phenylenediamines, bis(phenyl)alkylenediamines, para-aminophenols, ortho-aminophenols and heterocyclic bases, and the addition salts thereof.

Among the para-phenylenediamines, mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-amino toluene and 3-hydroxy-1-(4'-aminophenyl)pyrrolidine, and addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof.

Among the para-aminophenols, mention may be made, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and the addition salts thereof with an acid.

Among the ortho-aminophenols, mention may be made, by way of example, of 2-aminophenol, 2-amino-5-methylphenol, 2-amino-6-methylphenol, 5-acetamido-2-aminophenol and the addition salts thereof.

Among the heterocyclic bases, mention may be made, by way of example, of pyridine derivatives, pyrimidine derivatives and pyrazole derivatives.

Mention may be made, among pyridine derivatives, of the compounds described, for example, in patents GB 1 026 978 and GB 1 153 196, such as 2,5-diaminopyridine, 2-(4-methoxyphenyl)amino-3-aminopyridine, 3,4-diaminopyridine and the addition salts thereof.

Other pyridine oxidation bases of use in the present invention are the 3-aminopyrazolo[1,5-a]pyridine oxidation bases or the addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof.

Mention may be made, among pyrimidine derivatives, of the compounds described, for example, in patents DE 2359399, JP 63-169571, JP 05-163124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Mention may be made, among pyrazole derivatives, of the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and the addition salts thereof. 4,5-Diamino-1-(β-methoxyethyl)pyrazole may also be used.

Use will preferably be made of a 4,5-diaminopyrazole and more preferably still of 4,5-diamino-1-(β-hydroxyethyl)pyrazole and/or a salt thereof.

Mention may also be made, as pyrazole derivatives, of diamino-N,N-dihydropyrazolopyrazolones and in particular those described in application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or a salt thereof.

The dye composition may optionally comprise one or more couplers advantageously selected from those conventionally used for dyeing keratin fibres.

Among these couplers, mention may especially be made of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2, 6-bis(β-hydroxyethylamino)toluene, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, the addition salts thereof with an acid, and mixtures thereof.

In general, the addition salts of the oxidation bases and couplers which can be used in the context of the invention are selected in particular from the addition salts with an acid, such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight and preferably from 0.005% to 6% by weight relative to the total weight of the composition.

The content of coupler(s), if it is (they are) present, each advantageously represents from 0.001% to 10% by weight relative to the total weight of the composition, and preferably from 0.005% to 6% by weight relative to the total weight of the dye composition.

The dye composition according to the invention may also comprise one or more additional direct dyes other than the azomethine-type direct dyes defined previously.

The additional direct dye(s) according to the invention are selected from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, azomethine direct dyes and natural direct dyes.

Among the benzene direct dyes that can be used according to the invention, mention may be made, in a non-limiting manner, of the following compounds:
1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene; and
1-hydroxy-4-β-hydroxyethylamino-3-nitrobenzene.

Among the azo direct dyes that can be used according to the invention, mention may be made of the cationic azo dyes described in patent applications WO 95/15144, WO-95/01772 and EP-714954, the content of which forms an integral part of the invention.

Among these compounds, mention may be made very particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Colour Index International, 3rd edition: Disperse Red 17, Acid Yellow 9, Acid Black 1, Basic Red 22, Basic Red 76, Basic Red 51, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99 and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-amino ethylaminoanthraquinone;
1,4-bis(β,γ-dihydroxypropylamino)anthraquinone.

Among the azine dyes, mention may be made of the following compounds: Basic Blue 17 and Basic Red 2.

Among the triarylmethane dyes that can be used according to the invention, mention may be made of the following compounds: Basic Green 1, Acid Blue 9, Basic Violet 3, Basic Violet 14, Basic Blue 7, Acid Violet 49, Basic Blue 26 and Acid Blue 7.

Among the azomethine dyes that can be used according to the invention, mention may be made of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinoneimine;
3-N-(3'-chloro-4'-methylamino)phenylureido-6-methyl-1,4-benzoquinoneimine; and
3-[4'-N-(ethyl,carbamylmethyl)amino]phenylureido-6-methyl-1,4-benzoquinoneimine.

Among the natural direct dyes that can be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions containing these natural dyes and in particular henna-based extracts or poultices.

Preferably, the dye composition comprises, in a medium suitable for dyeing, one or more direct dyes of formula (I) and one or more azomethine direct dyes other than the direct dyes of formula (I).

The additional direct dye(s) may be present in the dye composition in a content ranging from 0.001% to 10% by weight, preferably in a content ranging from 0.005% to 6% by weight, relative to the total weight of the composition.

The medium that is suitable for dyeing, also known as the dye support, is a cosmetic medium generally formed from water or a mixture of water and of at least one organic solvent. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

When they are present, the solvents are present in proportions preferably of between 1% and 99% by weight approximately and more preferably still of between 5% and 95% by weight approximately, relative to the total weight of the dye composition.

The dye composition may also contain various adjuvants conventionally used in hair dye compositions, such as anionic, cationic, nonionic or amphoteric surfactants or mixtures thereof, anionic, cationic, nonionic or amphoteric polymers or mixtures thereof, inorganic or organic thickeners, and in particular anionic, cationic, nonionic and amphoteric polymeric associative thickeners, antioxidants, penetrants, sequestrants, solubilizers, fragrances, buffers, dispersants, conditioning agents, for instance volatile or non-volatile, modified or unmodified silicones such as amino silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition in accordance with the invention is generally between 3 and 12 approximately, preferably between 5 and 11 approximately and more particularly still from 6 to 9.5. It may be adjusted to the desired value by means of acidifying or alkalinizing agents customarily used in the dyeing of keratin fibres, or alternatively using standard buffer systems.

Among the acidifying agents, mention may be made, by way of example, of inorganic or organic acids, such as hydrochloric acid, orthophosphoric acid, sulfuric acid, carboxylic acids, such as acetic acid, tartaric acid, citric acid or lactic acid, or sulfonic acids.

Among the alkalinizing agents, mention may be made, by way of example, of aqueous ammonia, alkali metal carbonates, alkanolamines, such as mono-, di- and triethanolamines and derivatives thereof, sodium hydroxide, potassium hydroxide and the compounds of formula (IV) below:

$$\begin{array}{c} R_a \\ \diagdown \\ N-W-N \\ \diagup \\ R_c \end{array} \begin{array}{c} R_b \\ \diagup \\ \diagdown \\ R_d \end{array} \quad (IV)$$

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom, a $C_1$-$C_4$ alkyl radical or a $C_1$-$C_4$ hydroxyalkyl radical.

The dye composition according to the invention may be in various forms, such as in the form of liquids, creams or gels, or in any other form that is suitable for dyeing keratin fibres, and especially human hair.

As indicated previously, the invention also relates to the use of the dye composition as defined previously for colouring keratin fibres, in particular human keratin fibres such as the hair.

III. Use of Azomethine-Type Compounds

Likewise, the present invention consists of the use, for dyeing keratin fibres, in particular human keratin fibres such as the hair, of one or more azomethine-type direct dyes having a triaromatic unit of formula (I) below, the organic or inorganic acid or base salts thereof, the tautomeric, optical isomer or geometric isomer forms thereof and/or the solvates thereof:

(I)

in which formula (I) $n_1$, $n_2$, R, $R_1$, $R_2$, $R_3$, $R_4$, $X_1$ and $X_2$ have the same meanings as those indicated previously.

The compounds A, B, C and D are not used for dyeing keratin fibres.

The compounds E and F may also not be used for dyeing keratin fibres.

IV. Dyeing Method

The dyeing method according to the present invention consists in applying a dye composition as defined previously to the keratin fibres for a time sufficient to obtain the desired coloration, after which the fibres are rinsed, optionally washed with shampoo, rinsed again and the resulting fibres are dried or left to dry.

The dye composition used during the keratin fibre dyeing method does not comprise the compounds A, B, C, D. Preferably, the dye composition used during the method of the present invention may also not comprise the compounds E and F.

Preferably, the leave-on time for the dye composition is between 1 and 60 minutes, preferably between 5 and 40 minutes and more preferably still between 10 and 30 minutes.

The dye composition is generally applied to the keratin fibres at ambient temperature, preferably between 25° C. and 55° C.

According to one embodiment, the dye composition according to the invention is applied to the keratin fibres in the presence of one or more oxidizing agents for a time that is sufficient to obtain the desired lightening.

The oxidizing agent may be present in the dye composition or may be used separately in a cosmetic composition.

Preferably, the oxidizing agent is used separately in a cosmetic composition.

Thus, the present invention also relates to a method for lightening keratin fibres, in particular human keratin fibres such as the hair, in which applied to said fibres are (i) the dye composition as defined previously free of oxidizing agent and (ii) a cosmetic composition comprising one or more oxidizing agents; compositions (i) and (ii) being applied to said keratin fibres sequentially or simultaneously for a time sufficient to obtain the desired lightening, after which the fibres are rinsed, optionally washed with shampoo, rinsed again and the resulting fibres are dried or left to dry.

For the purposes of the present invention, the term "sequentially" means that the oxidizing composition is applied before or after the dye composition, i.e. as a pre-treatment or a post-treatment.

The oxidizing agents used are selected from hydrogen peroxide, urea peroxide, alkali metal bromates, persalts such as perborates and persulfates, peracids and oxidase enzymes (with the possible cofactors thereof), among which mention may be made of peroxidases, 2-electron oxidoreductases such as uricases, and 4-electron oxygenases, for instance laccases.

The oxidizing agent is preferably hydrogen peroxide.

The oxidizing composition may also contain various adjuvants conventionally used in compositions for dyeing the hair and as defined previously.

The pH of the oxidizing composition containing the oxidizing agent is such that, after mixing with the dye composition, the pH of the resulting composition applied to the keratin fibres preferably ranges between 3 and 12 approximately, and more preferably still between 5 and 11 and more particularly still between 6 and 9.5. It may be adjusted to the desired value by means of acidifying or alkalinizing agents usually used in the dyeing of keratin fibres and as defined previously.

V. Leuco-Type Compound

Furthermore, the present invention relates to leuco-type compounds of formula (III) below, the organic or inorganic acid or base salts thereof, the tautomeric, optical isomer or geometric isomer forms thereof and/or the solvates thereof:

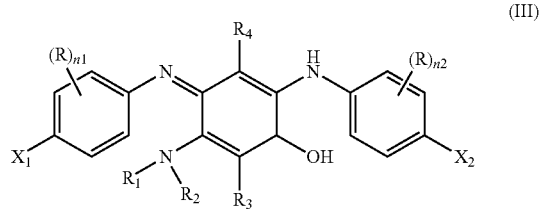

(III)

in which formula (III) $n_1$, $n_2$, R, $R_1$, $R_2$, $R_3$, $R_4$, $X_1$ and $X_2$ have the same meanings as those indicated in formula (I).

In particular, the preferred variants of $n_1$, $n_2$, R, $R_1$, $R_2$, $R_3$, $R_4$, $X_1$ and $X_2$ in formula (III) for the leuco-type compounds correspond to those indicated in formula (I) for the direct dyes.

The leuco-type compounds corresponding to formula (III) are generally obtained by reacting the azomethine-type compounds of formula (I) with a reducing agent according to the reaction scheme below:

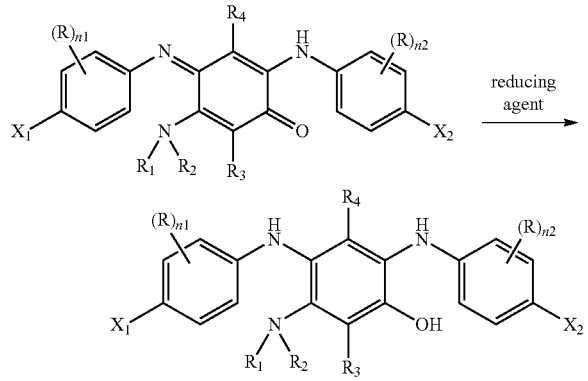

Synthesis approaches similar to this reaction scheme are described in patent applications FR 2 056 799, FR 2 047 932, FR 2 165 965 and FR 2 262 023.

The leuco-type compounds of formula (III) are used as precursors of direct dyes of formula (I).

Preferably, the leuco-type compounds of formula (III) are selected from the compounds corresponding to the reduced form of the azomethine-type direct dyes 1 to 82 mentioned previously.

In other words, the leuco-type compounds of formula (III) are selected from the precursors of azomethine-type direct dyes 1 to 82.

More preferably still, the leuco-type compounds of formula (III) are selected from the precursors of direct dyes 1, 4, 6, 16, 20, 28, 29 and 30.

In particular, the invention relates to a cosmetic composition comprising one or more leuco-type compounds of formula (III) as defined previously.

The present invention also relates to a dyeing method in which a cosmetic composition comprising one or more leuco-type compounds of the abovementioned formula (III) are applied to keratin fibres in the presence of one or more oxidizing agents for a time that is sufficient to develop the desired coloration, after which the fibres are rinsed, optionally washed with shampoo, rinsed again, and the resulting fibres are dried or left to dry.

The oxidizing agent may be atmospheric oxygen or may be selected from the aforementioned oxidizing agents.

In particular, when the oxidizing agent is atmospheric oxygen, simply exposing the keratin fibres treated with the composition comprising the leuco-type compound(s) to air makes it possible to generate the colouring species and, consequently, to colour the fibres.

According to one variant, the oxidizing agent(s) may be applied to the keratin fibres simultaneously with or sequentially to the cosmetic composition comprising the leuco-type compounds.

Thus, the cosmetic composition comprising the oxidizing agent(s) may be applied to the keratin fibres before, simultaneously with or after the cosmetic composition comprising the leuco-type compounds of formula (III) according to the invention.

According to another variant, a ready-to-use composition that results from the mixing of a cosmetic composition comprising one or more leuco-type compounds of the aforementioned formula (III) and of a cosmetic composition comprising one or more oxidizing agents is applied to keratin fibres.

The ready-to-use composition which is thus applied to the keratin fibres may be in a variety of forms, such as in the form of liquids, creams or gels or in any other form appropriate for dyeing keratin fibres, and in particular human hair.

The leave-on time of the composition(s) varies from 1 to 60 minutes, preferably from 5 to 40 minutes and more preferably from 10 to 30 minutes.

The cosmetic composition comprising such leuco-type compounds is generally applied to the keratin fibres at ambient temperature, preferably between 25° C. and 55° C.

Thus, the present invention also relates to a cosmetic composition, in particular for dyeing keratin fibres such as the hair, comprising one or more compounds of formula (III) as defined previously and optionally comprising one or more oxidizing agents.

VI. Dyeing Device

The present invention also relates to a multicompartment device or "kit" comprising a first compartment containing a cosmetic composition comprising one or more dyes of formula (I) as defined previously or containing one or more leuco-type compounds of formula (III) as defined previously, and optionally a second compartment comprising one or more oxidizing agents.

In particular, the invention relates to a multicompartment dyeing device or kit comprising a first compartment containing a cosmetic composition comprising one or more direct dyes of formula (I) as defined previously or containing one or more leuco-type compounds of formula (III) as defined previously, and a second compartment comprising one or more oxidizing agents.

More particularly, the invention relates to a multicompartment dyeing device or kit comprising a first compartment containing a cosmetic composition comprising one or more direct dyes of the aforementioned formula (I) free of oxidizing agent and a second compartment containing a cosmetic composition comprising one or more oxidizing agents.

The invention also relates to a multicompartment dyeing device or kit comprising a first compartment containing a cosmetic composition comprising one or more leuco-type compounds of the aforementioned formula (III), and a second compartment containing a cosmetic composition comprising one or more oxidizing agents.

According to one particular embodiment, the device may comprise at least one compartment comprising a cosmetic composition comprising one or more leuco-type compounds of the aforementioned formula (III).

In this case, the composition comprising the leuco-type compound(s) as defined above is applied to the keratin fibres that are coloured by means of the exposure thereof to air.

The devices mentioned above are suitable for dyeing keratin fibres.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis. The lower the value of L, the darker or more intense the color is. The higher the value of a*, the redder the shade is; the higher the value of b*, the yellower the shade is.

The variation in coloring between the colored locks of natural white hair which is untreated (control) and after treatment or coloration is defined by ΔE*, corresponding to the colour uptake on keratin fibers, according to the following equation:

$$\Delta E^* = \sqrt{(L^* - L_0^*)^2 + (a^* - a_0^*)^2 + (b^* - b_0^*)^2} \quad (i)$$

In this equation, L*, a* and b* represent the values measured after dyeing the natural hair comprising 90% of white hairs and $L_0^*$, $a_0^*$ and $b_0^*$ represent the values measured for the untreated natural hair comprising 90% of white hairs.

The greater the value of ΔE, the greater the difference in color between the control locks and the dyed locks and the greater color uptake is. Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLES

I. Synthesis Examples

Example 1

Synthesis of 2-[4-(ethylisopropylamino)phenylamino]-4-[4-(ethylisopropylamino)phenylimino]-5-methylamino-cyclohexa-2,5-dienone (compound 1)

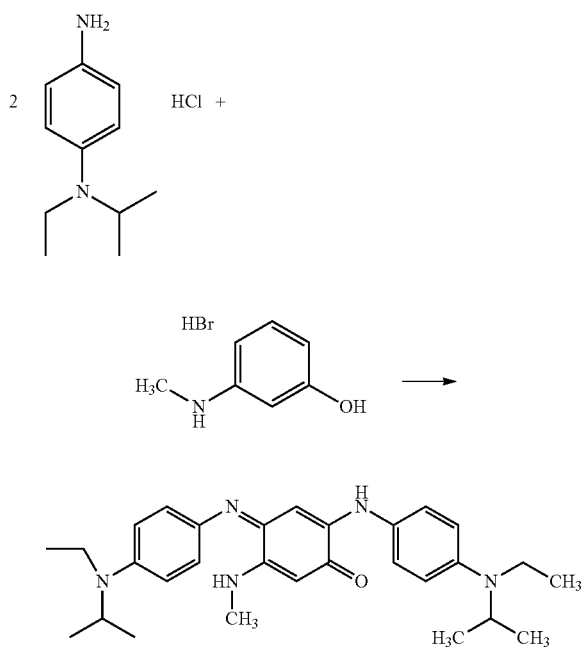

Compound 1

Added to a solution of 0.85 g (0.004 mol) of N-(4-aminophenyl)-N-ethyl-N-isopropylamine hydrochloride in 2 ml of water and 2 ml of ethanol, is a solution of 0.40 g (0.002 mol) of 3-(methylamino)phenol hydrobromide in 1 ml of water and 2 ml of ethanol. The pH is adjusted to 9.5 with 2 ml of 20% aqueous ammonia. 7 ml of 6% aqueous hydrogen peroxide solution are added and the mixture is stirred for 24 hours. A solid is formed; after filtration, it is washed with water and then with a water/methanol mixture. The product is purified on a silica column (eluent: dichloromethane/methanol 95/5).

0.24 g of black powder of 2-[4-(ethylisopropylamino)-phenylamino]-4-[4-(ethylisopropylamino)phenylimino]-5-methylamino-cyclohexa-2,5-dienone (compound 1) is obtained.

The molecular ion 474 (ES+) is detected by mass spectrometry.

Example 2

Synthesis of 2-[4-(ethylisopropylamino)phenylamino]-4-[4-(ethylisopropylamino)phenylimino]-5-(2-hydroxyethylamino)cyclohexa-2,5-dienone (compound 4)

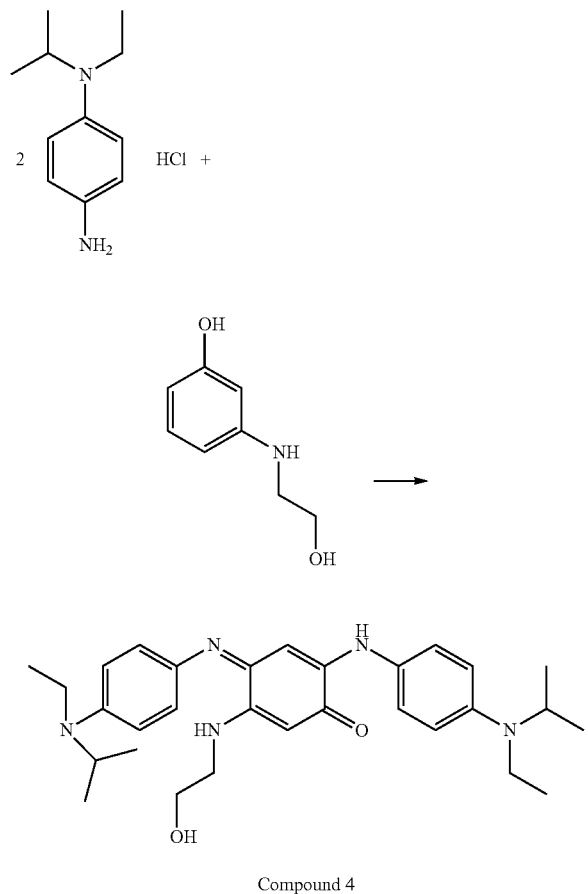 [SMILES: CCN(c1ccc(N)cc1)C(C)C ; Cl ; OCCNc1cccc(O)c1 ; CCN(c1ccc(/N=C2/C=C(Nc3ccc(N(CC)C(C)C)cc3)C(=O)C=C2NCCO)cc1)C(C)C]

Compound 4

Added to a solution of 0.42 g (0.002 mol) of N-(4-aminophenyl)-N-ethyl-N-isopropylamine hydrochloride in 2 ml of water and 2 ml of ethanol, is a solution of 0.15 g (0.001 mol) of 3-[(2-hydroxyethyl)amino]phenol. The pH is adjusted to 9.5 with 2 ml of 20% aqueous ammonia. 7 ml of 6% aqueous hydrogen peroxide solution are added and the mixture is stirred for 5 hours at ambient temperature.

The precipitate formed is filtered off, rinsed with water and dried. Thus, 80 mg of a black powder corresponding to 2-[4-(ethylisopropylamino)phenylamino]-4-[4-(ethylisopropylamino)phenylimino]-5-(2-hydroxyethylamino)cyclohexa-2,5-dienone (compound 4) are obtained.

The molecular ion 504 (ES+) is detected by mass spectrometry.

Example 3

Synthesis of 5-dimethylamino-2-[4-(ethylisopropylamino)phenylamino]-4-[4-(ethylisopropylamino)phenylimino]-cyclohexa-2,5-dienone (compound 6)

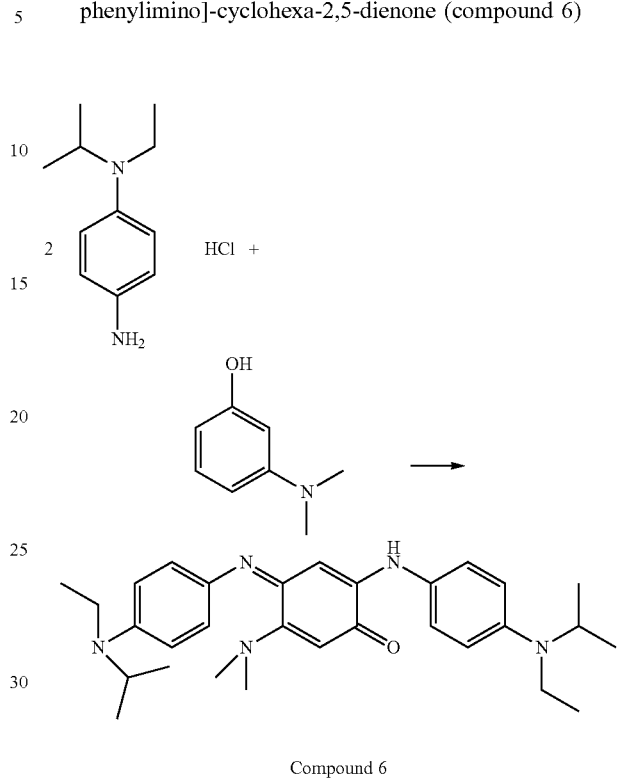

Compound 6

Added to a solution of 0.53 g (0.003 mol) of N-(4-aminophenyl)-N-ethyl-N-isopropylamine hydrochloride in 2 ml of water and 2 ml of ethanol, is 0.41 g (0.003 mol) of 3-(dimethylamino)phenol. The pH is adjusted to 9.5 with 1.5 ml of 20% aqueous ammonia. 1 ml of 6% aqueous hydrogen peroxide solution is added and the mixture is stirred for 48 hours. The solid formed is filtered off and then purified by chromatography (eluent: dichloromethane/methanol 99/1).

250 mg of brown powder corresponding to 5-dimethylamino-2-[4-(ethylisopropylamino)phenylamino]-4-[4-(ethylisopropylamino)phenylimino]cyclohexa-2,5-dienone (compound 6) are obtained.

The molecular ion 489 (ES+) is detected by mass spectrometry.

Example 4

Synthesis of 3,6-bis[4-(ethylisopropylamino)phenylamino]-4-[4-(ethylisopropylamino)phenylimino]-2-methoxycyclohexa-2,5-dienone (compound 28)

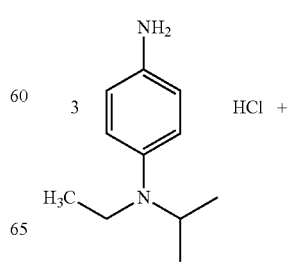

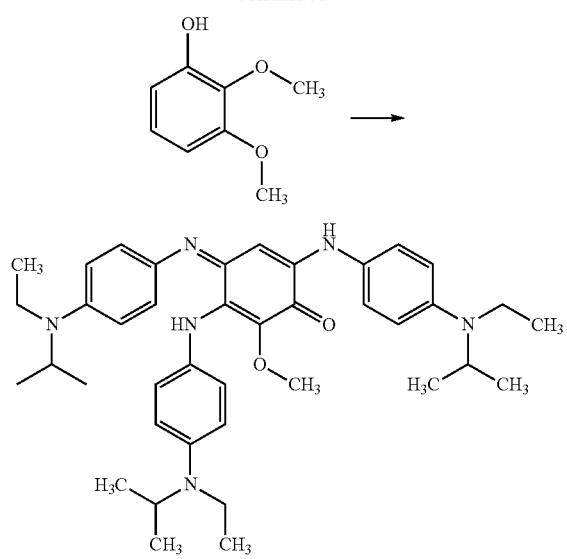

Compound 28

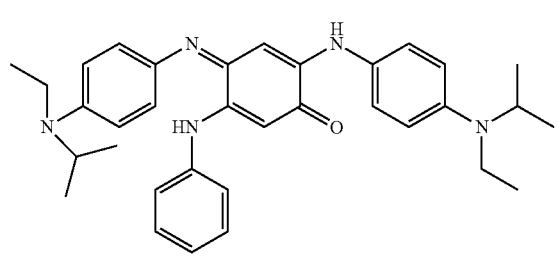

Compound 29

Added to a solution of 0.64 g (0.003 mol) of N-(4-aminophenyl)-N-ethyl-N-isopropylamine hydrochloride in 2 ml of water and 3 ml of ethanol, is a solution of 0.47 g (0.003 mol) of 2,3-dimethoxyphenol in 1 ml of water and 3 ml of ethanol. The pH is adjusted to 9.5 with 1.5 ml of 20% aqueous ammonia. 10.5 ml of 6% aqueous hydrogen peroxide solution are added and the mixture is stirred for 5 hours 30 minutes. The product is extracted with dichloromethane. The organic phase is dried with disodium sulfate, filtered and then concentrated until the solvents are eliminated. The product obtained is purified by chromatography (eluent: dichloromethane/methanol 95/5).

0.12 g of black product corresponding to 3,6-bis[4-(ethylisopropylamino)phenylamino]-4-[4-(ethylisopropylamino)phenylimino]-2-methoxycyclohexa-2,5-dienone (compound 28) is obtained.

The molecular ion 651 (ES+) is detected by mass spectrometry. The $^1$H NMR spectrum is in agreement.

Example 5

Synthesis of 2-[4-(ethylisopropylamino)phenylamino]-4-[4-(ethylisopropylamino)phenylimino]-5-phenylaminocyclohexa-2,5-dienone (compound 29)

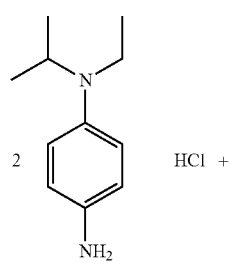

Added to a solution of 1.1 g (0.005 mol) of N-(4-aminophenyl)-N-ethyl-N-isopropylamine hydrochloride in 5 ml of water and 5 ml of ethanol, is 0.93 g (0.005 mol) of 3-hydroxydiphenylamine. The pH is adjusted to 9.5 with 20% aqueous ammonia. 17 ml of 6% aqueous hydrogen peroxide solution is added and the mixture is stirred for 48 hours. The gum formed is washed with water and then purified by chromatography (eluent: dichloromethane).

211 mg of brown powder corresponding to 2-[4-(ethylisopropylamino)phenylamino]-4-[4-(ethylisopropylamino)phenylimino]-5-phenylaminocyclohexa-2,5-dienone (compound 29) are obtained.

The molecular ion 535 (ES+) is detected by mass spectrometry.

Example 6

Synthesis of 2-{4-[ethyl-(2-hydroxyethyl)amino]-2-methylphenylamino}-4-{4-[ethyl-(2-hydroxyethyl)amino]-2-methyl-phenylimino}-5-phenylaminocyclohexa-2,5-dienone (compound 30)

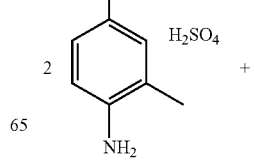

-continued

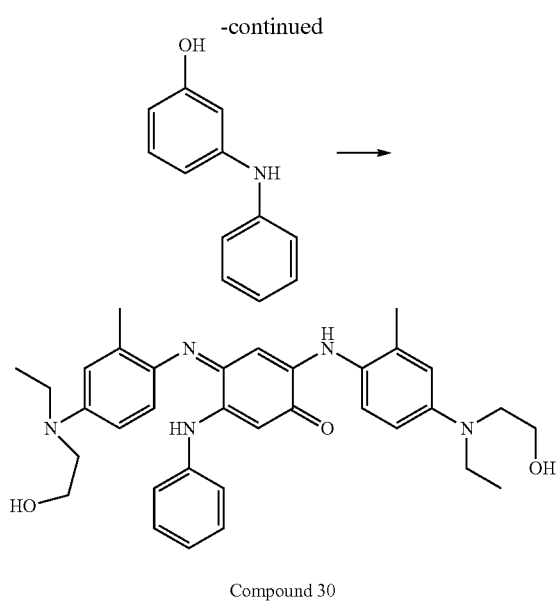

Compound 30

Added to a solution of 4.39 g (0.015 mol) of 2-[(4-amino-3-methylphenyl)(ethyl)amino]ethanol sulfate in 10 ml of water and 30 ml of ethanol, are 2.78 g (0.015 mol) of 3-hydroxydiphenylamine. The pH is adjusted to 9.5 with 20% aqueous ammonia. 25.5 ml of 6% aqueous hydrogen peroxide solution are added and the mixture is stirred for 24 hours. The gum formed is washed with water and then purified by chromatography (eluent: dichloromethane/methanol 9/1). 802 mg of brown powder corresponding to 2-{4-[ethyl-(2-hydroxyethyl)amino]-2-methylphenylamino}-4-{4-[ethyl-(2-hydroxyethyl)amino]-2-methylphenylimino}-5-phenylaminocyclohexa-2,5-dienone (compound 30) are obtained.

The molecular ion 568 (ES+) is detected by mass spectrometry.

Example 7

Synthesis of 5-amino-2-[(4-amino-2,3-dimethylphenyl)amino]-4-[(4-amino-2,3-dimethylphenyl)imino]cyclohexa-2,5-dien-1-one (compound 20)

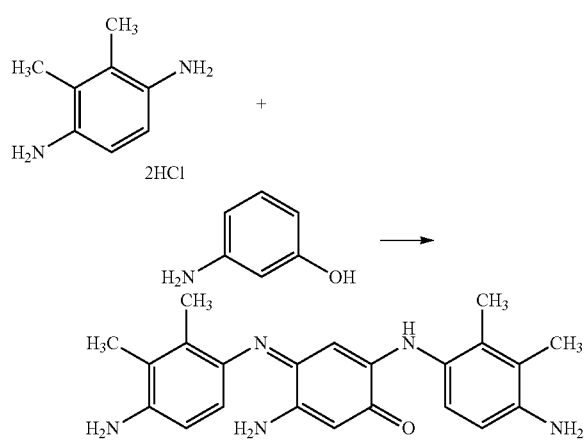

Added to a solution of 3.14 g (0.015 mol) of 2,3-dimethylbenzene-1,4-diamine and 0.817 g (0.075 mol) of 3-aminophenol in 10 mL of water and 20 mL of ethanol whose the pH were adjusted to 9.5 with 20% aqueous ammonia, are 4.25 mL of 30% (0.0375 mol) aqueous hydrogen peroxide. The mixture is stirred for 24 hours. The precipitate formed is filtered off.

The solid is then dissolved in 10 mL of dimethylsulfoxyde, the obtained solution is filtered and 15 mL of water is added to the filtrate.

The precipitate formed once again is filtrated and is washed with 8 mL of a mixture of dimethylsulfoxyde/water (50/50) and 100 mL of water. The product is purified by silica chromatography (eluent dichloromethane/methanol 98/2).

804 mg of black powder corresponding to 5-amino-2-[(4-amino-2,3-dimethylphenyl)amino]-4-[(4-amino-2,3-dimethylphenyl)imino]cyclohexa-2,5-dien-1-one (compound 20) are obtained.

The molecular ion 376 (ES+) is detected by mass spectrometry.

Example 8

Synthesis of 5-amino-2-({4-[ethyl(propan-2-yl)amino]phenyl}amino)-4-({4-[ethyl(propan-2-yl)amino]phenyl}imino)cyclohexa-2,5-dien-1-one (compound 16)

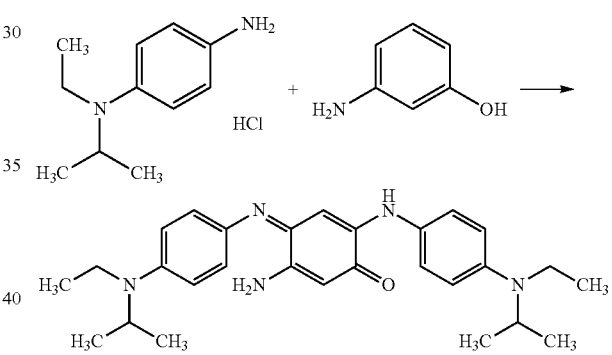

Added to a solution of 6.44 g (0.03 mol) of N-(4-aminophenyl)-N-ethyl-N-isopropylamine and 1.65 g (0.015 mol) of 3-aminophenol in 20 mL of water and 40 mL of ethanol brought to pH 9.5 with 20% aqueous ammonia, are 15 mL of 30% aqueous hydrogen peroxide. The mixture is stirred for 10 hours. A gum is formed.

After decantation of the supernatant, the gum is washed with 20 mL of water/ethanol 50/50 mixture and the gum is added to methanol. The product crystallized for two days.

The product obtained is purified by silica chromatography (eluent dichloromethane/methanol 98/2). 1.8 g of black powder corresponding 5-amino-2-({4-[ethyl(propan-2-yl)amino]phenyl}amino)-4-({4-[ethyl(propan-2-yl)amino]phenyl}imino)cyclohexa-2,5-dien-1-one (compound 16) are obtained.

The molecular ion 460 (ES+) is detected by mass spectrometry

II. Dyeing Evaluations of the Compounds Synthesized

The following dye compositions were prepared:
500 mg of exemplified compound,
79 grams of water, 15 grams of ethanol,
5 grams of benzyl alcohol,
0.5 gram of benzoic acid.

1 gram of the mixture is applied to a 0.25 gram lock of grey hair containing 90% white hairs. After a leave-on time of 30 minutes, the lock is rinsed, washed with a standard shampoo, then rinsed again and then dried.

The results are collated in the following table:

| | |
|---|---|
| Compound 1 | Medium orange-grey |
| Compound 4 | Light orange-grey |
| Compound 6 | Medium orange-grey |
| Compound 28 | Medium orange-grey |
| Compound 29 | Medium orange-grey |
| Compound 30 | Medium orange-grey |

The invention claimed is:

1. Azomethine-type compound having a triaromatic unit of formula (I) below, the organic or inorganic acid or base salts thereof, the tautomeric, optical isomer or geometric isomer forms thereof and/or the solvates thereof:

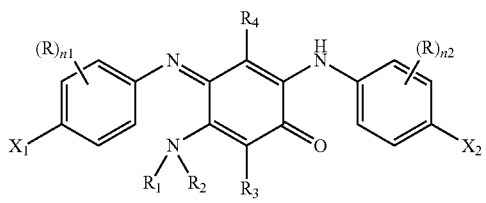

(I)

wherein:
  $n_1$ and $n_2$ represent, independently of one another, an integer equal to 0, 1, 2, 3 or 4;
  R represents:
    a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;
    a $C_1$-$C_4$ alkoxy radical;
    a halogen atom;
  $R_1$ represents:
    a hydrogen atom;
    a linear or branched $C_1$-$C_8$ alkyl radical, optionally substituted with one or more hydroxyl radicals;
    an aminocarbonyl radical;
    a radical of formula (II):

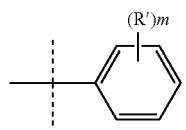

(II)

in which formula (II):
  m represents an integer equal to 0, 1, 2, 3 or 4;
  R' represents:
    a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;
    a $C_1$-$C_4$ alkoxy radical;
    a halogen atom;
    a hydroxyl radical;
    an —NR'₃R'₄ radical in which R'₃ and R'₄ represent, independently of one another:
      a hydrogen atom;
      a linear or branched $C_1$-$C_5$ alkyl radical, optionally substituted with one or more hydroxyl or $C_1$-$C_4$ alkoxy radicals;
    it being understood that, in formula (II), when m is greater than or equal to 2, the R' radicals may be identical or different;
  $R_2$ represents:
    a hydrogen atom;
    a $C_1$-$C_8$ alkyl radical, optionally substituted with one or more hydroxyl radicals;
  $R_1$ and $R_2$ may form, together with the nitrogen atom to which they are attached, a pyrrolidine, piperidine or morpholine ring;
  $R_3$ and $R_4$ represent, independently of one another:
    a hydrogen atom;
    a linear or branched $C_1$-$C_8$ alkyl radical, optionally substituted with one or more hydroxyl radicals;
    a $C_1$-$C_4$ alkoxy radical;
  $X_1$ and $X_2$ represent, independently of one another:
    a hydroxyl radical;
    an —NR"₃R"₄ radical in which:
      R"₃ represents:
        a hydrogen atom;
        a linear $C_1$-$C_6$ alkyl radical;
      R"₄ represents:
        a hydrogen atom;
        a linear or branched $C_3$-$C_6$ alkyl radical;
        a linear or branched $C_2$-$C_6$ alkyl radical substituted with one or more hydroxyl radicals;
  R"₃ and R"₄ may form, together with the nitrogen atom to which they are attached, a piperidino or morpholino ring;
it being understood that the compounds of formula (I) may not represent the compounds A to F below:

Compound A

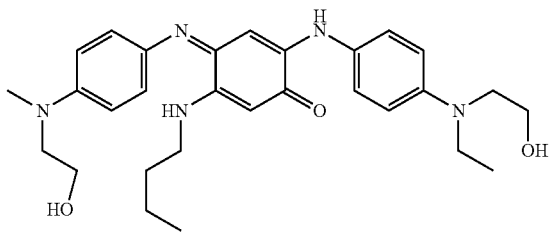

Compound B

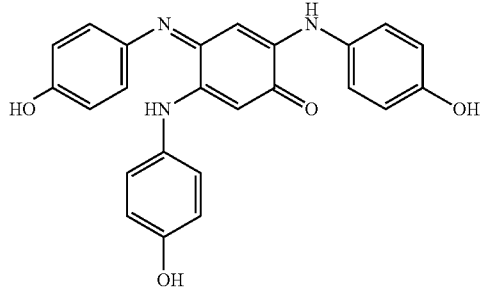

-continued

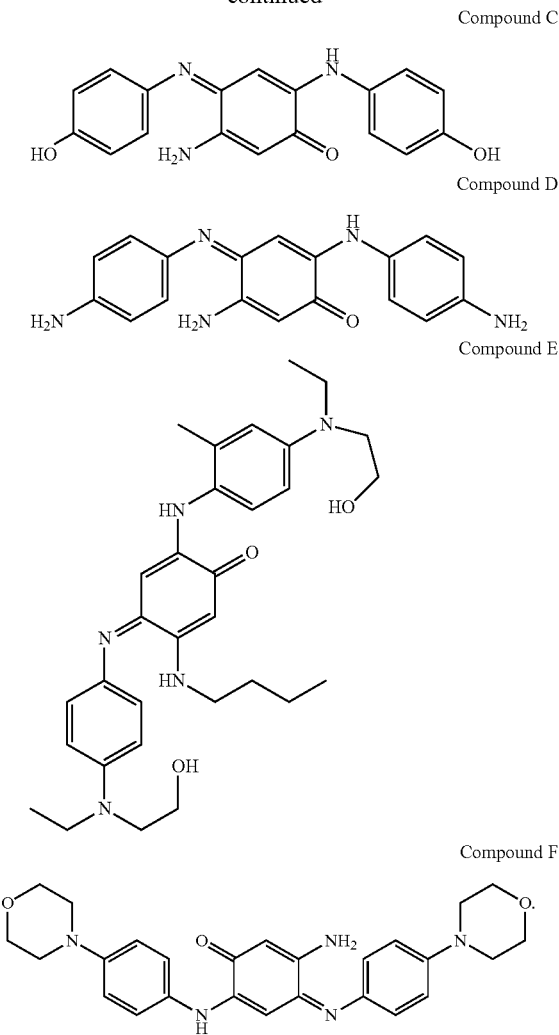

2. Azomethine-type compound having a triaromatic unit of formula (I) according to claim 1, wherein, taken together or separately:
$n_1$ and $n_2$ represent, independently of one another, an integer equal to 0, 1 or 2;
R represents:
a linear or branched $C_1$-$C_4$ alkyl radical;
a $C_1$-$C_4$ alkoxy radical;
a halogen atom;
$R_1$ represents:
a hydrogen atom;
a linear or branched $C_1$-$C_8$ alkyl radical, optionally substituted with one or more hydroxyl radicals;
an aminocarbonyl radical;
a radical of formula (II):

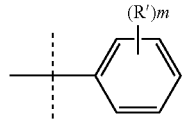

in which formula (II):
m represents an integer equal to 0, 1, 2 or 3;
R' represents:
a linear or branched $C_1$-$C_4$ alkyl radical;
a $C_1$-$C_4$ alkoxy radical;
a halogen atom;
a hydroxyl radical;
an —$NR'_3R'_4$ radical in which $R'_3$ and $R'_4$ represent, independently of one another:
a hydrogen atom;
a linear or branched $C_1$-$C_5$ alkyl radical, optionally substituted with one or more hydroxyl radicals;
it being understood that, in formula (II), when m is greater than or equal to 2, the R' radicals may be identical or different;
$R_2$ represents:
a hydrogen atom;
a linear or branched $C_1$-$C_6$ alkyl radical, a butyl, methyl or ethyl radical;
$R_1$ and $R_2$ may form, together with the nitrogen atom to which they are attached, a pyrrolidine, piperidine or morpholine ring;
$R_3$ and $R_4$ represent, independently of one another:
a hydrogen atom;
a linear or branched $C_1$-$C_8$ alkyl radical;
a $C_1$-$C_4$ alkoxy radical;
and/or
$X_1$ and $X_2$ represent, independently of one another:
a hydroxyl radical;
an —$NR''_3R''_4$ radical in which:
—$R''_3$ represents:
a hydrogen atom;
a linear $C_1$-$C_6$ alkyl radical;
—$R''_4$ represents:
a hydrogen atom;
a linear or branched $C_3$-$C_6$ alkyl radical;
a linear or branched $C_2$-$C_6$ alkyl radical substituted with one or more hydroxyl radicals.

3. Azomethine-type compound having a triaromatic unit of formula (I) according to claim 1, wherein $n_1$ and $n_2$ represent an integer equal to 0 or 1, $R_1$ is other than a hydrogen atom, $R_2$ represents a hydrogen atom and $R_4$ represents a hydrogen atom.

4. Azomethine-type compound having a triaromatic unit of formula (I) according to claim 1, wherein $n_1$ and $n_2$ represent an integer equal to 0 or 1, $R_1$ is other than a hydrogen atom, $R_2$ represents a hydrogen atom, $R_4$ represents a hydrogen atom and $X_1$ and $X_2$ represent an —$N'R''_3R''_4$ radical in which $R''_3$ represents a hydrogen atom or a linear $C_1$-$C_3$ alkyl radical and $R''_4$ represents a hydrogen atom or a linear or branched $C_3$-$C_4$ alkyl radical or a $C_2$-$C_4$ alkyl radical substituted with one or more hydroxyl radicals.

5. Azomethine-type compound having a triaromatic unit of formula (I) according to claim 1, wherein $n_1$ and $n_2$ represent an integer equal to 0 or 1, $R_1$ is other than a hydrogen atom, $R_2$ represents a hydrogen atom, $R_4$ represents a hydrogen atom and $X_1$ and $X_2$ represent a hydroxyl radical.

6. Azomthenine-type compound a triaromatic unit of formula (I) according to claim 1, wherein $X_1$ and $X_2$ represent a —$NR''_3R''_4$ radical wherein $R''_3$ and $R''_4$ represent hydrogen atom.

7. Azomethine-type compound a triaromatic unit of formula (I) according to claim 1, wherein $X_1$ and $X_2$ represent a —$NR''_3R''_4$ radical wherein $R''_3$ and $R''_4$ are different from hydrogen atom.

8. Azomethine-type compound having a triaromatic unit of formula (I) according to claim 1, wherein the compound is selected from the following compounds and also the geometric or optical isomer forms thereof, the organic or inorganic acid or base salts thereof, or the solvates thereof, such as the hydrates:

Compound 1

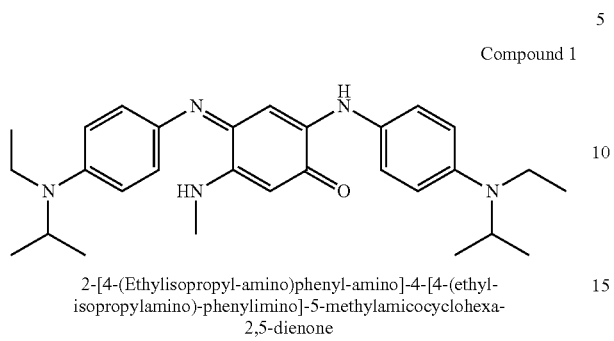

2-[4-(Ethylisopropyl-amino)phenyl-amino]-4-[4-(ethyl-isopropylamino)-phenylimino]-5-methylamicocyclohexa-2,5-dienone Compound 2

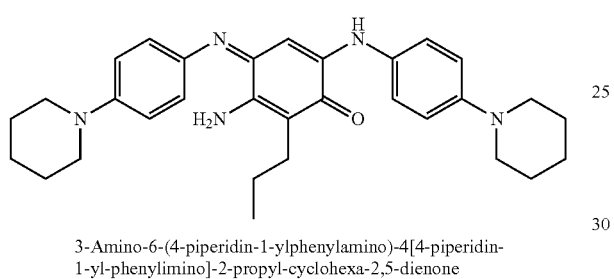

3-Amino-6-(4-piperidin-1-ylphenylamino)-4[4-piperidin-1-yl-phenylimino]-2-propyl-cyclohexa-2,5-dienone Compound 3

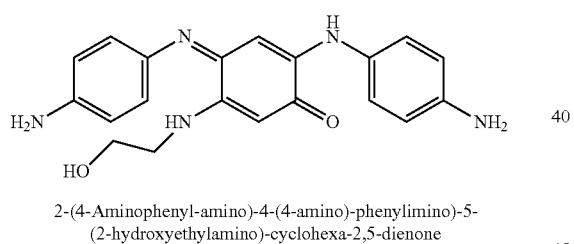

2-(4-Aminophenyl-amino)-4-(4-amino)-phenylimino)-5-(2-hydroxyethylamino)-cyclohexa-2,5-dienone Compound 4

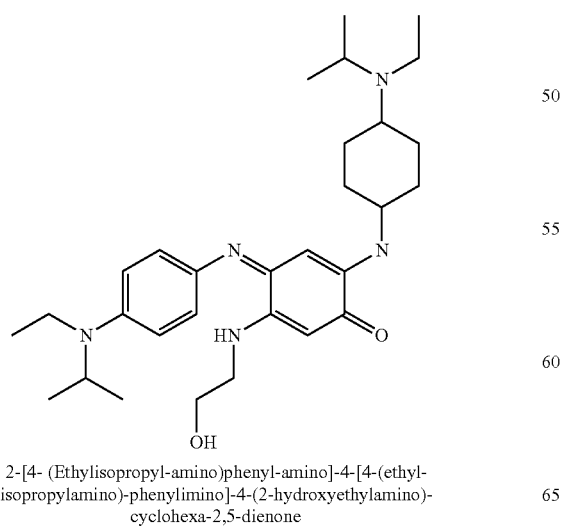

2-[4- (Ethylisopropyl-amino)phenyl-amino]-4-[4-(ethyl-isopropylamino)-phenylimino]-4-(2-hydroxyethylamino)-cyclohexa-2,5-dienone Compound 5

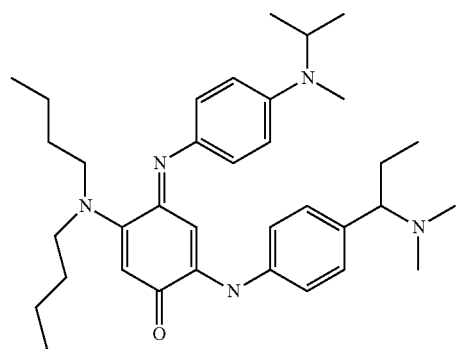

5-Dibutylamino-2-[4-(ethyl-isopropylamino)-phenylamino]-4-[4-(ethylisopropyl-amino)phenylimino]-cyclohexa-2,5-dienone Compound 6

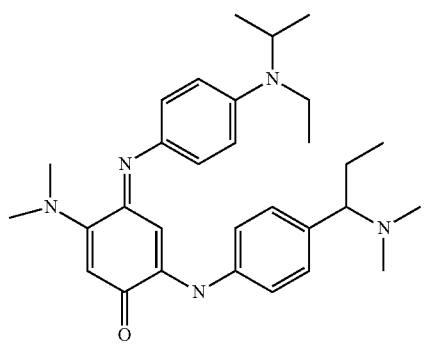

5-Dimethylamino-2-[4-(ethylisopropylamino)-phenylamino]-4-[4-(ethyl-isopropylamino)-phenylamino]cyclohexa-2,5-dienone Compound 7

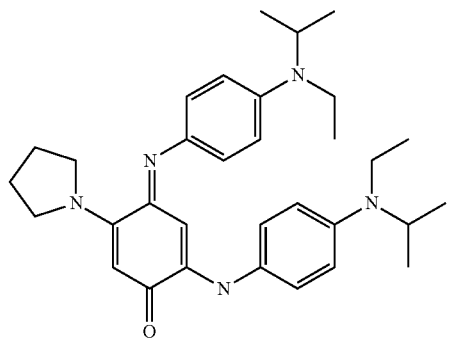

2-[4-(Ethylisopropyl-amino)phenyl-amino]-4-[4-(ethyl-isopropylamino]-5-pyrrolidin-1-yl-cyclohexa-2,5-dienone Compound 8

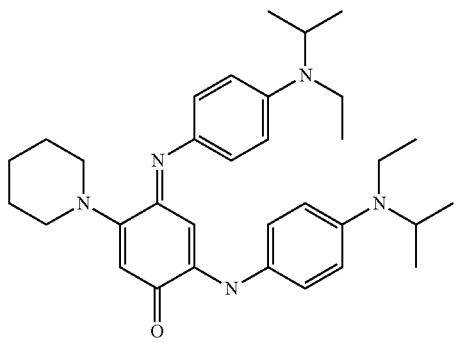

2-[4-(Ethylisopropyl-amino)phenyl-amino]-4-[4-(ethyl-isopropylamino)-phenylimino]-5-piperidin-1-ylcyclohexa-2,5-dienone Compound 9

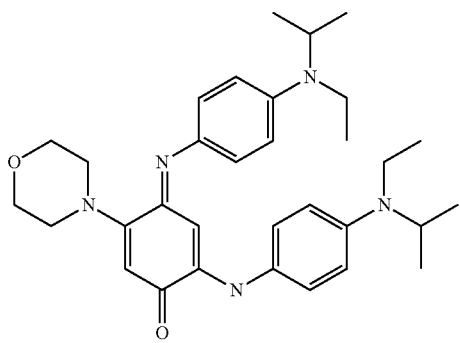

2-[4-(Ethylisopropyl-amino)phenyl-amino]-4-[4-(ethyl-isopropylamino)-phenylimino]-5-morpholin-4-yl-cyclohexa-2,5-dienone Compound 10

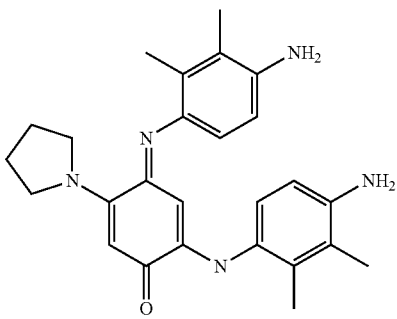

2-(4-Amino-2,3-dimethylphenylamino)-4-(4-amino-2,3-dimethyl-phenylimino)-5-methylaminocyclohexa-2,5-dienone Compound 11

2-(4-Amino-2,3-dimethyl-phenylamino)-4-(4-amino-2,3-diethylphenylimino)-5-pyrrodlidin-1-ylcyclohexa-2,5-dienone Compound 12

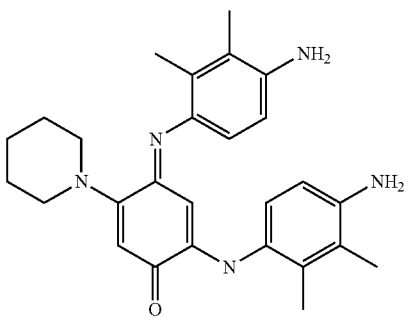

2-(4-Amino-2,3-dimethyl-phenylamino)-4-(4-amino-2,3-dimethylphenylimino)-5-piperidin-1-ylcyclohexa-2,5-dienone Compound 13

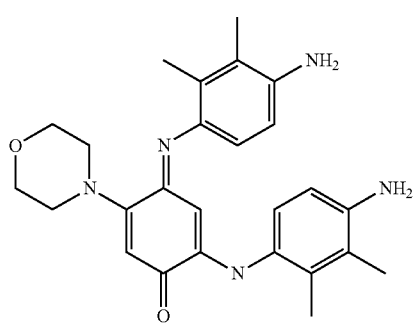

2-(4-Amino-2,3-dimethyl-phenylamino)-4-(4-amino-2,3-dimethylphenylimino)-5-morpholin-4-ylcyclohexa-2,5-dienone Compound 14

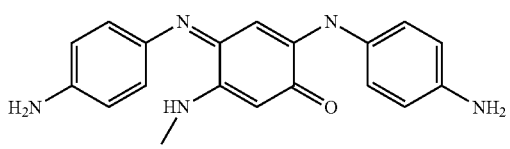

2-(4-Aminophenylamino)-4-(4-amino-phenylimino)-5-methylaminocyclohexa-2,5-dienone Compound 15

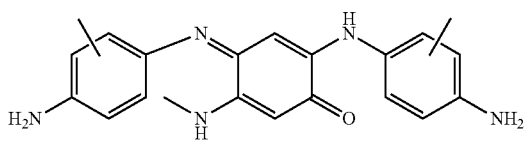

2-(4-Amino-3(or 2)-methyl-phenylamino)-4-(4-amino-3-methylphenylimino)-5-methylaminocyclohexa-2,5-dienone Compound 16

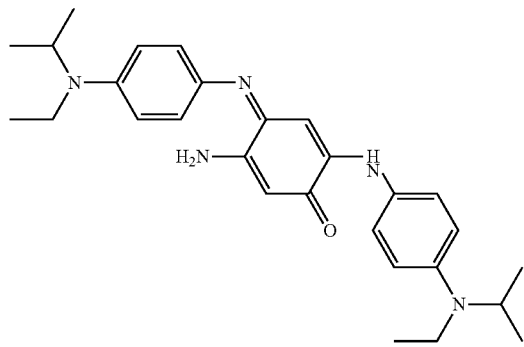

5-Amino-2-[4-(ethylisopropylamino)-phenylamino]-4-[4-(ethyl-isopropylamino)-phenylimino]cyclohexa-2,5-dienone Compound 17

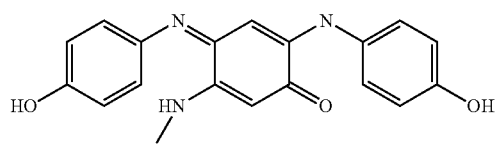

2-(4-Hydroxyphenylamino)-4-(4-hydroxyphenylimino)-5-methylaminocyclohexa-2,5-dienone Compound 18

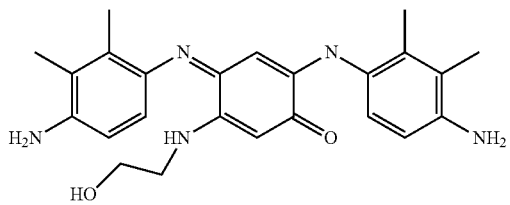

2-(4-Amino-2,3-dimethyl-phenylamino)-4-(4-amino-2,3-dimethylphenylimino)-5-(2-hydroxyethylamino)-cyclohexa-2,5-dienone Compound 19

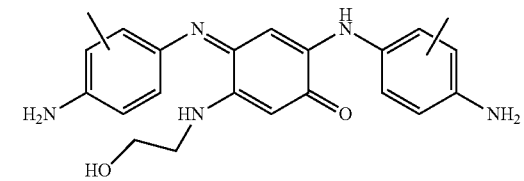

2-(4-Amino-3(or 2)-methylphenylamino)-4-(4-amino-3(or 2)-methylphenylimino)-5-(2-hydroxyethylamino)-cyclohexa-2,5-dienone Compound 20

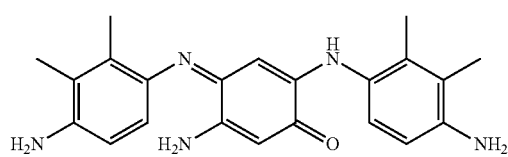

5-Amino-2-(4-amino-2,3-dimethyl-phenylamino)-4-[4-amino-2,3-dimethyl-phenylimino]cyclohexa-2,5-dienone Compound 21

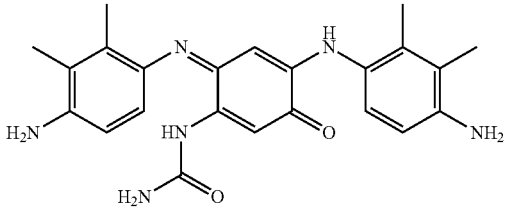

[4-(4-Amino-2,3-dimethylphenylamino)-6-(4-amino-2,3-dimethylphenylimino)-3-oxocyclohexa-1,4-dienyl]urea Compound 22

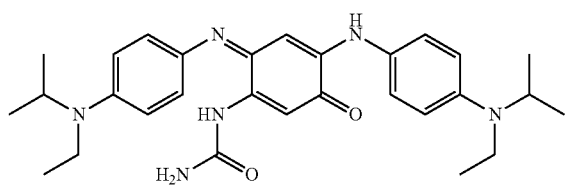

{4-[4-(Ethylisopropyl-amino)phenylamino]-6-[4-(ethylisopropylamino)-phenylimino]-3-oxo-cyclohexa-1,4-dienyl}urea Compound 23

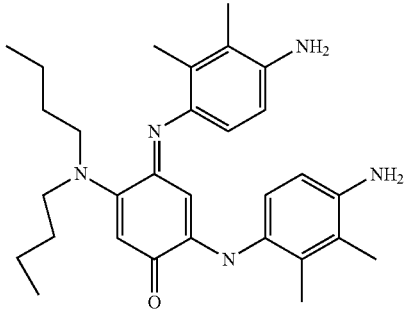

2-(4-Amino-2,3-dimethylphenylamino)-4-(4-amino-2,3-dimethylphenylimino)-5-dibutylamino-cyclohexa-2,5-dienone Compound 24

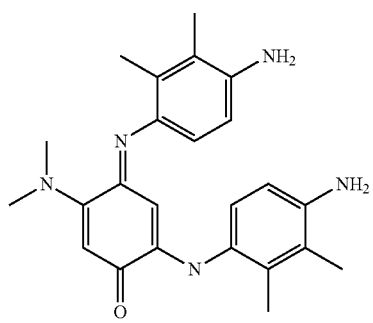

2-(4-Amino-2,3-dimethyl-phenylamino)-4-(4-amino-2,3-dimethylphenylimino)-5-dimethylamino-cyclohexa-2,5-dienone Compound 25

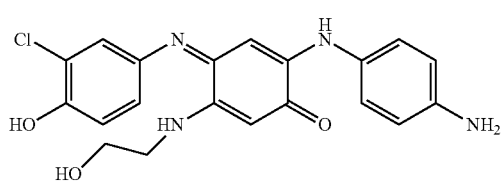

2-(4-Aminophenylamino)-4-(3-chloro-4-hydroxyphenylamino)-cyclhexa-2,5-dienone

Compound 26

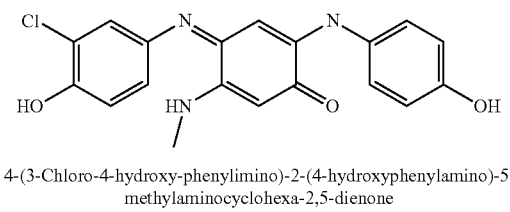

4-(3-Chloro-4-hydroxy-phenylimino)-2-(4-hydroxyphenylamino)-5-methylaminocyclohexa-2,5-dienone Compound 27

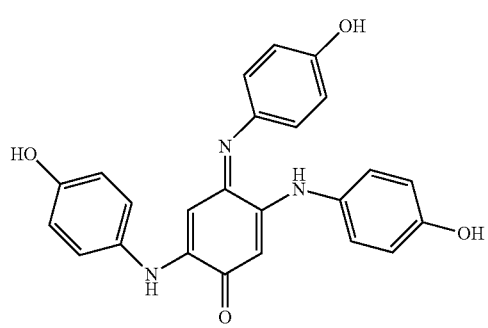

2,5-Bis(4-hydroxy-phenylamino)-4-(4-hydroxy-phenylimino)cyclohexa-2,5-dienone

Compound 28

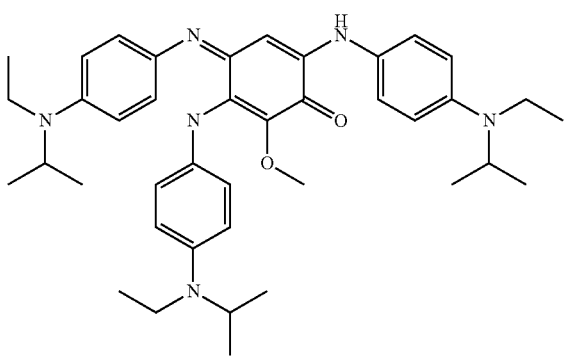

3,6-Bis[4-(ethylisopropyl-amino)-phenylamino]-4-[4-(ethylisopropyl-amino)phenylimino]-2-methoxycyclohexa-2,5-dienone Compound 29

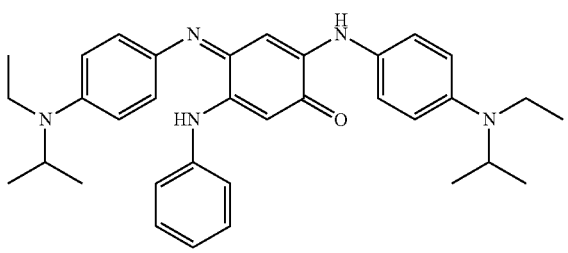

2-[4-Ethylisopropylamino)-phenyl-amino]-4-[4-(ethyl-isopropylamino)-phenylimino]-5-phenylaminocyclohexa-2,5-dienone Compound 30

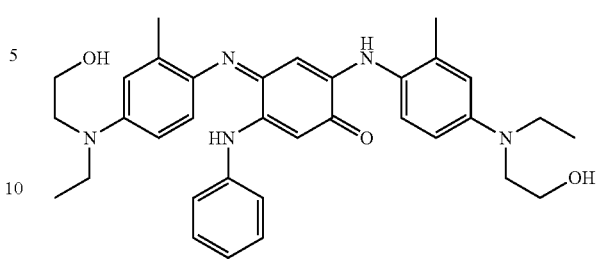

2-{4-[ethyl-(2-hydroxy-ethyl)amino]-2-methyl-phenylamino}-4-{4-[ethyl-(2-hydroxyethyl)amino]-2-methyl-phenylimino}-5-phenylaminocyclohexa-2,5-dienone Compound 31

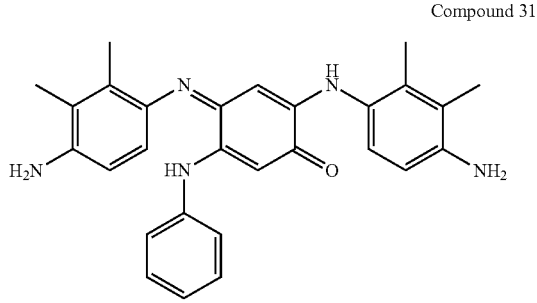

2-(4-Amino-2,3-dimethylphenylamino)-4-(4-amino-2,3-dimethyl-phenylimino)-5-phenylaminocyclohexa-2,5-dienone Compound 32

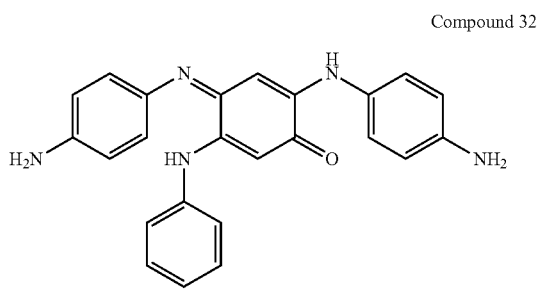

(4-Aminophenylamino)-4-(4-amino-phenylimino)-5-phenylaminocyclohexa-2,5-dienone

Compound 33

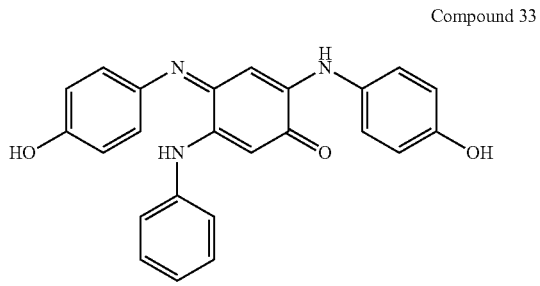

2-(4-Hydroxy-phenylamino)-4-(4-hydroxyphenylimino)-5-phenylaminocyclohexa-2,5-dienone Compound 34

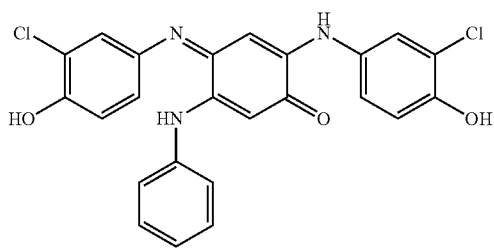

2-(3-Chloro-4-hydroxy-phenylamino)-4-(3-chloro-4-hydroxy-phenylimino)-5-phenylaminocyclohexa-2,5-dienone Compound 35

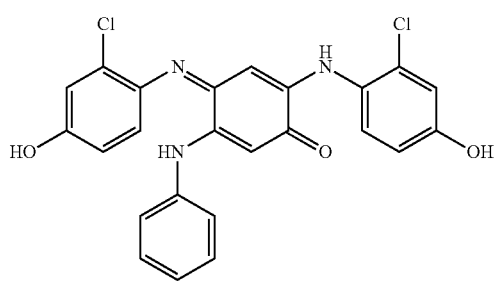

2-(2-Chloro-4-hydroxy-phenylamino)-4-(2-chloro-4-hydroxyphenylimino)-5-phenylaminocyclohexa-2,5-dienone Compound 36

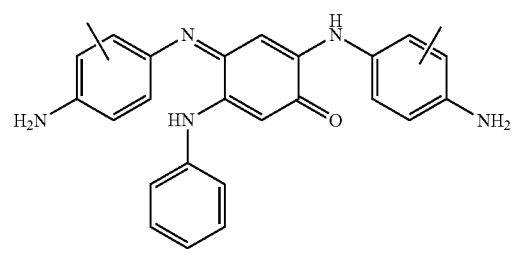

2-(4-Amino-3(or 2)-methyl-phenylamino)-4-(4-amino-3(or 2)-methylphenylimino)-5-phenylaminocyclohexa-2,5-dienone Compound 37

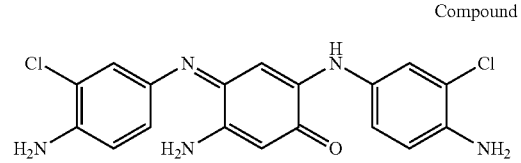

5-Amino-2-(4-amino-3-chloro-phenylamino)-4-[4-amino-3-chlorophenylimino]cyclohexa-2,5-dienone Compound 38

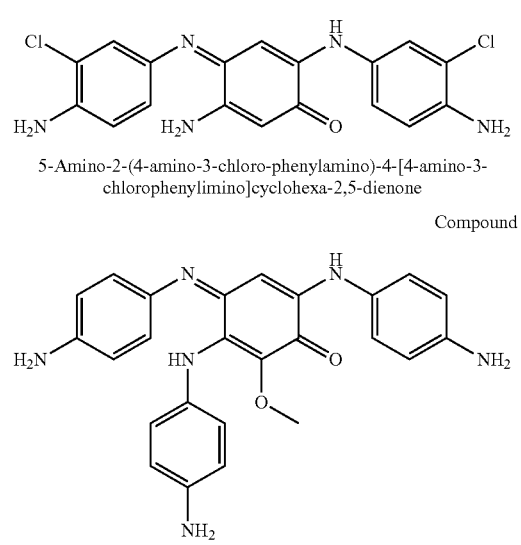

3,6-Bis(4-aminophenylamino)-4-(4-aminophenylimino)-2-methoxycyclohexa-2,5-dienone Compound 39

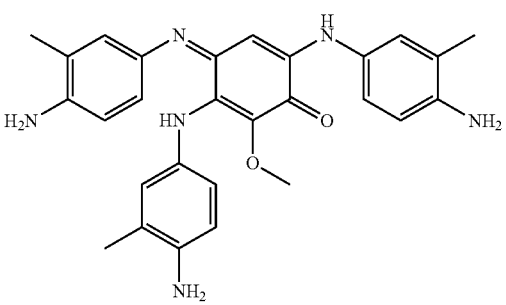

3,6-Bis(4-amino-3-methylphenylamino)-4-(4-amino-3-methyl-phenylimino)-2-methoxy-cyclohexa-2,5-dienone Compound 40

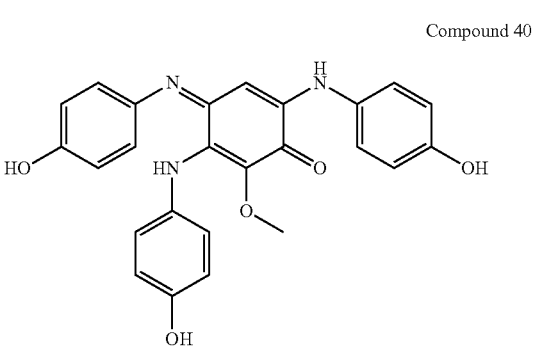

3,6-Bis(4-hydroxy-phenylamino)-4-(4-hydroxyphenylimino)-2-methoxycyclohexa-2,5-dienone Compound 41

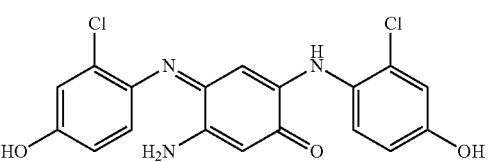

5-Amino-2-(2-chloro-4-hydroxyphenylamino)-4-[2-chloro-4-hydroxy-phenylimino]cyclohexa-2,5-dieonone Compound 42

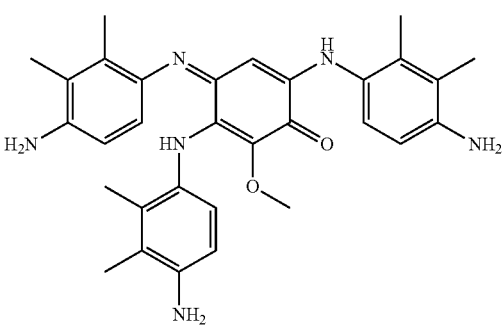

3,6-Bis(4-amino-2,3-dimethylphenylamino)-4-(4-amino-2,3-dimethylphenylimino)-2-methoxycyclohexa-2,5-dienone Compound 43

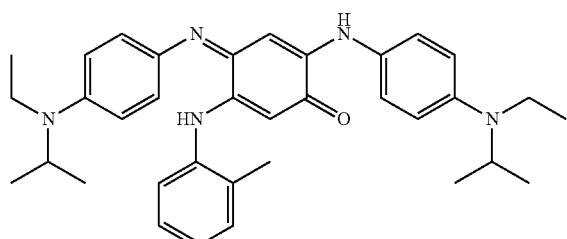

2-[4-(Ethylisopropyl-amino)phenyl-amino]-4-[4-ethyl-isopropylamino)-phenylimino]-5-o-tolyaminocyclohexa-2,5-dienone Compound 44

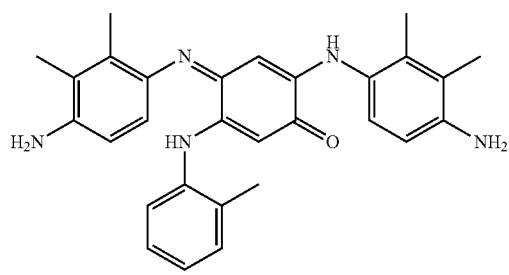

2-(4-Amino-2,3-dimethylphenylamino)-4-(4-amino-2,3-dimethylphenylimino)-5-o-tolylaminocyclohexa-2,5-dienone Compound 45

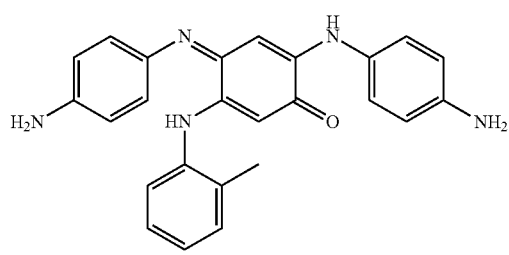

2-(4-Aminophenyl-amino)-4-(4-amino-phenylimino)-5-o-tolylaminocyclohexa-2,5-dienone Compound 46

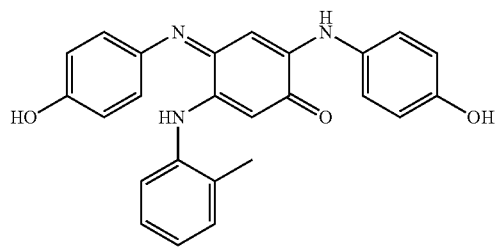

2-(4-Hydroxy-phenylamino)-4-(4-hydroxyphenylimino)-5-o-tolylamino-cyclohexa-2,5-dienone Compound 47

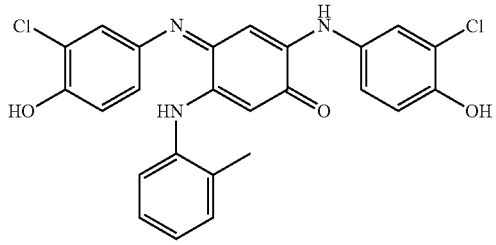

2-(3-Chloro-4-hydroxyphenylamino)-4-(3-chloro-4-hydroxy-phenylimino)-5-o-tolylaminocyclohexa-2,5-dienone Compound 48

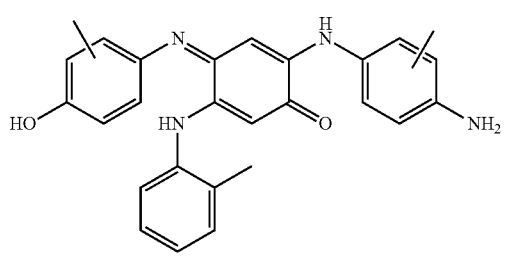

2-(2-Chloro-4-hydroxy-phenylamino)-4-(2-chloro-4-hydroxy-phenylimino)-5-o-tolylaminocyclohexa-2,5-dienone Compound 49

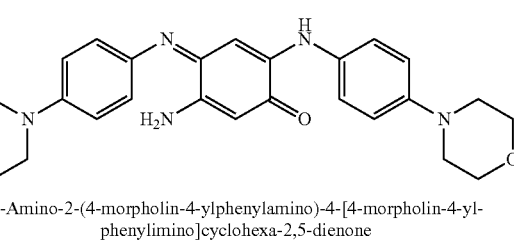

2-(4-Amino-3(or 2)-methylphenylamino)-4-(4-amino-3(or 2)-methyl-phenylimino)-5-o-tolylaminocyclohexa-2,5-dienone Compound 50

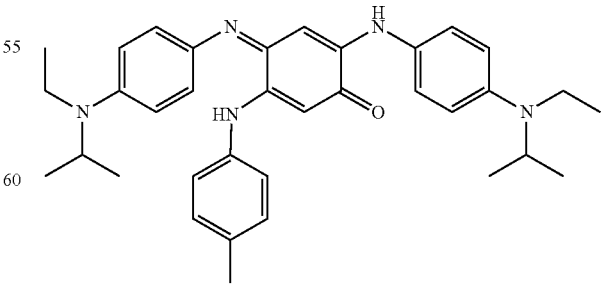

5-Amino-2-(4-morpholin-4-ylphenylamino)-4-[4-morpholin-4-yl-phenylimino]cyclohexa-2,5-dienone Compound 51

2-[4-(Ethylisopropyl-amino)phenyl-amino]-4-[4-(ethylisopropylamino)-phenylimino]-5-p-tolylaminocyclohexa-2,5-dienone -continued Compound 52

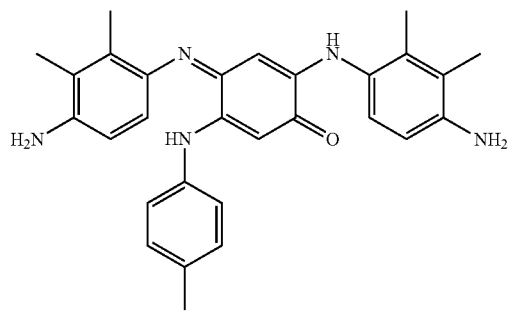

2-(4-Amino-2,3-dimethylphenylamino)-4-(4-amino-2,3-dimethyl-phenylimino)-5-p-tolylaminocyclohexa-2,5-dienone Compound 53

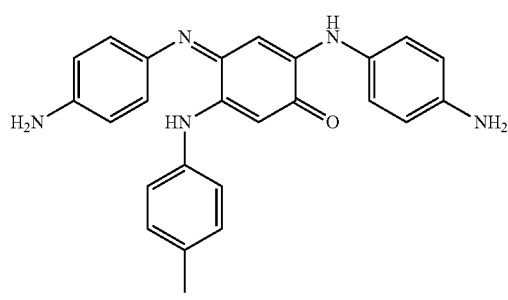

2-(4-Aminophenylamino)-4-(4-amino-phenylimino)-5-p-tolylaminocyclohexa-2,5-dienone Compound 54

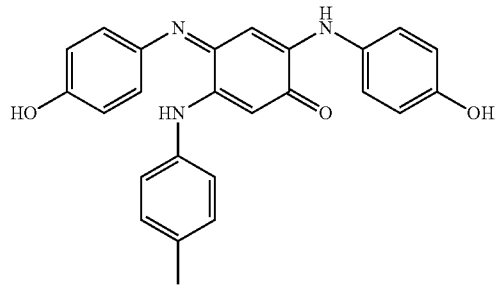

2-(4-Hydroxy-phenylamino)-4-(4-hydroxyphenylimino)-5-p-tolylaminocyclohexa-2,5-dienone Compound 55

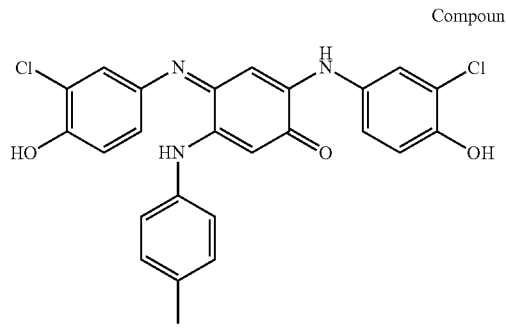

2-(3-Chloro-4-hydroxy-phenylamino)-4-(3-chloro-4-hydroxy-phenylimino)-5-p-tolylaminocyclohexa-2,5-dienone -continued Compound 56

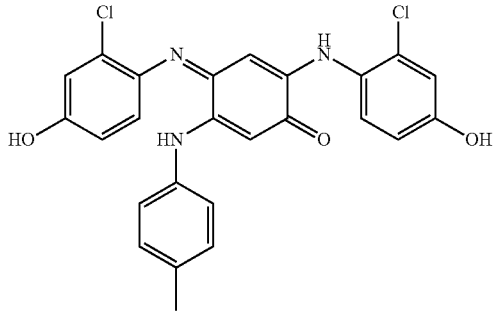

2-(2-Chloro-4-hydroxy-phenylamino)-4-(2-chloro-4-hydroxy-phenylimino)-5-p-tolylaminocyclohexa-2,5-dienone Compound 57

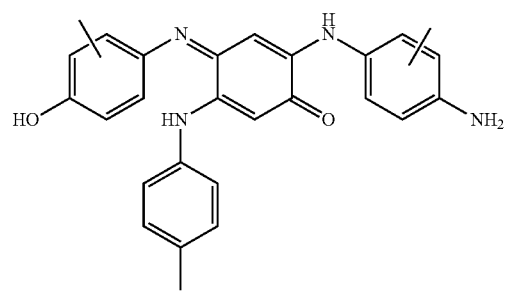

2-(4-Amino-3(or 2)-methylphenylamino)-4-(4-amino-3(or 2)-methyl-phenylimino)-5-p-tolylaminocyclohexa-2,5-dienone Compound 58

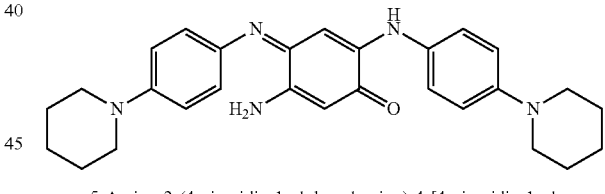

5-Amino-2-(4-piperidin-1-ylphenylamino)-4-[4-piperidin-1-yl-phenylimino]cyclohexa-2,5-dienone Compound 59

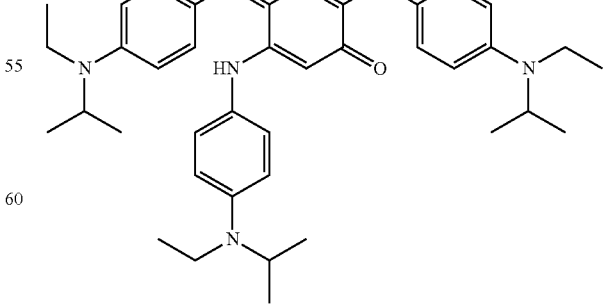

2,5-Bis[4-(ethylisopropyl-amino)-phenylamino]-4-[4-(ethylisopropyl-amino)phenylimino]-3-methylcyclohexa-2,5-dienone -continued Compound 60

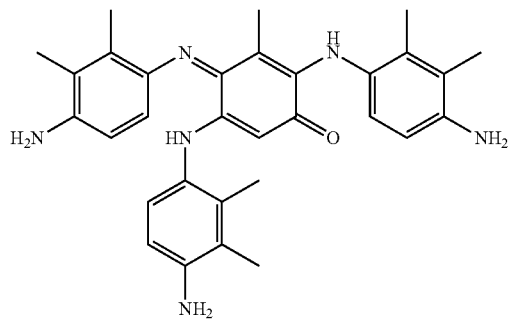

2,5-Bis(4-amino-2,3-dimethylphenylamino)-4-(4-amino-2,3-dimethyl-phenylimino)-3-methyl-cyclohexa-2,5-dienone Compound 61

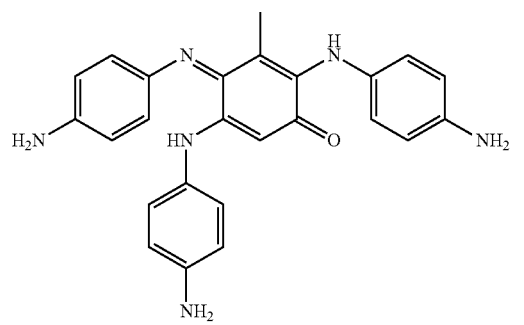

2,5-Bis(4-amino-phenylamino)-4-(4-aminophenylimino)-3-methyl-cyclohexa-2,5-dienone Compound 62

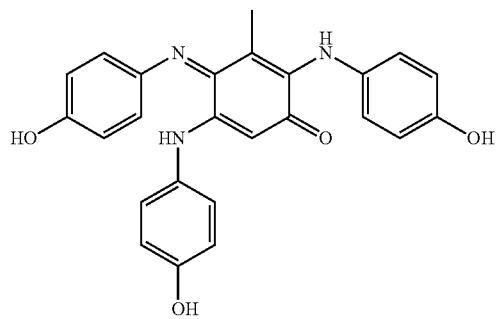

2,5-Bis(4-hydroxy-phenylamino)-4-(4-hydroxyphenylimino)-3-methylcyclohexa-2,5-dienone Compound 63

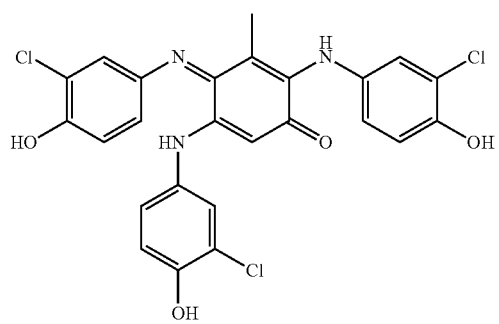

2,5-Bis(3-chloro-4-hydroxy-phenylamino)-4-(3-chloro-4-hydroxyphenylimino)-3-methylcyclohexa-2,5-dienone Compound 64

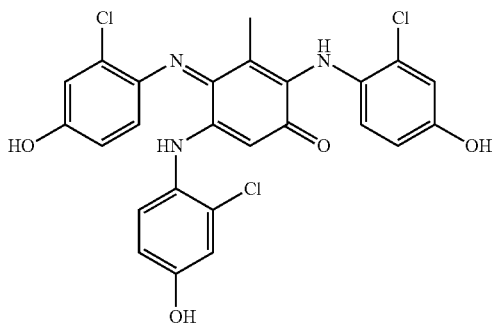

2,5-Bis(2-chloro-4-hydroxyphenylamino)-4-(2-chloro-4-hydroxy-phenylimino)-3-methyl-cyclohexa-2,5-dienone Compound 65

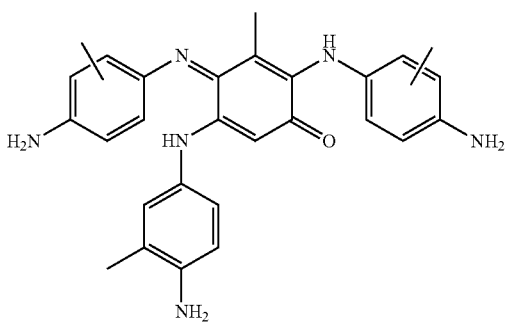

2,5-Bis(4-amino-3(or 2)-methylphenylamino)-4-(4-amino-3(or 2)-methyl-phenylimino)-3-methyl-cyclohexa-2,5-dienone Compound 66

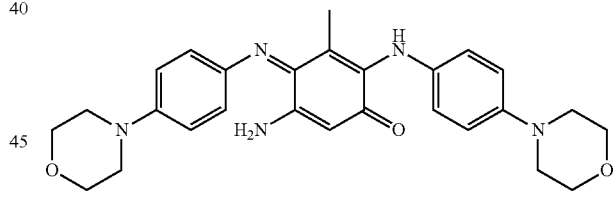

5-Amino-3-methyl-2-(4-morpholin-4-ylphenylamino)-4-[4-morpholin-4-ylphenylimino]cyclohexa-2,4-dienone Compound 67

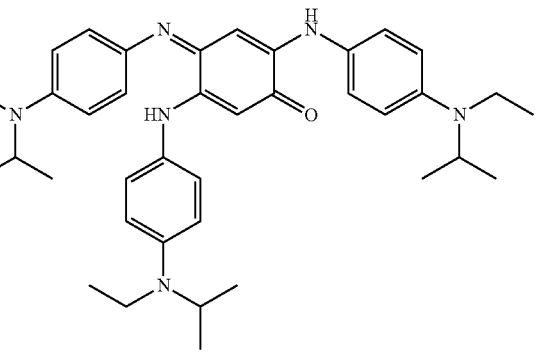

2,5-Bis[4-(ethylisopropyl-amino)-phenylamino]-4-[4-(ethylisopropylamino)-phenylimino]cyclohexa-2,5-dienone -continued Compound 68

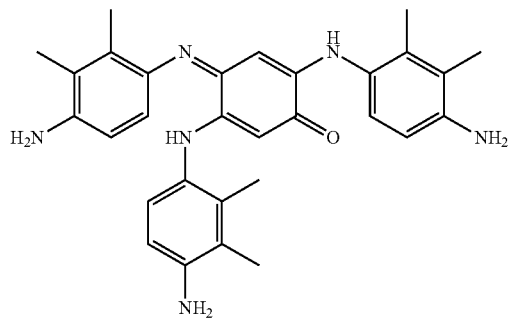

2,5-Bis(4-amino-2,3-dimethylphenylamino)-4-(4-amino-2,3-dimethyl-phenylimino)cyclohexa-2,5-dienone Compound 69

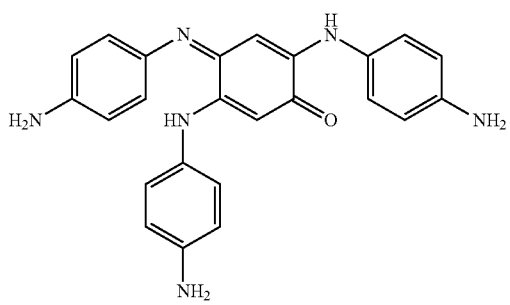

2,5-Bis(4-amino-phenylamino)-4-(4-aminophenylimino)-cyclohexa-2,5-dienone

Compound 70

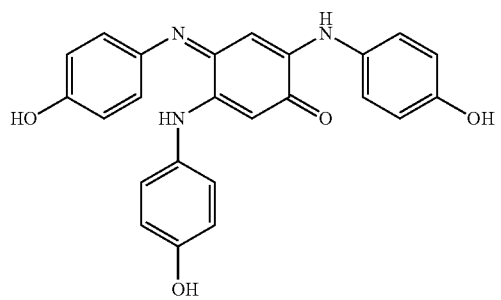

2,5-Bis(4-hydroxy-phenylamino)-4-(4-hydroxyphenylimino)-cyclohexa-2,5-dienone

Compound 71

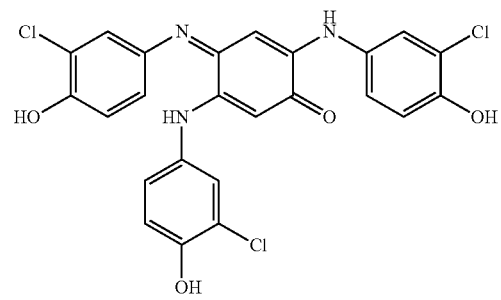

2,5-Bis(3-chloro-4-hydroxyphenylamino)-4-(3-chloro-4-hydroxy-phenylimino)cyclohexa-2,5-dienone -continued Compound 72

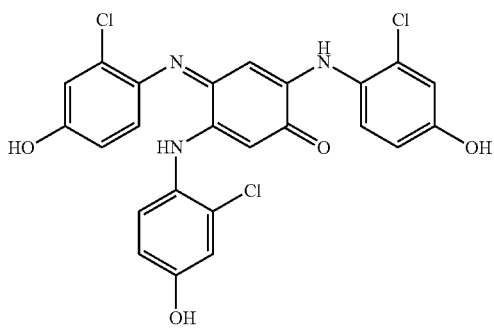

2,5-Bis(2-chloro-4-hydroxyphenylamino)-4-(2-chloro-4-hydroxy-phenylimino)cyclohexa-2,5-dienone Compound 73

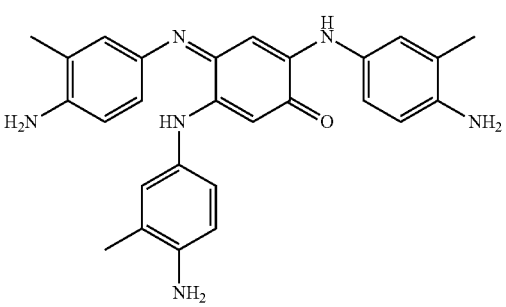

2,5-Bis(4-amino-3-methylphenylamino)-4-(4-amino-3-methyl-phenylimino)cyclohexa-2,5-dienone Compound 74

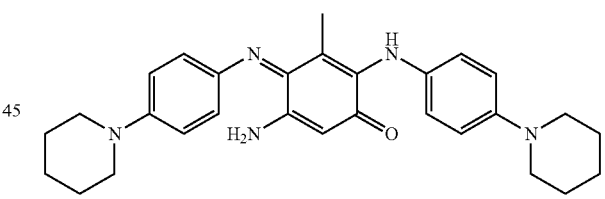

5-Amino-3-methyl-2-(4-piperidin-1-yl-phenylamino)-4-[4-piperidin-1-ylphenylimino]cyclohexa-2,5-dienone Compound 75

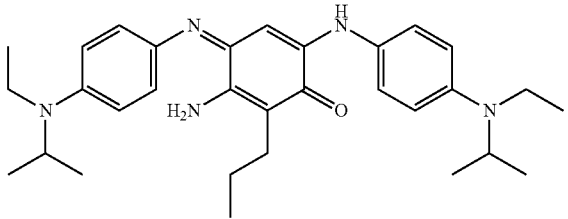

3-Amino-6-[4-(ethyl-isopropylamino)-phenylamino]-4-[4-ethyl-isopropylamino)-phenylimino]-2-propyl-cyclohexa-2,5-dienone Compound 76

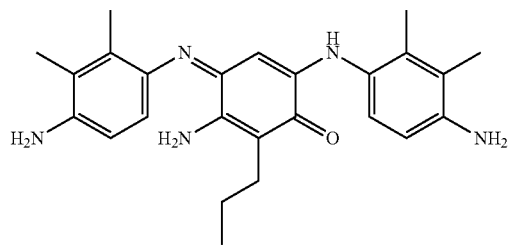

3-Amino-6-(4-amino-2,3-dimethylphenylamino)-4-(4-amino-2,3-dimethyl-phenylimino)-2-propyl-cyclohexa-2,5-dienone Compound 77

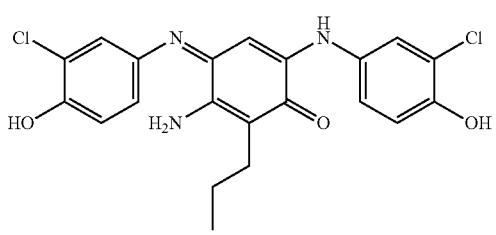

3-Amino-6-(3-chloro-4-hydroxyphenylamino)-4-(3-chloro-4-hydroxyphenylimino)-2-propyl-cyclohexa-2,5-dienone Compound 78

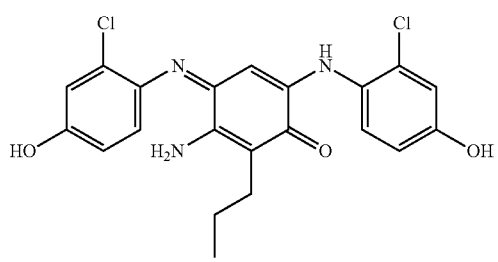

3-Amino-6-(2-chloro-4-hydroxyphenylamino)-4-(2-chloro-4-hydroxyphenylimino)-2-propyl-cyclohexa-2,5-dienone Compound 79

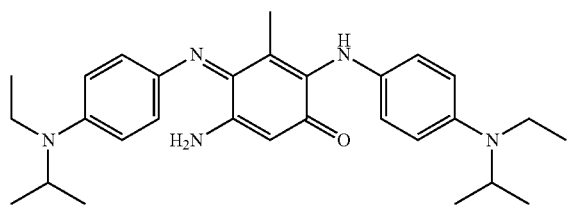

5-Amino-2-[4-(ethyl-isopropylamino)-phenylamino]-4-[4-(ethyl-isopropylamino)phenylimino]3-methylcyclohexa-2,5-dienone Compound 80

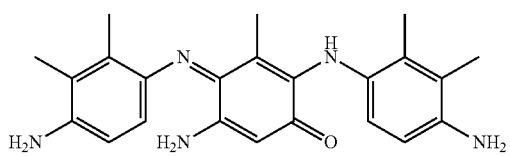

5-Amino-2-(4-amino-2,3-dimethylphenylamino)-4-(4-amino-2,3-dimethyl-phenylimino)-3-methyl-cyclohexa-2,5-dienone Compound 81

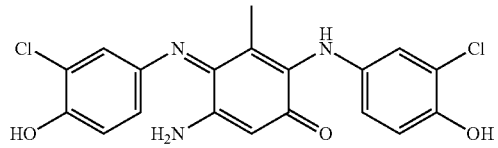

5-Amino-2-(3-chloro-4-hydroxyphenylamino)-4-(3-chloro-4-hydroxyphenylimino)-3-methyl-cyclohexa-2,5-dienone Compound 82

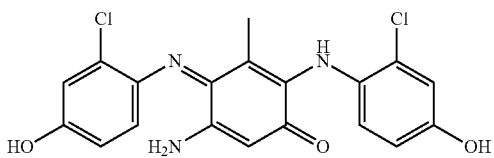

5-Amino-2-(2-chloro-4-hydroxyphenylamino)-4-(2-chloro-4-hydroxyphenylimino)-3-methyl-cyclohexa-2,5-dienone 9. Composition for dyeing keratin fibers, wherein the composition comprises, in a medium suitable for dyeing, one or more compounds of azomethine type having a triaromatic unit of formula (I) below and also the organic or inorganic acid or base salts thereof, the tautomeric, optical isomer or geometric isomer forms thereof and/or the solvates thereof:

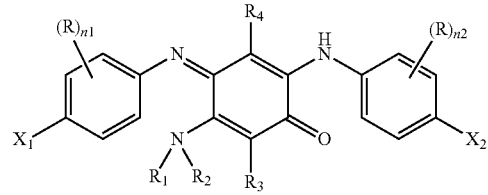

(I)

wherein:
$n_1$ and $n_2$ represent, independently of one another, an integer equal to 0, 1, 2, 3 or 4;
R represents:
  a linear or branched $C_1$-$C_4$ alkyl radical, optionally substituted with one or more identical or different radicals selected from hydroxyl or imidazolium, $An^-$ radicals; $An^-$ denoting a cosmetically acceptable anion or mixture of anions;
  a $C_1$-$C_4$ alkoxy radical;
  a halogen atom;
$R_1$ represents:
  a hydrogen atom;
  a linear or branched $C_1$-$C_8$ alkyl radical, optionally substituted with one or more hydroxyl radicals;
  an aminocarbonyl radical;
  a radical of formula (II):

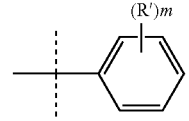

(II)

in which formula (II):
  m represents an integer equal to 0, 1, 2, 3 or 4;
  R' represents:
    a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;

a $C_1$-$C_4$ alkoxy radical;

a halogen atom;

a hydroxyl radical;

an —NR'$_3$R'$_4$ radical in which R'$_3$ and R'$_4$ represent, independently of one another:

a hydrogen atom;

a linear or branched $C_1$-$C_5$ alkyl radical, optionally substituted with one or more hydroxyl or $C_1$-$C_4$ alkoxy radicals;

it being understood that, in formula (II), when m is greater than or equal to 2, the R' radicals may be identical or different;

$R_2$ represents:

a hydrogen atom;

a $C_1$-$C_8$ alkyl radical, optionally substituted with one or more hydroxyl radicals;

$R_1$ and $R_2$ may form, together with the nitrogen atom to which they are attached, a pyrrolidine, piperidine or morpholine ring;

$R_3$ and $R_4$ represent, independently of one another:

a hydrogen atom;

a linear or branched $C_1$-$C_8$ alkyl radical, optionally substituted with one or more hydroxyl radicals;

a $C_1$-$C_4$ alkoxy radical;

$X_1$ and $X_2$ represent, independently of one another:

a hydroxyl radical;

an —NR"$_3$R"$_4$ radical in which:

R"$_3$ represents:

a hydrogen atom;

a linear $C_1$-$C_6$ alkyl radical;

R"$_4$ represents:

a hydrogen atom;

a linear or branched $C_3$-$C_6$ alkyl radical;

a linear or branched $C_2$-$C_6$ alkyl radical substituted with one or more hydroxyl radicals;

R"$_3$ and R"$_4$ may form, together with the nitrogen atom to which they are attached, a piperidino or morpholino ring;

it being understood that the compounds of formula (I) may not represent the compounds A to D below:

Compound A

Compound B

Compound C

Compound D

10. Method for dyeing keratin fibers, comprising:

applying to said fibers a dye composition comprising, in a medium suitable for dyeing, one or more direct dyes of formula (I) below, the organic or inorganic acid or base salts thereof, the tautomeric, optical isomer or geometric isomer forms thereof and/or the solvates thereof for a time sufficient to obtain a desired coloration:

(I)

wherein:

$n_1$ and $n_2$ represent, independently of one another, an integer equal to 0, 1, 2, 3 or 4;

R represents:

a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;

a $C_1$-$C_4$ alkoxy radical;

a halogen atom;

$R_1$ represents:

a hydrogen atom;

a linear or branched $C_1$-$C_8$ alkyl radical, optionally substituted with one or more hydroxyl radicals;

an aminocarbonyl radical;

a radical of formula (II):

$$(II)$$

[Structure of formula (II): a phenyl ring with $(R')_m$ substituents attached via a bond]

in which formula (II):
  m represents an integer equal to 0, 1, 2, 3 or 4;
  R' represents:
    a linear or branched $C_1$-$C_4$ alkyl radical, optionally substituted with one or more identical or different radicals selected from hydroxyl or imidazolium, $An^-$ radicals; $An^-$ denoting a cosmetically acceptable anion or mixture of anions;
    a $C_1$-$C_4$ alkoxy radical;
    a halogen atom;
    a hydroxyl radical;
    an —$NR'_3R'_4$ radical in which $R'_3$ and $R'_4$ represent, independently of one another:
      a hydrogen atom;
      a linear or branched $C_1$-$C_5$ alkyl radical, optionally substituted with one or more hydroxyl or $C_1$-$C_4$ alkoxy radicals;
    it being understood that, in formula (II), when m is greater than or equal to 2, the R' radicals may be identical or different;
$R_2$ represents:
  a hydrogen atom;
  a $C_1$-$C_8$ alkyl radical, optionally substituted with one or more hydroxyl radicals;
$R_1$ and $R_2$ may form, together with the nitrogen atom to which they are attached, a pyrrolidine, piperidine or morpholine ring;
$R_3$ and $R_4$ represent, independently of one another:
  a hydrogen atom;
  a linear or branched $C_1$-$C_8$ alkyl radical, optionally substituted with one or more hydroxyl radicals;
  a $C_1$-$C_4$ alkoxy radical;
$X_1$ and $X_2$ represent, independently of one another:
  a hydroxyl radical;
  an —$NR''_3R''_4$ radical in which:
    $R''_3$ represents:
      a hydrogen atom;
      a linear $C_1$-$C_6$ alkyl radical;
    $R''_4$ represents:
      a hydrogen atom;
      a linear or branched $C_3$-$C_6$ alkyl radical;
      a linear or branched $C_2$-$C_6$ alkyl radical substituted with one or more hydroxyl radicals;
$R''_3$ and $R''_4$ may form, together with the nitrogen atom to which they are attached, a piperidino or morpholino ring;
it being understood that the compounds of formula (I) may not represent the compounds A to D below:

Compound A

[Chemical structure of Compound A]

Compound B

[Chemical structure of Compound B]

Compound C

[Chemical structure of Compound C]

Compound D

[Chemical structure of Compound D]

rinsing the fibers;
optionally washing the fibers with shampoo;
optionally rinsing the fibers again; and
drying the resulting fibers or leaving the resulting fibers to dry.

11. Method for lightening keratin fibers, wherein (i) the dye composition as defined according to claim 9 free of oxidizing agent and (ii) a cosmetic composition comprising one or more oxidizing agents are applied to the keratin fibers; compositions (i) and (ii) being applied to said keratin fibers sequentially or simultaneously for a time sufficient to obtain a desired lightening, after which the fibers are rinsed, optionally washed with shampoo, rinsed again and the resulting fibers are dried or left to dry.

12. Leuco-type compound of formula (III) below, the organic or inorganic acid or base salts thereof, the tautomeric, optical isomer or geometric isomer forms thereof and/or the solvates thereof:

$$(III)$$

[Structure of formula (III): central benzene ring with $R_4$, $R_3$, OH, and $N(R_1)(R_2)$ substituents, flanked by two NH-phenyl groups bearing $(R)_{n1}$/$X_1$ and $(R)_{n2}$/$X_2$ substituents]

wherein:

$n_1$ and $n_2$ represent, independently of one another, an integer equal to 0, 1, 2, 3 or 4;

R represents:
- a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;
- a $C_1$-$C_4$ alkoxy radical;
- a halogen atom;

$R_1$ represents:
- a hydrogen atom;
- a linear or branched $C_1$-$C_8$ alkyl radical, optionally substituted with one or more hydroxyl radicals;
- an aminocarbonyl radical;
- a radical of formula (II):

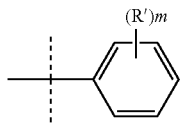
(II)

in which formula (II):
m represents an integer equal to 0, 1, 2, 3 or 4;
R' represents:
- a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;
- a $C_1$-$C_4$ alkoxy radical;
- a halogen atom;
- a hydroxyl radical;
- an —$NR'_3R'_4$ radical in which $R'_3$ and $R'_4$ represent, independently of one another:
  - a hydrogen atom;
  - a linear or branched $C_1$-$C_5$ alkyl radical, optionally substituted with one or more hydroxyl or $C_1$-$C_4$ alkoxy radicals;
- it being understood that, in formula (II), when m is greater than or equal to 2, the R' radicals may be identical or different;

$R_2$ represents:
- a hydrogen atom;
- a $C_1$-$C_8$ alkyl radical, optionally substituted with one or more hydroxyl radicals;

$R_1$ and $R_2$ may form, together with the nitrogen atom to which they are attached, a pyrrolidine, piperidine or morpholine ring;

$R_3$ and $R_4$ represent, independently of one another:
- a hydrogen atom;
- a linear or branched $C_1$-$C_8$ alkyl radical, optionally substituted with one or more hydroxyl radicals;
- a $C_1$-$C_4$ alkoxy radical;

$X_1$ and $X_2$ represent, independently of one another:
- a hydroxyl radical;
- an —$NR''_3R''_4$ radical in which:
  $R''_3$ represents:
  - a hydrogen atom;
  - a linear $C_1$-$C_6$ alkyl radical;
  $R''_4$ represents:
  - a hydrogen atom;
  - a linear or branched $C_3$-$C_6$ alkyl radical;
  - a linear or branched $C_2$-$C_6$ alkyl radical substituted with one or more hydroxyl radicals;

$R''_3$ and $R''_4$ may form, together with the nitrogen atom to which they are attached, a piperidino or morpholino ring.

13. Composition for dyeing keratin fibers, comprising one or more compounds of formula (III) as defined according to claim 12 and optionally comprising one or more oxidizing agents.

14. Method for dyeing keratin fibers, wherein a dye composition comprising one or more compounds of formula (III) as defined according to claim 12 and an oxidizing composition comprising one or more oxidizing agents are applied simultaneously or sequentially to said keratin fibers, which may be wet or dry.

15. Multicompartment device or "kit" comprising a first compartment containing a cosmetic composition comprising one or more dyes of formula (I) or containing one or more leuco-type compounds of formula (III), and a second compartment comprising one or more oxidizing agents:

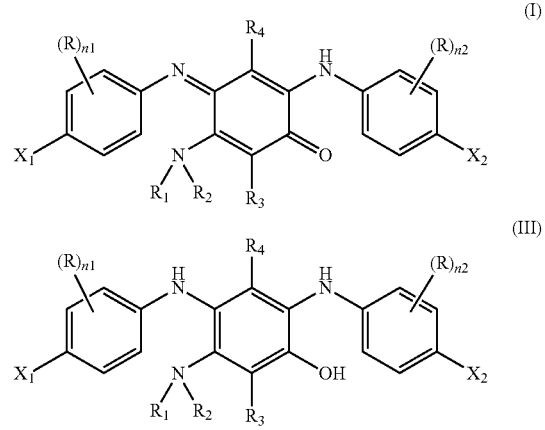

wherein:

$n_1$ and $n_2$ represent, independently of one another, an integer equal to 0, 1, 2, 3 or 4;

R represents:
- a linear or branched $C_1$-$C_4$ alkyl radical, optionally substituted with one or more identical or different radicals selected from hydroxyl or imidazolium, An⁻ radicals; An⁻ denoting a cosmetically acceptable anion or mixture of anions;
- a $C_1$-$C_4$ alkoxy radical;
- a halogen atom;

$R_1$ represents:
- a hydrogen atom;
- a linear or branched $C_1$-$C_8$ alkyl radical, optionally substituted with one or more hydroxyl radicals;
- an aminocarbonyl radical;

a radical of formula (II):

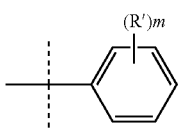

in which formula (II):
m represents an integer equal to 0, 1, 2, 3 or 4;
R' represents:
  a linear or branched $C_1$-$C_4$ alkyl radical, optionally substituted with one or more identical or different radicals selected from hydroxyl or imidazolium, $An^-$ radicals; $An^-$ denoting a cosmetically acceptable anion or mixture of anions;
  a $C_1$-$C_4$ alkoxy radical;
  a halogen atom;
  a hydroxyl radical;
  an —$NR'_3R'_4$ radical in which $R'_3$ and $R'_4$ represent, independently of one another:
    a hydrogen atom;
    a linear or branched $C_1$-$C_5$ alkyl radical, optionally substituted with one or more hydroxyl or $C_1$-$C_4$ alkoxy radicals;
  it being understood that, in formula (II), when m is greater than or equal to 2, the R' radicals may be identical or different;
$R_2$ represents:
  a hydrogen atom;
  a $C_1$-$C_8$ alkyl radical, optionally substituted with one or more hydroxyl radicals;
$R_1$ and $R_2$ may form, together with the nitrogen atom to which they are attached, a pyrrolidine, piperidine or morpholine ring;
$R_3$ and $R_4$ represent, independently of one another:
  a hydrogen atom;
  a linear or branched $C_1$-$C_8$ alkyl radical, optionally substituted with one or more hydroxyl radicals;
  a $C_1$-$C_4$ alkoxy radical;
$X_1$ and $X_2$ represent, independently of one another:
  a hydroxyl radical;
  an —$NR''_3R''_4$ radical in which:
    $R''_3$ represents:
      a hydrogen atom;
      a linear $C_1$-$C_6$ alkyl radical;
    $R''_4$ represents:
      a hydrogen atom;
      a linear or branched $C_3$-$C_6$ alkyl radical;
      a linear or branched $C_2$-$C_6$ alkyl radical substituted with one or more hydroxyl radicals;
  $R''_3$ and $R''_4$ may form, together with the nitrogen atom to which they are attached, a piperidino or morpholino ring;
it being understood that the compounds of formula (I) may not represent the compounds A to D below:

Compound A

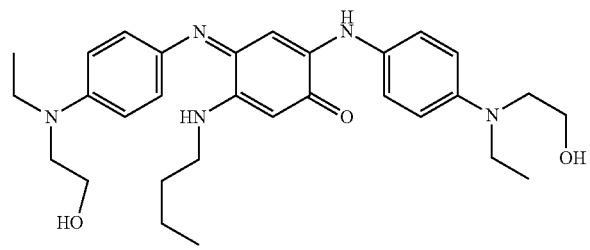

Compound B

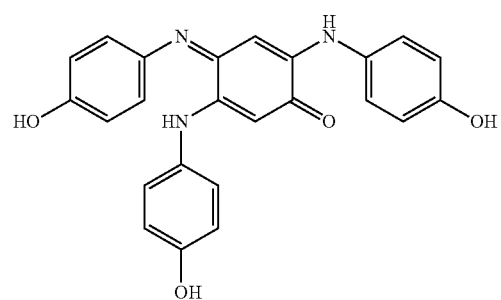

Compound C

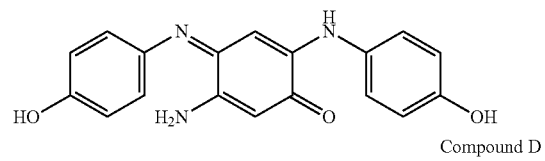

Compound D

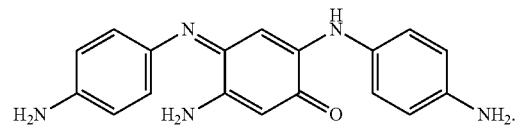

* * * * *

UNITED STATES PATENT AND TRADEMARK OFFICE
CERTIFICATE OF CORRECTION

PATENT NO. : 9,554,977 B2
APPLICATION NO. : 14/365217
DATED : January 31, 2017
INVENTOR(S) : Sabelle et al.

Page 1 of 3

It is certified that error appears in the above-identified patent and that said Letters Patent is hereby corrected as shown below:

In the Claims

Claim 8, Column 53, delete "Compound 4" in its entirety and insert Compound 4 as shown below:

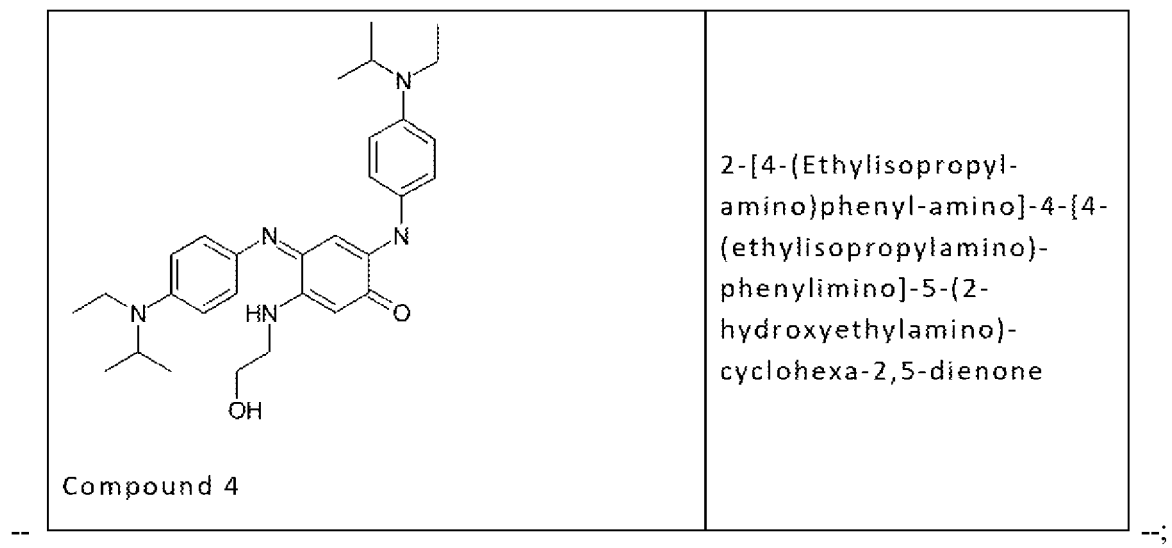

Signed and Sealed this
First Day of August, 2017

Joseph Matal
*Performing the Functions and Duties of the*
*Under Secretary of Commerce for Intellectual Property and*
*Director of the United States Patent and Trademark Office*

Claim 8, Column 54, delete "Compound 6" in its entirety and insert Compound 6 as shown below:

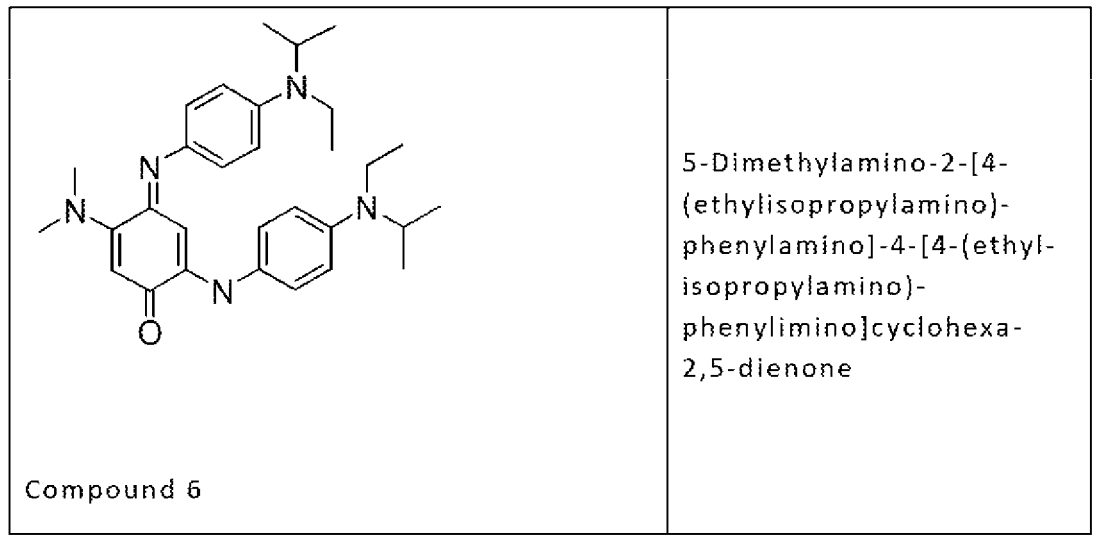

| | 5-Dimethylamino-2-[4-(ethylisopropylamino)-phenylamino]-4-[4-(ethyl-isopropylamino)-phenylimino]cyclohexa-2,5-dienone |
|---|---|
| Compound 6 | |

--                                                                                                                                                                                                                                                                   --;

Claim 8, Column 54, Line 65, change "isopropylamino]" to -- isopropylamino)-phenylimino] --;

Claim 8, Column 55, Line 65, change "diethylphenylimino)" to -- dimethylphenylimino) --;

Claim 8, Column 58, Lines 65-66, change "-4-hydroxyphenylamino)-cyclhexa-2,5-dienone" to -- -4-hydroxyphenylimino)-5-(2-hydroxyethylamino)cyclohexa-2,5-dienone --;

Claim 8, Column 59, Line 65, change "Ethylsopropylamine)" to -- Ethylisopropylamino) --;

Claim 8, Column 64, delete "Compound 49" in its entirety and insert Compound 49 as shown below:

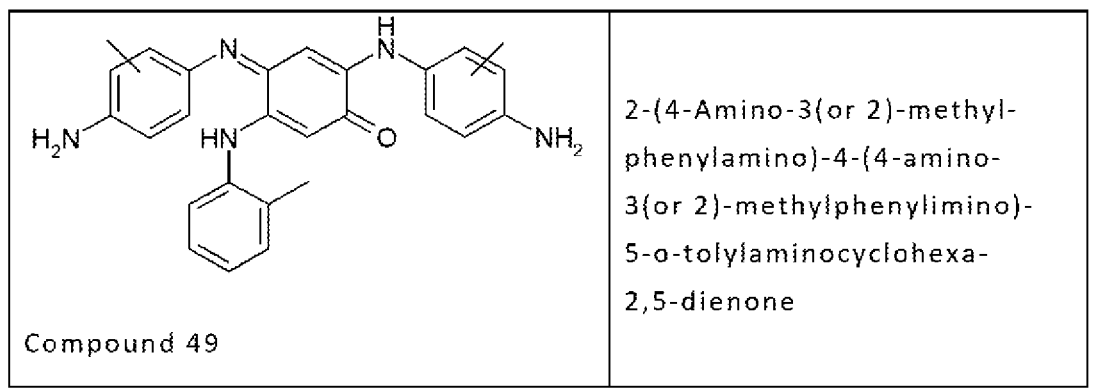

| | 2-(4-Amino-3(or 2)-methyl-phenylamino)-4-(4-amino-3(or 2)-methylphenylimino)-5-o-tolylaminocyclohexa-2,5-dienone |
|---|---|
| Compound 49 | |

--                                                                                                                                                                                                                                                                   --;

Claim 8, Column 66, delete "Compound 57" in its entirety and insert Compound 57 as shown below:

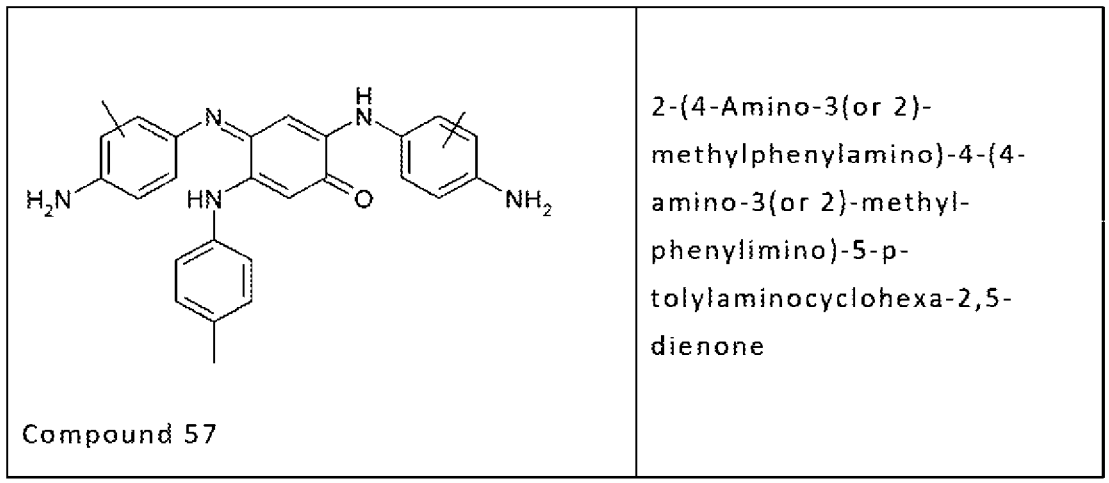

| 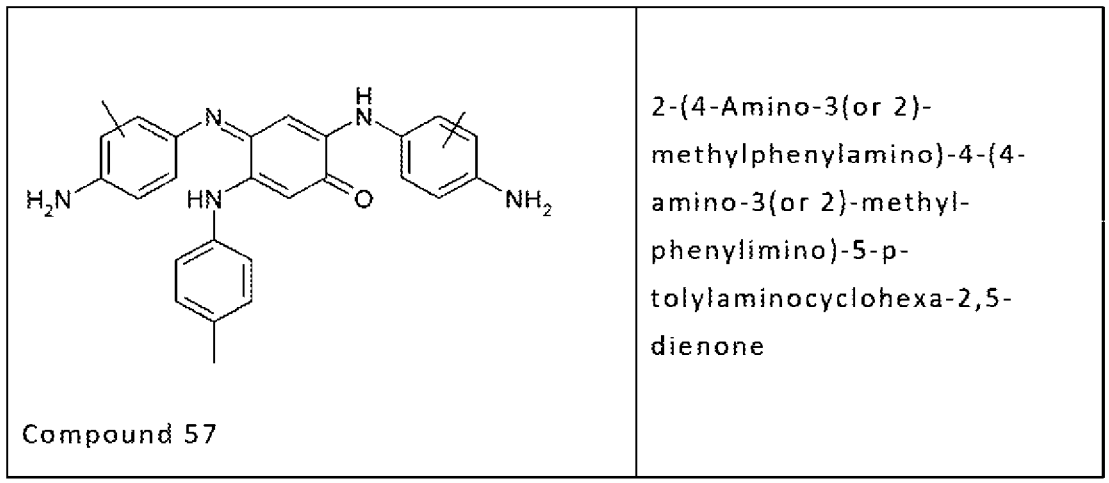 Compound 57 | 2-(4-Amino-3(or 2)-methylphenylamino)-4-(4-amino-3(or 2)-methyl-phenylimino)-5-p-tolylaminocyclohexa-2,5-dienone |

--                                                                                              --;

Claim 8, Column 68, Line 48, change "2,4-dienone" to -- 2,5-dienone --;

Claim 8, Column 71, Line 66, change "methyl-cyclohexa" to -- methylcyclohexa --;

Claim 8, Column 72, Line 10, change "methyl-cyclohexa" to -- methylcyclohexa --; and Claim 8, Column 72, Line 20, change "methyl-cyclohexa" to -- methylcyclohexa --.